United States Patent
Li et al.

(10) Patent No.: US 9,090,690 B2
(45) Date of Patent: Jul. 28, 2015

(54) ANTI NOTCH-1 ANTIBODIES

(75) Inventors: Kang Li, Richardson, TX (US); Ping Wei, San Diego, CA (US); Qinghai Peng, Del Mar, CA (US); John Andrew Lippincott, San Mateo, CA (US); Donna Marie Stone, Brisbane, CA (US); Zdenek Hostomsky, La Jolla, CA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 13/378,791

(22) PCT Filed: Jun. 16, 2010

(86) PCT No.: PCT/IB2010/052711
§ 371 (c)(1),
(2), (4) Date: Dec. 16, 2011

(87) PCT Pub. No.: WO2010/146550
PCT Pub. Date: Dec. 23, 2010

(65) Prior Publication Data
US 2012/0093813 A1    Apr. 19, 2012

Related U.S. Application Data

(60) Provisional application No. 61/218,193, filed on Jun. 18, 2009.

(51) Int. Cl.
| | |
|---|---|
| C07K 16/00 | (2006.01) |
| C07K 16/18 | (2006.01) |
| C07K 16/28 | (2006.01) |
| A61K 39/00 | (2006.01) |
| A61K 39/395 | (2006.01) |
| C07K 14/705 | (2006.01) |

(52) U.S. Cl.
CPC ............. *C07K 16/28* (2013.01); *A61K 39/395* (2013.01); *A61K 39/3955* (2013.01); *A61K 2039/505* (2013.01); *C07K 2316/96* (2013.01); *C07K 2317/56* (2013.01); *C07K 2317/565* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis et al. |
| 4,754,065 A | 6/1988 | Levenson et al. |
| 4,800,159 A | 1/1989 | Mullis et al. |
| 4,816,567 A | 3/1989 | Cabilly et al. |
| 5,047,335 A | 9/1991 | Paulson et al. |
| 5,225,539 A | 7/1993 | Winter et al. |
| 5,278,299 A | 1/1994 | Wong et al. |
| 5,510,261 A | 4/1996 | Goochee et al. |
| 5,530,101 A | 6/1996 | Queen et al. |
| 5,565,332 A | 10/1996 | Hoogenboom et al. |
| 5,580,717 A | 12/1996 | Dower et al. |
| 5,585,089 A | 12/1996 | Queen et al. |
| 5,624,821 A | 4/1997 | Winter et al. |
| 5,648,260 A | 7/1997 | Winter et al. |
| 5,677,425 A | 10/1997 | Bodmer et al. |
| 5,693,761 A | 12/1997 | Queen et al. |
| 5,693,762 A | 12/1997 | Queen et al. |
| 5,714,350 A | 2/1998 | Co et al. |
| 5,733,743 A | 3/1998 | Johnson et al. |
| 5,786,158 A | 7/1998 | Artavanis-Tsakonas et al. |
| 5,807,715 A | 9/1998 | Morrison et al. |
| 5,866,692 A | 2/1999 | Shitara et al. |
| 5,869,046 A | 2/1999 | Presta et al. |
| 5,997,867 A | 12/1999 | Waldmann et al. |
| 6,054,297 A | 4/2000 | Carter et al. |
| 6,121,022 A | 9/2000 | Presta et al. |
| 6,165,745 A | 12/2000 | Ward et al. |
| 6,180,370 B1 | 1/2001 | Queen et al. |
| 6,180,377 B1 | 1/2001 | Morgan et al. |
| 6,194,551 B1 | 2/2001 | Idusogie et al. |
| 6,210,671 B1 | 4/2001 | Co |
| 6,265,150 B1 | 7/2001 | Terstappen et al. |
| 6,277,375 B1 | 8/2001 | Ward |
| 6,331,415 B1 | 12/2001 | Cabilly et al. |
| 6,350,861 B1 | 2/2002 | Co et al. |
| 7,666,982 B2 | 2/2010 | Okochi et al. |
| 7,919,092 B2 | 4/2011 | Lewicki et al. |
| 2003/0148954 A1 | 8/2003 | Bresnick et al. |
| 2004/0110704 A1 | 6/2004 | Yamane et al. |
| 2005/0026831 A1 | 2/2005 | Bodmer et al. |

(Continued)

FOREIGN PATENT DOCUMENTS

| | | |
|---|---|---|
| EP | 0154316 B1 | 9/1985 |
| EP | 0176195 A2 | 4/1986 |

(Continued)

OTHER PUBLICATIONS

Bork et al. Powers andpitfalls in sequence analysis: the 70% hurdle. Genome Res 10: 398-400, 2000.*
Bork et al. Go hunting in sequence databases but watch out for the traps. Trends in Genet 12(10: 425-427, 2000.*
Brenner, S.E. Errors in genome annotation. Trends in Genet 15(4): 132-133, 1999.*
Brorson et al. Mutational analysis of avidity and fine specificity of anti-levan antibodies. J Immunol 163: 6694-6701, 1999.*
Brummell et al. Probing the combining site of an anti-carbohydrate antibody by saturation-mutagenesis: role of the heavy-chain CDR3 residues. Blochem 32(4): 1180-1187, 1993.*
Burks et al. In vitro scanning saturation mutagenesis of an antibody binding pocket. Proc Natl Acad Sci USA 94: 412-417, 1997.*
Colman, P.M. Effects of amino acid sequence changes on antibody-antigen interactions. Res Immunol 145: 33-36, 1994.*
Doerks et al. Protein annotation: detective work for function prediction. Trends in Genet 14(6): 248-250, 1996.*

(Continued)

*Primary Examiner* — Bridget E Bunner
(74) *Attorney, Agent, or Firm* — Carol A. McKeever

(57) ABSTRACT

This invention is directed toward monoclonal antibodies that bind specifically to Notch1. In one embodiment, the antibodies binds to at least a first epitope and a second epitope, wherein the first epitope resides with the LinA domain of the Notch1 negative regulatory region (NRR), and the second epitope resides within the HD-C domain of the Notch1 NRR.

12 Claims, 10 Drawing Sheets

(56) References Cited

U.S. PATENT DOCUMENTS

| | | |
|---|---|---|
| 2007/0071742 A1 | 3/2007 | Fang et al. |
| 2007/0072222 A1 | 3/2007 | Boess et al. |
| 2008/0206753 A1 | 8/2008 | Egan et al. |
| 2008/0220416 A1 | 9/2008 | Miele et al. |
| 2008/0241150 A1 | 10/2008 | Blacklow et al. |
| 2008/0267971 A1 | 10/2008 | Green et al. |
| 2009/0081238 A1 | 3/2009 | Siebel et al. |
| 2009/0137470 A1 | 5/2009 | Stylianou |
| 2009/0155256 A1 | 6/2009 | Black et al. |
| 2010/0062012 A1 | 3/2010 | Ioannides et al. |

FOREIGN PATENT DOCUMENTS

| | | |
|---|---|---|
| EP | 0401384 B1 | 12/1990 |
| EP | 0519596 A1 | 12/1992 |
| EP | 0619596 A1 | 10/1994 |
| EP | 1 176 195 A1 | 1/2002 |
| WO | WO8704462 | 7/1987 |
| WO | WO9306213 | 4/1993 |
| WO | WO 94/07474 A1 | 4/1994 |
| WO | WO9429351 | 12/1994 |
| WO | WO9954342 | 10/1999 |
| WO | WO9958572 | 11/1999 |
| WO | WO 00/20576 A2 | 4/2000 |
| WO | WO0042072 | 7/2000 |
| WO | WO0127160 | 4/2001 |
| WO | 02/059285 A1 | 8/2002 |
| WO | WO03035835 | 5/2003 |
| WO | WO2004058184 | 7/2004 |
| WO | WO 2005/054434 A2 | 6/2005 |
| WO | WO 2006/015375 A2 | 2/2006 |
| WO | WO 2006/053063 A2 | 5/2006 |
| WO | WO 2007/061988 A2 | 5/2007 |
| WO | WO 2008/150525 A1 | 12/2008 |
| WO | WO 2010/005567 | 1/2010 |
| WO | WO2010059543 | 5/2010 |
| WO | WO 2010/146550 A1 | 12/2010 |
| WO | WO 2011/041336 A2 | 4/2011 |
| WO | WO 2011/088215 A2 | 7/2011 |
| WO | WO 2012/080891 A1 | 6/2012 |
| WO | WO 2012/080926 A2 | 6/2012 |

OTHER PUBLICATIONS

Jang et al. The structural basis for DNA binding by an anti-DNA autoantibody. Mol Immunol 35: 1207-1217, 1998.*

Kobayashi et al. Tryptophan H33 plays an important role in pyrimidine (6-4) pyrimidone photoproduct binding by a high-affinity antibody. Protein Engineering 12(10): 879-884, 1999.*

Ngo et al. Computational complexity, protein structure prediction, and the Levinthal paradox. The Protein Folding Problem and Tertiary Structure Prediction, pp. 492-495, 1994.*

Rudikoff et al. Single amino acid substitition altering antigen-binding specificity. Proc Natl Acad Sci USA 79: 1979-1983, 1982.*

Skolnick et al. From genes to protein structure and function: novel applications of computational approaches in the genomic era. Trends in Biotech 18(1): 34-39, 2000.*

Smith et al. The challenges of genome sequence annotation or "The devil is in the details". Nature Biotech 15: 1222-1223, 1997.*

Tokuriki et al. Stability effects of mutations and protein evolvability. Curr Opin Structural Biol 19: 596-604, 2009.*

Wells. J.A. Additivity of mutational effects in proteins. Biochemistry 29 (37): 8509-8517, 1990.*

Tramontano, A., et al., "Framework Residue 71 is a Major Determinant of the Position and Conformation of the Second Hypervariable Region in the VH Domains of Immunoglobulins", J. Mol. Biol. 1990, 175-182, vol. 215.

Tun, T., et al., "Recognition Sequence of a Highly Conserved DNA Binding Protein RBP-Jx", Nucleic Acids Research, 1994, 965-971, vol. 22, No. 6.

Umaña, P., et al., "Engineered Glycoforms of an Antineuroblastoma IgG1 with Optimized Antibody-dependent Cellular Cytotoxic Activity", Nature Biotechnology, 1999, 176-180, vol. 17.

Vardar, D., et al., "Nuclear Magnetic Resonance Structure of a Prototype Lin12-Notch Repeat Module from Human Notch1", Biochemistry, 2003, 7061-7067, vol. 42.

Verhoeyen, M., et al. "Reshaping Human Antibodies: Grafting an Antilysozyme Activity", Science, 1988, 1534-6, vol. 239.

Waterhouse, P., et al., "Combinatorial Infection and In Vivo Recombination: a Strategy for Making Large Phage Antibody Repertoires," Nucleic Acids Research, 1993, 2265-2266, vol. 21, No. 9.

Winter, G., et al., "Making antibodies by phage display technology", Annu. Rev. Immunol., 1994, 433-55, vol. 12.

Winter, G., et al., "Man-Made Antibodies", Nature, 1991, 293-299, vol. 349.

Wittwer, A., et al., "Glycosylation at Asn- 184 Inhibits the Conversion of Single-Chain to Two-Chain Tissue-Type Plasminogen Activator by Plasmin", Biochemistry, 1990, 4175-4180, vol. 29.

Wu, Y., et al., "Therapeutic Antibody Targeting of Individual Notch Receptors", Nature, 2010, 1052-1057, vol. 464.

Wyss, D., et al., "The Structural Role of Sugars in Glycoproteins", Current Opinion in Biotechnology, 1996, 409-416, vol. 7.

Yamane-Ohnuki, N., et al., Establishment of FUT8 Knockout Chinese Hamster Ovary Cells: An Ideal Host Cell Line for Producing Completely Defucosylated Antibodies With Enhanced Antibody-Dependent Cellular Cytotoxicity, Biotechnology and Bioengineering, 2004, 614-622, vol. 87, No. 5.

Yelton, D., et al., "Affinity Maturation of the BR96 Anti-Carcinoma Antibody by Codon-Based Mutagenesis", The Journal of Immunology, 1995, 1994-2004, vol. 155.

Kim, J., et al., "Localization of the site of the murine IgGI molecule that is involved in binding to the murine intestinal Fc receptor", Eur. J. Immunol., 1994, 2429-2434, vol. 24.

International Search Report, for PCT/IB2010/052711; Oct. 19, 2010.

Hong et al, "Overexpression of Notch 1 signaling associates with the tumorigenesis of gastric adenorna and intestinal type of gastric cancer", Gastroenterology 132(Issue 4-Suppl.2):AGA Abstract # T2084:p. A617 (2007).

Kipriyanov et al, "Generation and production of engineered antibodies" Molecular Biotechnology 26(1):39-60 (2004).

Li et al, "Modulation of Notch Signaling by antibodies specific for the extracellular negative regulatory region onf NOTCH3", Journal of Biological Chemistry 283(12):8046-8054 (2008).

Andresen, H., "Development of peptide microarrays for epitope mapping of antibodies against the human TSH receptor," Journal of Immunological Methods, 2006, 11-18, vol. 315.

Armour, C., et al., "Recombinant human IgG molecules lacking Fcγ receptor I binding and monocyte triggering activities," Eur. J. Immunol., 1999,2613-2624, vol. 29.

Aste-Amezaga, M., et al., "Characterization of Notch1 Antibodies That Inhibit Signaling of Both Normal and Mutated Notch1 Receptors," Plos One, 2010, 1-13, vol. 5, No. 2.

Balint, R., et al., "Antibody engineering by parsimonious mutagenesis", Gene,109-118,1993, vol. 137.

Barbas, III, C., et al., "In vitro evolution of a neutralizing human antibody to human immunodeficiency virus type 1 to enhance affinity and broaden strain cross-reactivity", Proc. Nat. Acad. Sci. USA, 1994, 3809-3813, vol. 91.

Boyd, P., et al., "The effect of the removal of sialic acid, galactose and total carbohydrate on the functional activity of campath-IH", Molecular Immunology, 1995,1311-1318, vol. 32.

Brown, B., et al., "Tumor-specific Genetically Engineered Murine/Human Chimeric Monoclonal Antibody", Cancer Research, 1987, 3577-3583, vol. 47.

Capel, P., et al., "Heterogeneity of Human IgG Fc Receptors", Immunomethods, 1994, 25-34, vol. 4.

Daeron, M., "Fc Receptor Biology", Annu. Rev. Immunol., 1997, 203-34, vol. 15.

Daugherty, B., et al., "Polymerase chain reaction facilitates the cloning, CDR-grafting,and rapid expression of a murine monoclonal antibody directed against the CD18 component of leukocyte integrins", Nucleic Acids Research, 1991, 2471-2476, vol. 19, No. 9.

Dhungana, S., et al., "Epitope Mapping by Proteolysis of Antigen—Antibody Complexes", Methods in Molecular Biology, 2009, 87-101, vol. 524.

(56) References Cited

OTHER PUBLICATIONS

Efstratiadis, A., et al., "Notch, Myc and Breast Cancer", Cell Cycle, 2007, 418-429, vol. 6, No. 4.
Gordon, W., et al., "Structural basis for autoinhibition of Notch", Nature Structural & Molecular Biology, 2007, 295-300, vol. 14, No. 4.
Gordon, W., et al., "Structure of the Notch1-negative regulatory region: implications for normal activation and pathogenic signaling in T-ALL", Blood, 2009, 4381-4390, vol. 113.
Guyer, R., et al., "Immunoglobulin binding by mouse intestinal epithelial cell receptors", The Journal of Immunology, 1976, 587-593, vol. 117, No. 2.
De Haas, M., et al., "Fcy receptors of phagocytes", J. Lab. Clin. Med.,1995, 330-341, vol. 126.
Hawkins, R., et al., "Selection of phage antibodies by binding affinity mimicking affinity maturation", J. Mol. Biol., 1992, 889-896, vol. 226.
Hsu, T., et al., "Differential N-Glycan Patterns of Secreted and Intracellular IgG Produced in Trichoplusia ni Cells", The Journal of Biological Chemistry, 1997, 9062-9070, vol. 272, No. 14.
Hu, C., et al., "Overexpression of Activated Murine Notch1 and Notch3 in Transgenic Mice Blocks Mammary Gland Development and Induces Mammary Tumors", American Journal of Pathology, 2006, 973-990, vol. 168, No. 3.
Idusogie, E., et al., "Mapping of the C1q Binding Site on Rituxan, a Chimeric Antibody with a Human IgG1 Fc", The Journal of Immunology, 2000, 4178-4184, vol. 164.
Jackson, J., et al., "In vitro antibody maturation, improvement of a high affinity, neutralizing antibody against IL-1β", The Journal of Immunology, 1995, 3310-3319, vol. 154.
Jefferis, R., et al., "IgG-Fc-mediated effector functions: molecular definition of interaction sites for effector ligands and the role of glycosylation", Immunological Reviews, 1998, 59-76, vol. 163.
Jones, P., et al., "Replacing the complementarity-determining regions in a human antibody with those from a mouse", Nature, 1986, 522-525, vol. 321.
Kang, S. et al., "Bacterial cell surface display for epitope mapping of hepatitis C virus core antigen", FEMS Microbiology Letters, 2003, 347-353, vol. 226.
Lee, B., et al., "Epitope Mapping of CCR5 Reveals Multiple Conformational States and Distinct but Overlapping Structures Involved in Chemokine and Coreceptor Function", The Journal of Biological Chemistry, 1999, 9617-9626, vol. 274, No. 14.
Levy, R., et al., "Fine and Domain-level Epitope Mapping of Botulinum Neurotoxin Type A Neutralizing Antibodies by Yeast Surface Display", Journal of Molecular Biology, 2007, 196-210, vol. 365.
LoBuglio, A., et al., "Mouse/Human Chimeric Monoclonal Antibody in Man: Kinetics and Immune Response", Proc. Natl. Acad. Sci. USA, 1989, 4220-4224, vol. 86.
Lonberg, N., et al., "Human Antibodies from Transgenic Mice", Intern. Rev. Immunol., 1995, 65-93, vol. 13.
Lund, J., et al., "Multiple Interactions of IgG with Its Core Oligosaccharide Can Modulate Recognition by Complement and Human Fcy Receptor I and Influence the Synthesis of Its Oligosaccharide", The Journal of Immunology, 1996, 4963-4960, vol. 157.
Malecki, M., et al., "Leukemia-Associated Mutations within the NOTCH1 Heterodimerization Domain Fall into at Least Two Distinct Mechanistic Classes", Molecular and Cell Biology, 2006, 4642-4651, vol. 26, No. 12.
Marks, J., et al., "By-Passing Immunization: Building High Affinity Human Antibodies by Chain Shuffling", Bio/Technology, 1992, 779-783, vol. 10.
McCafferty, J., et al., "Phage Antibodies: Filamentous Phage Displaying Antibody Variable Domains", Nature, 1990, 552-554, vol. 348.
Morgan, A., et al., "The N-Terminal End of the CH2 Domain of Chimeric Human IgG1 Anti-HLA-DR is Necessary for C1q, FcγRI and FcγRIII Binding", Immunology, 1995, 319-324, vol. 86.
Morikawa, S., et al., "Two E-Rosette-Forming Lymphoid Cell Lines", Int. J. Cancer, 1978, 166-170, vol. 21.
Morrison, S., et al., "Chimeric Human Antibody Molecules: Mouse Antigen-Binding Domains With Human Constant Region Domains", Proc. Nati. Acad. Sci. USA, 1984, 6851-6855, vol. 81.
Osipo, C., et al., "ErbB-2 Inhibition Activates Notch-1 and Sensitizes Breast Cancer Cells to a y-Secretase Inhibitor", Oncogene, 2008, 5019-5032, vol. 27.
Paes, C., et al., "Atomic-Level Mapping of Antibody Epitopes on a GPCR", J. Am. Chem. Soc., 2009, 6952-6954, vol. 131.
Peeters, K., et al., "Production of Antibodies and Antibody Fragments in Plants", Vaccine, 2001, 2756-2761. vol. 19.
Pollock, D., et al., "Transgenic Milk as a Method for the Production of Recombinant Antibodies", Journal of Immunological Methods, 1999, 147-157, vol. 231.
Queen, C., et al., "A Humanized Antibody that Binds to the Interleukin 2 Receptor", Proc. Nati. Acad. Sci. USA, 1989, 10029-10033, vol. 86.
Ravetch, J., et al., "Fc receptors", Annu. Rev. Immunol., 1991, 457-92, vol. 9.
Reedijk, M., et al., "High-level Coexpression of JAG1 and NOTCH1 is Observed in Human Breast Cancer and is Associated with Poor Overall Survival", Cancer Research, 2005; 8530-8537, vol. 65.
Riechmann, L., et al., "Reshaping Human Antibodies for Therapy", Nature, 1998, 323-327, vol. 332.
Rockberg, J., et al., "Epitope Mapping of Antibodies Using Bacterial Surface Display", Nature Methods, 2008, 1039-1045, vol. 5, No. 12.
Sanchez-Irizarry, C., et al., "Notch Subunit Heterodimerization and Prevention of Ligand-Independent Proteolytic Activation Depend, Respectively, on a Novel Domain and the LNR Repeats", Molecular and Cell Biology, 2004, 9265-9273, vol. 24, No. 21.
Schier, R., et al., "Identification of Functional and Structural Amino-Acid Residues by Parsimonious Mutagenesis", Gene, 1996, 147-155, vol. 169.
Shaw, R., et al., "Characterization of a Mouse/Human Chimeric Monoclonal Antibody (17-1a) to a Colon Cancer Tumor-Associated Antigen", The Journal of Immunology, 1987, 4534-4538, vol. 138, No. 12.
Shields, R., et al., "High Resolution Mapping of the Binding Site on Human IgG1 for FcyRI, FcyRII, FcyRIII, and FcRn and Design of IgG1 Variants with Improved Binding to the FcyR", The Journal of Biological Chemistry, 2001, 6591-6604, vol. 276, No. 9.
Shields, R., et al., "Lack of Fucose on Human IgG1 N-Linked Oligosaccharide Improves Binding to Human FcyRIII and Antibody-dependent Cellular Toxicity", The Journal of Biological Chemistry, 2002, 26733-26740, vol. 277, No. 30.
Tao, M., et al., Studies of Aglycosylated Chimeric Mouse-Human IgG Role of Carbohydrate in the Structure and Effector Functions Mediated by the Human IgG Constant Region, The Journal of Immunology, 1989, 2595-2601, vol. 143, No. 8.
Altschuler et al, Uspekhi Biologicheskoi Khimmii, vol. 50, pp. 207-208 (2010).
Duquesnoy et al, "Structural and Functional Definitions of Epitopes Reacting with Mouse Monoclonal Antibodies", URL: HLAMatchmake Website; http://www.hlamatchmaker.net/documents/01structure.pdf.
Hwang et al, "Immunogenicity of engineered antibodies", Methods 36:3-10 (2005).
Kussie et al, "A Single Engineered Amino Acid Substitution Changes Antibody Fine Specificity", Journal of Immunology 152(1):146-152 (1994).
Ohno et al, "Antigen-binding specificities of antibodies are primarily determined by seven residues of VH", Proc. Natl. Acad. Sci. USA 82:2945-2949 (1985).
Pakula et al, "Genetic Analysis of Protein Stability and Function", Annual Review of Genetics 23:289-310 (1989).
Schildbach et al, "Modulation of antibody affinity by a non-contact residue", Protein Science 2:206-214 (1993).
Caldas et al, "Humanization of the anti-CD18 antibody 6.7: an unexpected effect of a framework residue in binding to antigen", Molecular Immunology 39:941-952 (2003).

(56) References Cited

OTHER PUBLICATIONS

Krauss et al, "Impact of antibody framework residue VH-71 on the stability of a humanised anti-MUCI scFv and derived immunoenzyme", British Journal of Cancer 90:1863-1870 (2004).
Paul, Fundamental Immunology, Raven Press, New York, p. 270 (1989).
Roitt et al, Immunology, 5th edition, pp. 71 & 73 (1998).
Bowie, et al., "Deciphering the Message in Protein Sequences: Tolerance to Amino Acid Substitutions," *Science*, 247:1306-1310 (1990).
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *J. Cell Biol.*, 111: 2129-2138 (1990).
Lazar, et al., "Transforming Growth Factor α: Mutation of Aspartic Acid 47 and Leucine 48 Results in Different Biological Activities," *Mol. Cell. Biol.*, 8:1247-1252 (1988).
Aster et al, "The Folding and Structural Integrity of the First LIN-12 Module of Human Notch1 are Calcium-Dependent", Biochemistry 38:4736-4742 (1999).
Bray, "Notch signalling: a simple pathway becomes complex", Nature Reviews: Molecular Cell Biology 7(9):678-689 (2006).
Chen, J., "Force-induced unfolding simulations of the human Notch1 negative regulatory region: possible roles of the heterodimerization domain in mechanosensing," PLoS One, 6(7):e22837 11 pages (2011).
Falk et al., "Generation of anti-Notch antibodies and their application in blocking Notch signalling in neural stem cells", Methods, 58(1):69-78 (2012).
Harrison et al, "The Manufacturing Process for Recombinant Factor IX", Seminars in Hematology, 35(2 Suppl 2):4-10 (1998).
Hellström et al, "Dll4 signalling through Notch1 regulates formation of tip cells during angiogenesis", Nature 445:776-780 (2007).
Jeffries et al, "Characterization of a High-Molecular-Weight Notch Complex in the Nucleus of Notch$^{ic}$-Transformed RKE Cells and in a Human T-Cell Leukemia Cell Line", Molecular and Cellular Biology 22(11):3927-3941 (2002).
Kidd et al, "Structure and distribution of the Notch protein in developing *Drosophila*", Genes & Development 3(8):1113-1129 (1989).
Klinakis et al, "Myc is a Notch1 transcriptional target and a requisite for Notch1-induced mammary tumorigenesis in mice", Proceedings of the National Academy of Sciences USA 103(24):9262-9267 (2006).
Li et al, "Distinct expression profiles of Notch-1 protein in human solid tumors: Implications for development of targeted therapeutic monoclonal antibodies", Biologics: Targets & Therapy 4(24):163-171 (2010).

Mumm et al. "A Ligand-Induced Extracellular Cleavage Regulates γ-Secretase-like Proteolytic Activation of Notch1". Molecular Cell 5, 197-206 (2000).
Nakatsu et al, "Angiogenic sprouting and capillary lumen formation modeled by human umbilical vein endothelial cells (HUVEC) in fibrin gels: the role of fibroblasts and Angiopoietin-1", Microvascular Research 66:102-112 (2003).
Nam et al, "Notch signaling as a therapeutic target", Current Opinion in Chemical Biology 6:501-509 (2002).
PCT International Search Report and Written Opinion for International Patent Application No. PCT/IB2011/055411 issued Mar. 5, 2012.
PCT International Search Report and Written Opinion for International Patent Application No. PCT/IB2011/055595 issued Jul. 13, 2012.
PCT Written Opinion for PCT/IB2010/052711 issued Dec. 18, 2011.
Ploscariu et al., "Single molecule studies of force-induced S2 site exposure in the Mammalian notch negative regulatory domain", J. Phys. Chem. B, May 8;118(18):4761-70 (2014).
Radtke et al, "The Role of Notch in Tumorigenesis: Oncogene or Tumour Suppressors?", Nature Reviews—Cancer 3:756-767 (2003).
Rand et al, "Calcium Depletion Dissociates and Activates Heterodimeric Notch Receptors", Molecular and Cellular Biology 20(5):1825-1835 (2000).
Ridgway et al, "Inhibition of Dll4 signalling inhibits tumour growth by deregulating angiogenesis", Nature 444:1083-1087 (2006).
Roy et al, "The multifaceted role of Notch in cancer", Current Opinion in Genetics & Development 17:52-59 (2007).
Said et al, "Involucrin in Lung Tumors: A Specific Marker for Squamos Differentiation", Laboratory Investigation 49(5):563-568 (1983).
Schroeter et al. "Notch-1 signaling requires ligand-induced proteolytic release of intracellular domain". Nature 393(6683):382-386 (1998).
Stephenson et al., "Direct observation of proteolytic cleavage at the S2 site upon forced unfolding of the Notch negative regulatory region", Proc. Natl. Acad. Sci. U S A., Sep. 24;109(41):E2757-65 (2012).
Tiyanont et al., "Insights into Notch3 activation and inhibition mediated by antibodies directed against its negative regulatory region", J. Mol. Biol., 9;425(17):3192-204 (2012).
van Es et al, "Notch/γ-secretase inhibition turns proliferative cells in intestinal crypts and adenomas into goblet cells", Nature 435:959-963 (2005).
Weng et al, "Activating Mutations of NOTCH1 in Human T Cell Acute Lymphoblastic Leukemia", Science 306(#5694):269-271 (2004).

* cited by examiner

FIG. 5

N1 is SEQ ID NO: 37
N2 is SEQ ID NO: 38

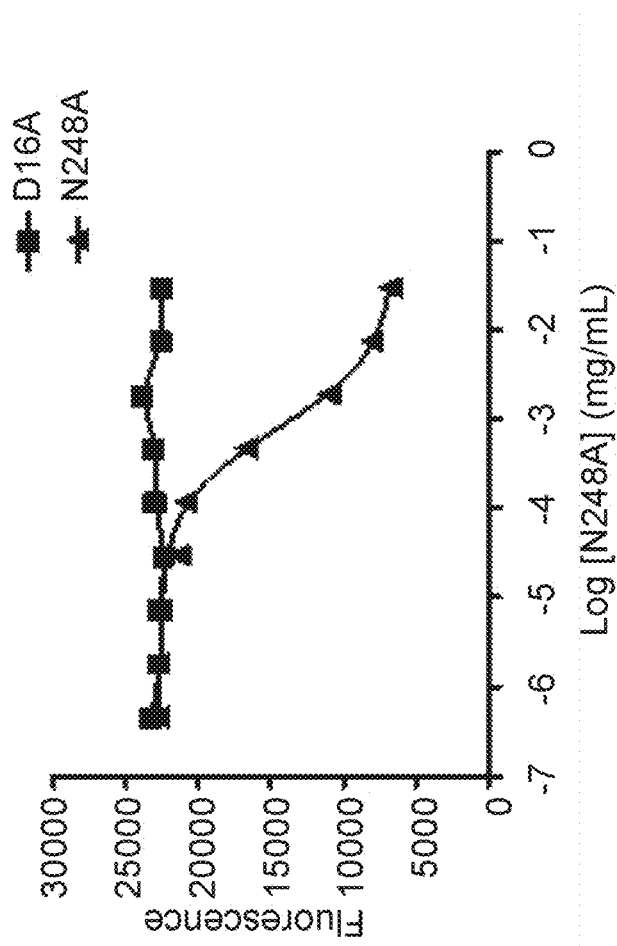
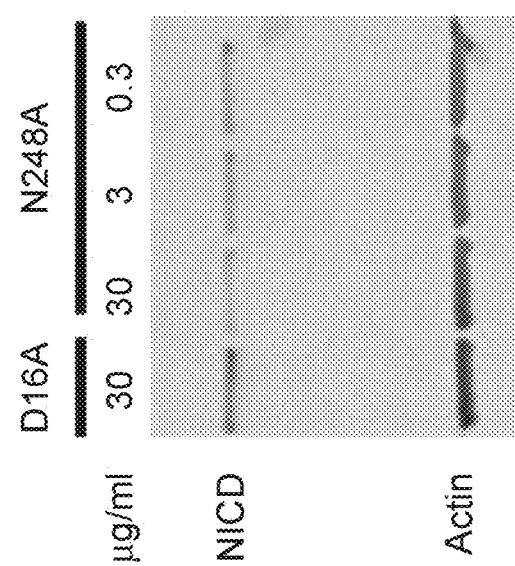
FIG. 6A
FIG. 6B

000
ANTI NOTCH-1 ANTIBODIES

CROSS REFERENCE TO RELATED APPLICATIONS

The present application is a National Stage submission under 35 U.S.C. §371 from International Application No. PCT/ IB2010/052711, filed Jun. 16, 2010, and claims the benefit of priority of U.S. Provisional Patent Application No. 61/218,193, filed Jun. 18, 2009, the disclosure of which is incorporated herein by reference in its entirety.

REFERENCE TO SEQUENCE LISTING

This application is being filed electronically via EFS-Web and includes an electronically submitted sequence listing in .txt format. The .txt file contains a sequence listing entitled "PC33897B_Seq_Listing_ST25.txt" created on Jun. 9, 2010 and having a size of 20.0 KB. The sequence listing contained in this .txt file is part of the specification and is herein incorporated by reference in its entirety.

FIELD OF THE INVENTION

The present invention relates to antibodies that antagonize the activity of Notch-1, method of producing such antibodies, method of assaying such antibodies and method of using such antibodies in the treatment of cancer.

BACKGROUND

Notch proteins are transmembrane receptor proteins. There are four such notch receptors in mammals. During receptor maturation, the ectodomains of mammalian notch receptors are cleaved at a $S_1$ site by a furin-like protease, yielding an extracellular subunit and a transmembrane subunit that are held together by a heterodimerization (HD) domain. The part of HD domain associated with extracellular subunit is referred to as HD-N, and the other part of HD, extracellular moiety of transmembrane subunit, referred to as HD-C. The extracellular subunit contains a large epidermal growth factor (EGF)-like repeat region and three Lin12 repeats. Ligand binding of the EGF-repeat regions induces a proteolytic cleavage by ADAM-type metalloprotease at the $S_2$ site within the HD-C domain, which triggered subsequent cleavage by γ-secretase at site $S_3$ releases the intracellular part of notch from the membrane, allowing it to move into the nucleus and regulate gene transcription. (Gordon, W. R., et.al, Nature Structural &Molecular Biology, 2007, volume 14, 295-300).

Before ligand induced activation, notch is maintained in a resting metalloprotease-resistant confirmation by a conserved negative regulation region (NRR), which consists of the three Lin12 repeats and the HD domain. (Vardar et al., Biochemistry 2003, 41: 7061-7067; Sanchez-Irizarry et al., Mol. Cell. Biol. 2004, 24: 9265-9273; Gordon, W. R., et.al, Nature Structural &Molecular Biology, 2007, volume 14, 295-300). NRR of the notch proteins is also sometimes defined as only consisting the Lin12 repeats and the N terminal HD domain (HD-N) after proteolytic cleavage at the $S_1$ site. (Weng, A. P., et. al, Science, 2004, 9265-9273.) NRR domain prevents the ligand-independent proteolysis of the notch pathway.

The Notch pathways functions during diverse developmental and physiological process including those affecting neurogenesis in flies and vertebrates. In general, notch signaling is involved in lateral inhibition, lineage decisions, and the establishment of boundaries between groups of cells. (Bray, S. J., Nature Reviews, 2006, 678-688).

However, notch activities are also associated with a variety of human diseases, including cancer. For example, mutations of notch1 were detected in more than 50% of T-cell acute lymphoblastic leukemia. (Radtke, F, Nature Review, Cancer, 2003, 756-767). There is a need in identifying therapeutic agents that regulate the notch-1 signaling pathway for the use of treating cancer.

SUMMARY

In one embodiment, this invention provides an isolated antibody, or an antigen binding portion thereof, that binds to Notch-1, wherein the antibody or antigen binding portion binds to at least a first epitope and a second epitope, wherein the first epitope resides within the Lin-A domain of Notch-1, and the second epitope resides within the HD-C domain of Notch-1. Preferably, the Notch-1 is human Notch-1.

In one aspect of this embodiment, the first epitope is a major epitope. Preferably, a non conservative substitution of any of the amino acid residues of the first epitope results in the loss of more than 60%, more preferably more than 80%, even more preferably more than 90% of the antibody or antigen binding portion's binding affinity to human Notch1.

In another aspect, the second epitope is a major epitope. Preferably, a non conservative substitution of any of the amino acid residues of the second epitope results in the loss of more than 60%, more preferably more than 80%, even more preferably more than 90% of the antibody or antigen binding portion's binding affinity to human Notch-1.

In another aspect, both the first epitope and the second epitope are major epitopes. Preferably, a non conservative substitution of any of the amino acid residues of the first epitope and the second epitope results in the loss of more than 60%, more preferably more than 80%, even more preferably more than 90% of the antibody or antigen binding portion's binding affinity to human Notch-1.

In another aspect of this embodiment, the Notch-1 is human Notch-1. In another aspect of this embodiment, the Notch-1 is mouse Notch-1.

In another aspect of this embodiment, the antibody or the antigen binding portion binds to an additional 1-4 epitopes, wherein each of the said additional epitopes resides within either the Lin-A domain or HD-C domain of human Notch-1.

In another aspect of this embodiment, the only major epitopes that the antibody or antigen binding portion binds to are the first epitope and the second epitope. More specifically, the first epitope is a major epitope comprising 1 to 4 amino acid residues selected from 1463V, 1465S, 1466L and 1467Q of the LinA domain of human Notch-1. Preferably, the first epitope is a major epitope consisting the four amino acid residues selected from 1463V, 1465S, 1466L and 1467Q of the LinA domain of human Notch-1. Also more specifically, the second epitope is a major epitope comprising of 1 to 5 amino acid residues selected from 1705G, 1706A, 1707L, 1709S and 1710L of the HD-C domain of human Notch-1. Preferably, the second epitope is a major epitope consisting of 1 to 5 amino acid residues selected from 1705G, 1706A, 1707L, 1709S and 1710L of the HD-C domain of human Notch-1. Even more specifically, a non conservative substitution of any of the amino acid residues of the first epitope or the second epitope results in a loss of more than 70%, more than 80%, more than 90% or more than 95% of the antibody or antigen binding portion's binding affinity to human Notch-1.

In another aspect of this embodiment, the antibody or the antigen binding portion is humanized, human, or chimeric. Preferably, the antibody or the antigen binding portion is a humanized antibody or antigen binding portion thereof. More preferably, the antibody or the antigen binding portion is a human antibody or antigen binding portion thereof.

In another aspect of this embodiment, the antibody or the antigen binding portion is a mouse antibody or antigen binding portion thereof.

In another aspect of this embodiment, the antibody or the antigen binding portion binds to human Notch-1 with a $K_D$ of $1\times10^{-5}$ M or less. Preferably, the antibody or the antigen binding portion binds to human Notch-1 with a $K_D$ of $1\times10^{-6}$ M or less, $5\times10^{-7}$M or less, $2\times10^{-7}$M or less, $1\times10^{-7}$M or less, $5\times10^{-8}$M or less, $2\times10^{-8}$M or less or $1\times10^{-8}$M or less.

In another embodiment, this invention provides an isolated antibody, or an antigen binding portion thereof, that specifically binds to human Notch-1, comprising (i) a heavy chain variable region CDR1 comprising the amino acid sequence shown in SEQ ID NO:18, or a variant thereof in which 1-4 residues of SEQ ID NO:18 are modified, preferably, only 3 residues are modified, more preferably, only two residues are modified, even more preferably, only one residue is modified;

(ii) a heavy chain variable region CDR2 comprising the amino acid sequence shown in SEQ ID NO:19, or a variant thereof in which 1-4 residues of SEQ ID NO: 19 are modified, preferably, only 3 residues are modified, more preferably, only two residues are modified, even more preferably, only one residue is modified; and (iii) a heavy chain variable region CDR3 having the amino acid sequence shown in SEQ ID NO:20, or a variant thereof in which 1-4 residues of SEQ ID NO: 20 are modified, preferably, only 3 residues are modified, more preferably, only two residues are modified, even more preferably, only one residue is modified.

In one aspect of this embodiment, of the 12 possible amino acid residue modifications (as described above in this embodiment) of the heavy chain variable regions CDR1, CDR2 and CDR3, any of the modifications, except for up to six of the modifications, is a conservative substitution of the amino acid residue thereof. Preferably, any of the said modifications of the heavy chain variable regions CDR1, CDR2 and CDR3, except for up to five of the modifications, is a conservative substitution of the amino acid residue thereof. More preferably, any of the said modifications of the heavy chain variable regions CDR1, CDR2 and CDR3, except for up to four of the modification, except for up to three of the modifications, except for up to two of the modifications or except for one modification, is a conservative substitution of the amino acid residue thereof. Even more preferably, any of the amino acid residue modification of the heavy chain variable regions CDR1, CDR2 and CDR3, is a conservative substitution of the amino acid residue thereof.

In another aspect of this embodiment, none of the heavy chain variable region CDR1, CDR2 and CDR3 is modified.

In another embodiment, this invention provides an isolated antibody, or an antigen binding portion thereof, that specifically binds to Notch-1, comprising (i) a light chain variable region CDR1 comprising the amino acid sequence shown in SEQ ID NO:12, or a variant thereof in which 1-4 residues of SEQ ID NO:12 is modified, preferably, only 3 residues are modified, more preferably, only two residues are modified, even more preferably, only one residue is modified;

(ii) a light chain variable region CDR2 comprising the amino acid sequence shown in SEQ ID NO:13, or a variant thereof in which 1-4 residues of SEQ ID NO:13 is modified, preferably, only 3 residues are modified, more preferably, only two residues are modified, even more preferably, only one residue is modified; and (iii) a light chain variable region CDR3 comprising the amino acid sequence shown in SEQ ID NO:14, or a variant thereof in which 1-4 residues of SEQ ID NO: 14 is modified, preferably, only 3 residues are modified, more preferably, only two residues are modified, even more preferably, only one residue is modified.

In one aspect of this embodiment, of the 12 possible amino acid residue modifications (as described above in this embodiment) of the light chain variable regions CDR1, CDR2 and CDR3, any of the modifications, except for up to six of the modifications, is a conservative substitution of the amino acid residue thereof. Preferably, any of the said modifications of the light chain variable regions CDR1, CDR2 and CDR3, except for up to five of the modifications, is a conservative substitution of the amino acid residue thereof. More preferably, any of the said modifications of the light chain variable regions CDR1, CDR2 and CDR3, except for up to four of the modification, except for up to three of the modifications, except for up to two of the modifications or except for one modification, is a conservative substitution of the amino acid residue thereof. Even more preferably, any of the said modifications of the light chain variable regions CDR1, CDR2 and CDR3 is a conservative substitution of the amino acid residue thereof.

In another aspect of this embodiment, none of the light chain variable region CDR1, CDR2 and CDR3 is modified.

In another embodiment, this invention provides an isolated antibody, or an antigen binding portion thereof, that specifically binds to Notch-1, comprising:

(i) a heavy chain variable region CDR1 comprising SEQ ID NO: 18, or a variant thereof in which 1-4 residues of SEQ ID NO:18 are modified, preferably, only 3 residues are modified, more preferably, only two residues are modified, even more preferably, only one residue is modified;

(ii) a heavy chain variable region CDR2 comprising SEQ ID NO: 19, or a variant thereof in which 1-4 residues of SEQ ID NO:19 are modified, preferably, only 3 residues are modified, more preferably, only two residues are modified, even more preferably, only one residue is modified;

(iii) a heavy chain variable region CDR3 comprising SEQ ID NO: 20, or a variant thereof in which 1-4 residues of SEQ ID NO:20 are modified, preferably, only 3 residues are modified, more preferably, only two residues are modified, even more preferably, only one residue is modified;

(iv) a light chain variable region CDR1 comprising SEQ ID NO: 12, or a variant thereof in which 1-4 residues of SEQ ID NO:12 are modified, preferably, only 3 residues are modified, more preferably, only two residues are modified, even more preferably, only one residue is modified;

(v) a light chain variable region CDR2 comprising SEQ ID NO: 13, or a variant thereof in which 1-4 residues of SEQ ID NO:13 are modified, preferably, only 3 residues are modified, more preferably, only two residues are modified, even more preferably, only one residue is modified; and (vi) a light chain variable region CDR3 comprising SEQ ID NO: 14, or a variant thereof in which 1-4 residues of SEQ ID NO:14 are modified, preferably, only 3 residues are modified, more preferably, only two residues are modified, even more preferably, only one residue is modified.

In one aspect of this embodiment, of the 24 possible amino acid residue modifications (as described above in this embodiment) of the heavy chain variable regions CDR1, CDR2 and CDR3 and the light chain variable regions CDR1, CDR2 and CDR3, any of the modifications, except for up to 12 of the modifications, is a conservative substitution of the amino acid residue thereof. Preferably, any of the said modifications of the heavy chain variable regions CDR1, CDR2 and CDR3 and the light chain variable regions CDR1, CDR2 and CDR3, except for up to 11 of the modifications, is a conservative substitution of the amino acid residue thereof. More preferably, any of the said modifications of the heavy chain variable regions CDR1, CDR2 and CDR3 and the light chain variable regions CDR1, CDR2 and CDR3, except for up to 10 of the modifications, except for up to 9 of the modifications, except for up to 8 of the modifications, except for up to 7 of the modifications, except for up to 6 of the modifications, except for up to 5 of the modifications, except for up to four of the modification, except for up to three of the modifications, except for up to two of the modifications or except for one modification, is a conservative substitution of the amino acid residue thereof. Even more preferably, any of the said modifications of the heavy chain variable regions CDR1, CDR2 and CDR3 and the light chain variable regions CDR1, CDR2 and CDR3 is a conservative substitution of the amino acid residue thereof.

In another aspect of this embodiment, none of the light chain CDR and the heavy chain CDRs is modified.

In another embodiment, the inventions provides an isolated monoclonal antibody, or an antigen binding portion thereof, wherein the antibody or antigen binding portion cross-competes or competes for binding to human Notch-1, with an antibody that comprises:

(a) a heavy chain variable region comprising the amino acid sequence of SEQ ID NO:6; and (b) a light chain variable region comprising the amino acid sequence of SEQ ID NO:8.

In another embodiment, the inventions provides an isolated monoclonal antibody, or an antigen binding portion thereof, wherein the antibody or antigen binding portion cross-competes or competes for binding to human Notch-1, with an antibody that comprises:

(i) a heavy chain variable region CDR1 comprising SEQ ID NO: 18, (ii) a heavy chain variable region CDR2 comprising SEQ ID NO: 19, (iii) a heavy chain variable region CDR3 comprising SEQ ID NO: 20, (iv) a light chain variable region CDR1 comprising SEQ ID NO: 12, (v) a light chain variable region CDR2 comprising SEQ ID NO: 13, and (vi) a light chain variable region CDR3 comprising SEQ ID NO: 14, wherein 1-4 amino residues of each of the light chain CDR and the heavy chain CDR may be modified. Preferably, any of the modification of the light chain CDRs and the heavy chain CDRs is a conservative substitution of the amino acid residues thereof. More preferably, none of the light chain CDRs and the heavy chain CDRs is modified.

Determination of CDR regions is well within the skill of the art. It is understood that in some embodiments, CDRs can be a combination of the Kabat and Chothia CDR (also termed "combined CDRs" or "extended CDRs"). In some embodiments, the CDRs are the Kabat CDRs. In other embodiments, the CDRs are the Chothia CDRs. In other words, in embodiments with more than one CDR, the CDRs may be any of Kabat, Chothia, combination CDRs, or combinations thereof.

In one aspect of the embodiments, the antibody is a humanized antibody. In another aspect of the embodiments, the antibody is a fully human antibody. In another aspect of the embodiments, the antibody is a chimeric antibody.

In another aspect of the embodiments, the antibody or the antigen binding portion binds to human Notch-1 with an equilibrium dissociation constant $K_D$ of less than $1 \times 10^{-5}$ M, preferably less than $1 \times 10^{-8}$ M, preferably less than $5 \times 10^{-7}$ M, preferably less than $2 \times 10^{-7}$ M, preferably less than $1 \times 10^{-7}$ M, or even more preferably less than $1 \times 10^{-8}$ M.

In another aspect of the embodiments, the antibody is a mouse antibody. In another aspect of this embodiment, the antibody is humanized, human, or chimeric. Preferably, the antibody is humanized. More preferably, the antibody is fully human antibody.

In another aspect of this embodiment, the antibody is a human full length antibody of subclass $IgG_1$, $IgG_2$, $IgG_3$ or $IgG_4$. In another aspect of this embodiment, the antibody is a humanized antibody of subclass $IgG_1$, $IgG_2$, $IgG_3$ or $IgG_4$. In yet another embodiment, the antibody is a chimeric antibody of subclass $IgG_1$, $IgG_2$, $IgG_3$ or $IgG_4$.

In another embodiment, this invention provides a pharmaceutical composition comprising any of the antibodies or antigen binding portion disclosed herein.

In another embodiment, this invention provides a cell line that recombinantly produces the any of the antibodies or antigen binding portion disclosed herein.

In another embodiment, this invention provides an oligonucleotide encoding either the heavy chain or the light chain any of the antibodies or antigen binding portion disclosed herein.

In another embodiment, this invention provides a method for treating cancer comprising administering to the subject a therapeutically effective amount of the antibody or the antigen binding portion of the invention, or a pharmaceutical composition thereof.

In another embodiment, this invention provides the antibodies or the antigen binding portion disclosed herein for the use in the treatment of cancer.

In another embodiment, this invention provides the use of the antibodies or the antigen binding portion disclosed herein, for the preparation of a medicament for the treatment of cancer.

BRIEF DESCRIPTION OF THE FIGURES/DRAWINGS

Figure 4:
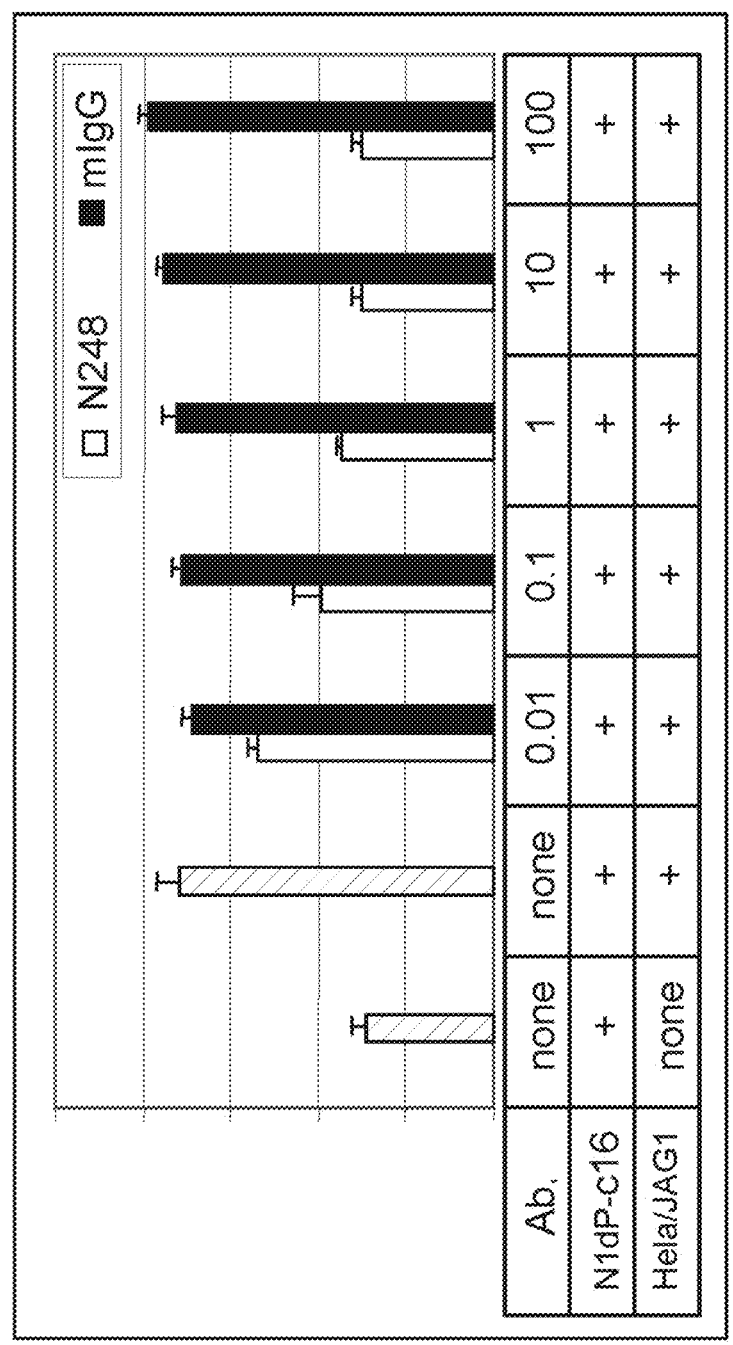

FIG. 4 illustrates that the luciferase reporter assay indicates that mAb N248A inhibit Jagged-1 induced Notch 1 signaling. Hela/Jagged1 cells and N1dP-c16 cells were co-cultured for the luciferase reporter assay. MIgG is a control mouse antibody. The y-axis numbers are luciferase reporter activity readings.

Figure 5:
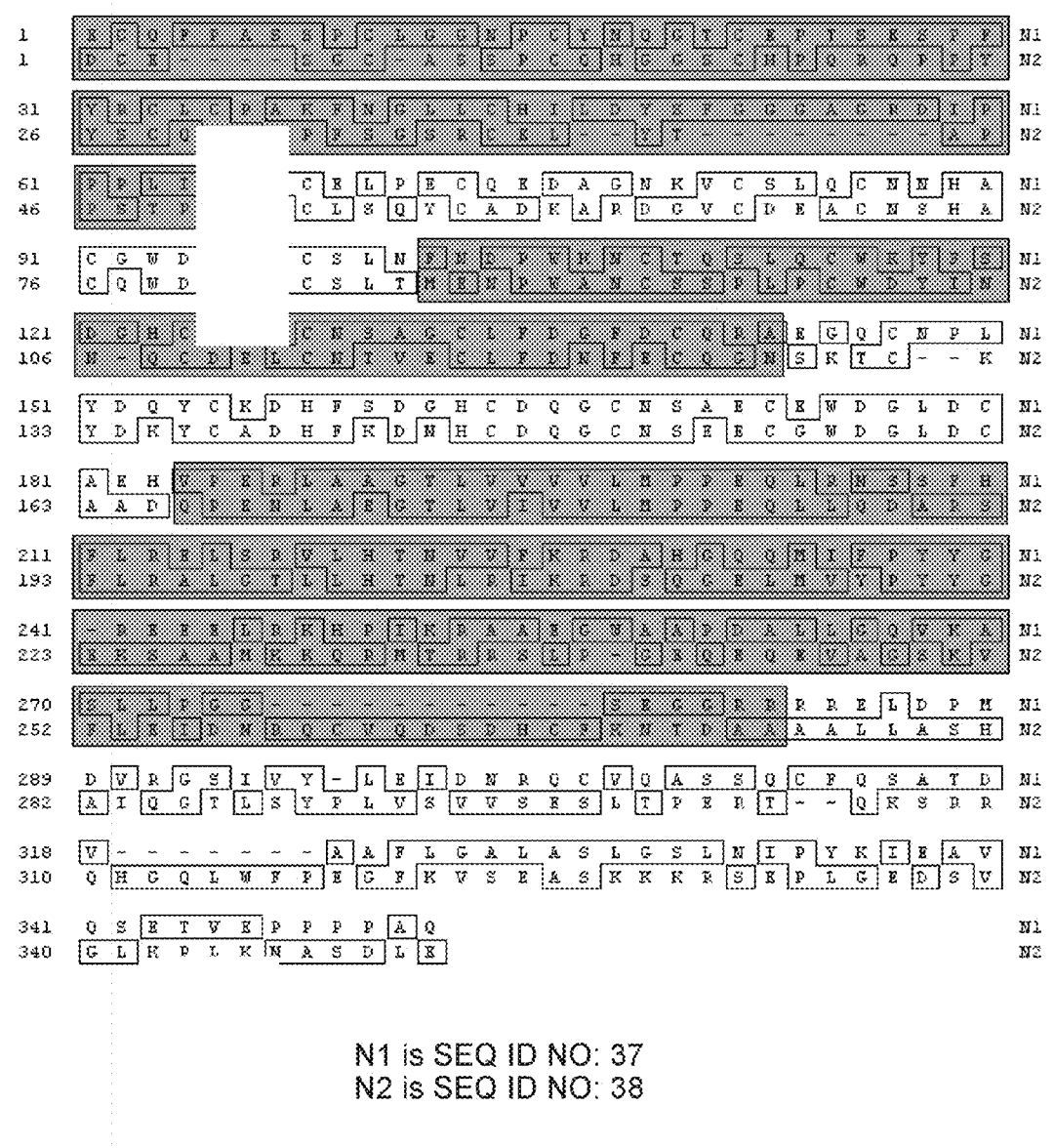

FIG. 5 is a sequence alignment of the EFG, Lin-A, Lin-B, Lin-C, HD-N and HD-C domains between human Notch1 and human Notch2.

FIG. 6A is a Western blot image illustrating that level of NICD (Notch1 intracellular domain) was reduced by mAb N248A in the HPB-ALL cells.

FIG. 6B illustrates that growth of HPB-All cells are inhibited by mAb N248A.

Figure 7A:
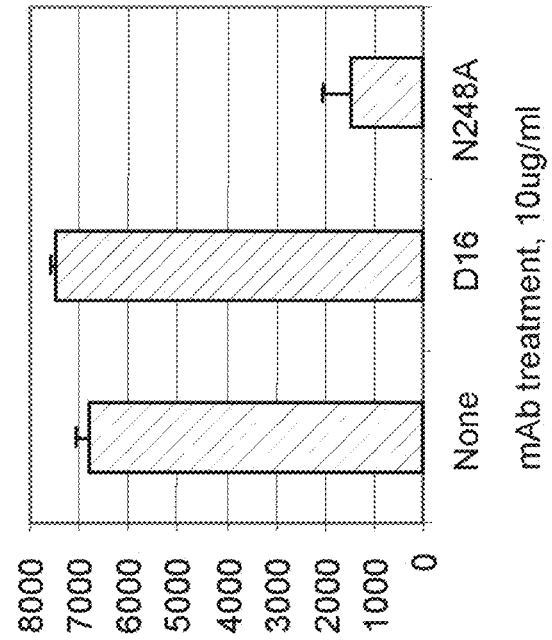
Figure 7B:
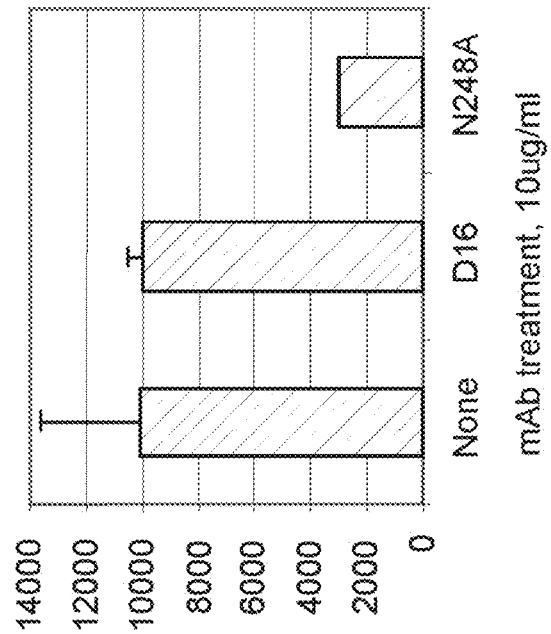

FIGS. 7A and 7B illustrates that mAb N248A blocks the expression of Hes1 mRNA and Hes4 mRNA respectively.

Figure 8:
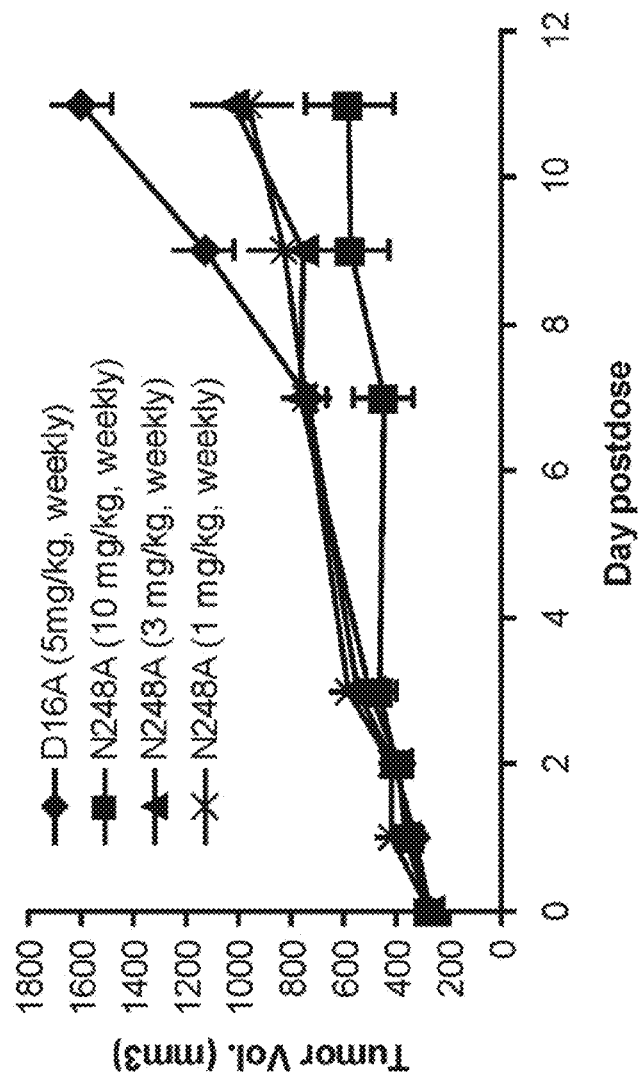

FIG. 8 illustrates the growth inhibition of HBP-ALL xenograft tumor by mAb N248A. Mice were dosed with mAb as indicated in the figure after tumor grew to 150-300 mm³. Each group contains ten mice with randomized tumor size.

Figure 9:
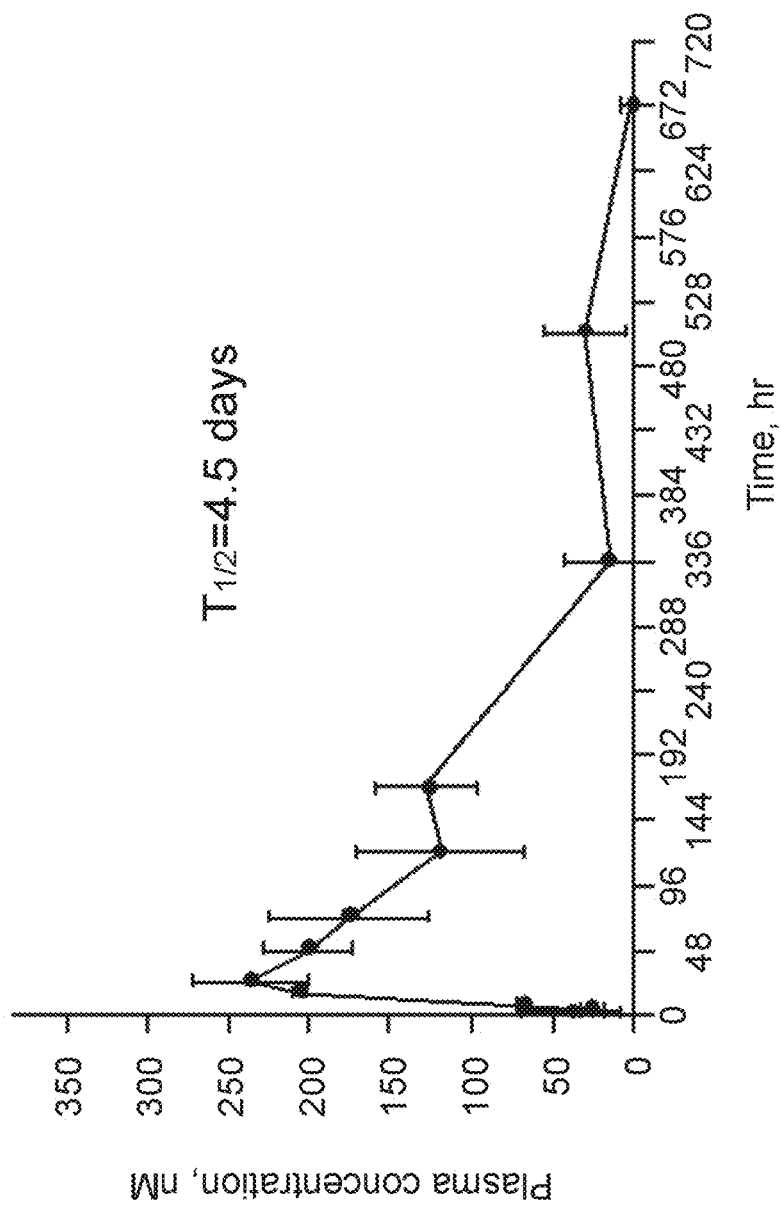

FIG. 9 illustrates the changes of plasma mAb N248A concentration after a single dose injection of 5 mg/kg in mice. Each data point was calculated based on three mice. $T_{1/2}$ is the half life of N248A in mouse sera.

Figure 10:
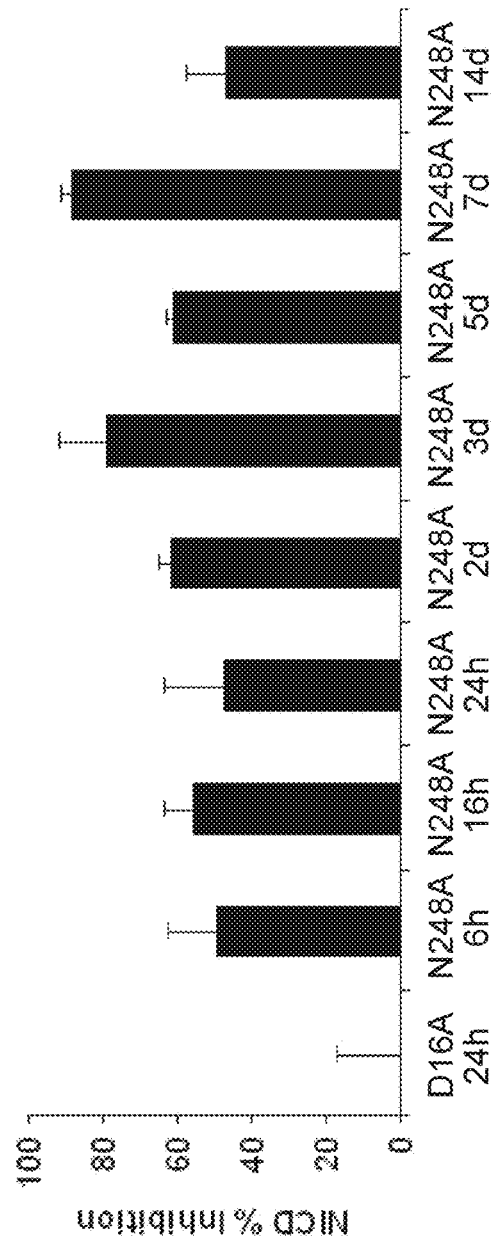

FIG. 10 illustrates the inhibition of NICD in HBP-ALL xenograft tumors after a single dose injection of 5 mg/kg in mice. The Western blot bands of the tumors treated with control antibody D16A were set as 100% intensity, which equals to 0% inhibition.

DETAILED DESCRIPTION OF THE INVENTION

The present disclosure relates to isolated monoclonal antibodies, particularly human monoclonal antibodies and mouse monoclonal antibodies as well as human/mouse chimeric antibodies that bind specifically to Notch-1 with high affinity. The disclosure provides isolated antibodies, methods of making such antibodies, immunoconjugates and bispecific molecules comprising such antibodies and pharmaceutical compositions containing the antibodies, immunoconjugates or bispecific molecules of the disclosure. The disclosure also relates to methods of using the antibodies, such as to inhibit Notch-1 activation, as well as to treat diseases associated with over activation or over expression of Notch-1, such as abnormal cell growth (e.g. cancer). Accordingly, the disclosure also provides methods of using the anti-Notch-1 antibodies or antigen binding portions thereof to treat various types of abnormal cell growth, such as cancer.

Definitions

The terms "Notch-1" or "Notch1" are used interchangeably, and include variants, isoforms and species homologs of human Notch-1 protein. Native human Notch-1 protein, for example, is made up of a leader peptide, a large epidermal growth factor (EGF)-like repeat region, three Lin12 repeats, a N terminal heterodimerization domain (HD-N), a C terminal heterodimerization domain (HD-C), a transmembrane (TM) sequence and an intracellular domain (NICD). The NCBI/GenBank accession number of the full length human Notch-1 is NM_017617.2

The term "Notch-1 negative regulatory region", or "Notch-1 NRR" as used herein, unless otherwise indicted, refers to any native or synthetic polypeptide region of Notch-1 consisting of the three Lin12 domains and the amino acid sequence or sequences located between the three Lin12 domains and the transmembrane domain of Notch-1. In one embodiment, the "Notch-1 NRR" includes the three Lin12 domains and two heterodimerization domains HD-N, and HD-C, wherein the HD-N and HD-C domains of Notch-1 are covalently bonded and not yet cleaved by the furin-like protease (before S1 cleavage). In another embodiment, the "Notch-1 NRR" includes the three Lin12 domains and the two heterodimerization domains HD-N, and HD-C, wherein the HD-N and HD-C domains are non-covalently bonded (after S1 cleavage). In one aspect of this embodiment, the S2 site within the HD-C domain has not been cleaved by the ADAM-type metalloproteases. In another particular aspect of this embodiment, the S2 site within the HD-C domain is being cleaved or has already been cleaved by the ADAM-type metalloproteases. (Gordon, W. R., et.al, Nature Structural & Molecular Biology, 2007, volume 14, 295-300).

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell. An example of a "cell surface receptor" of the present disclosure is the Notch-1 receptor.

The term "antibody" as referred to herein includes whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, referred to complementarily determining regions (CDR), interspersed with regions that are more conserved, referred to framework regions (FR). The CDR regions can be determined using the Kabat or Chothia numbering systems, both of which are well known to those of skill in the art. See, e.g. Kabat, E. A., et al. (1991) Sequences of Proteins of Immunological Interest, Fifth Edition, U.S. Department of Health and Human Services, NIH Publication No. 91-3242; Chothia and Lesk, J. Mol. Biol. 196:901-917 (1987). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen (e.g., Notch-1). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')₂ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments may be obtained using any suitable technique, including conventional techniques known to those with skill in the art, and the fragments may be screened for utility in the same manner as are intact antibodies.

An "isolated antibody", as used herein, is intended to refer to an antibody that is substantially free of other antibodies having different antigenic specificities (e.g., an isolated antibody that specifically binds Notch-1 is substantially free of antibodies that specifically bind antigens other than Notch-1). An isolated antibody that specifically binds Notch-1 may, however, have cross-reactivity to other antigens, such as Notch-1 molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

The terms "human antibody", or "fully human antibody", as used herein, are intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the disclosure or antigen binding portions thereof may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The terms "human monoclonal antibody" or "fully human monoclonal antibody" refer to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "human antibody derivatives" refers to any modified form of the human antibody, e.g., a conjugate of the antibody and another agent or antibody.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The term "compete", as used herein with regard to an antibody, refers to when a first antibody, or an antigen-binding portion thereof, competes for binding with a second antibody, or an antigen-binding portion thereof, where binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). For instance, cross-competing antibodies can bind to the epitope, or portion of the epitope, to which the antibodies as disclosed herein bind. Use of both competing and cross-competing antibodies is encompassed by the present disclosure. Regardless of the mechanism by which such competition or cross-competition occurs (e.g., steric hindrance, conformational change, or binding to a common epitope, or portion thereof, and the like), the skilled artisan would appreciate, based upon the teachings provided herein, that such competing and/or cross-competing antibodies are encompassed and can be useful for the methods disclosed herein.

As used herein, a "major epitope" refers to an epitope, wherein if any one of the amino acid residues of the epitope is replaced by an alanine or a non conservative substitution, the binding affinity of the antibody to the antigen which the epitope belongs to, is decreased by more than 50%.

As used herein, "isotype" or "class" refers to the antibody class (e.g., IgM or IgG) that is encoded by the heavy chain constant region genes. The constant domains of antibodies are not involved in binding to antigen, but exhibit various effector functions. Depending on the amino acid sequence of the heavy chain constant region, a given human antibody or immunoglobulin can be assigned to one of five major classes of immunoglobulins: IgA, IgD, IgE, IgG, and IgM. The structures and three-dimensional configurations of different classes of immunoglobulins are well-known. Of the various human immunoglobulin classes, only human IgG1, IgG2, IgG3, IgG4, and IgM are known to activate complement. Human IgG1 and IgG3 are known to mediate ADCC in humans.

As used herein, "subclass" refers to the further specification within an isotype of the heavy chain constant region gene, such as, for example, the IgG1, IgG2, IgG3, or IgG4 subclasses within the IgG isotype.

As used herein, the term "compound" or "pharmaceutical compound" includes antibodies, antigen-binding portions thereof, immunoconjugates, and bispecific molecules.

The phrases "an antibody recognizing an antigen" and "an antibody specific for an antigen" are used interchangeably herein with the term "an antibody which binds specifically to an antigen."

The terms "Fc receptor" or "FcR" are used to describe a receptor that binds to the Fc region of an antibody. For example, the FcR can be a native sequence human FcR. Furthermore, the FcR can be one that binds an IgG antibody (a gamma receptor) and includes receptors of the FcγRI, FcγRII, FcγRIII, and FcγRIV subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see, Daeron, *Annu. Rev. Immunol.*, 15:203-234 (1997)). FcRs are reviewed in Ravetch and Kinet, *Annu. Rev. Immunol.*, 9:457-92 (1991); Capel et al., *Immunomethods*, 4:25-34 (1994); and de Haas et al., *J. Lab. Clin. Med.*, 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *Immunol.*, 117:587 (1976) and Kim et al., *J. Immunol.*, 24:249 (1994)).

As used herein, an antibody that "specifically binds to human Notch-1" is intended to refer to an antibody that binds to human Notch-1 with a $K_D$ of $1 \times 10^{-5}$ M or less.

The term "$k_{on}$", as used herein, is intended to refer to the on-rate, or association rate of a particular antibody-antigen interaction, whereas the term "$k_{off}$" as used herein, is intended to refer to the off-rate, or dissociation rate of a particular antibody-antigen interaction. The term "$K_D$", as used herein, is intended to refer to the equilibrium dissociation constant, which is obtained from the ratio of $k_{off}$ to $k_{on}$ (i.e., $k_{off}/k_{on}$) and is expressed as a molar concentration (M). $K_D$ values for antibodies can be determined using methods well established in the art. One method for determining the $K_D$ of an antibody is by using surface plasmon resonance, typically using a biosensor system such as a Biacore® system.

As used herein, the term "high affinity" for an antibody refers to an antibody having a $K_D$ of $1 \times 10^{-6}$ M or less.

As used herein, the term "subject" includes any human or nonhuman animal. The term "nonhuman animal" includes all vertebrates, e.g., mammals and non-mammals, such as non-human primates, sheep, dogs, cats, horses, cows, chickens, amphibians, reptiles, etc.

Human Notch-1 Receptor

Human Notch1 cDNA encodes a protein of 2556 amino acid residues consisting of a leader peptide, 36 EGF-like repeats, negative regulatory region (NRR), a transmembrane (TM) sequence and an intracellular domain. (Vardar et al., Biochemistry 2003, 41: 7061-7067; Sanchez-Irizarry et al., Mol. Cell. Biol. 2004, 24: 9265-9273; Gordon, W. R., et.al, Nature Structural &Molecular Biology, 2007, volume 14, 295-300). The Notch-1 NRR starts from amino acid residue 1447 and ends at 1734. The Notch-1 NRR consists of LNR-A (Notch-1 AA residues 1447-1483), LNR-B (Notch-1 AA residues 1484-1525), LNR-C (Notch-1 AA residues 1526-1565), N-terminal heterodimerization domain (HD-N, Notch-1 AA residues 1566-1665) and C-terminal heterodimerization domain (HD-C, Notch-1 AA residues 1666 to 1734).

The antibodies of the disclosure are characterized by particular functional features or properties of the antibodies. For example, the antibodies bind specifically to human Notch-1 with a $K_D$ of $1 \times 10^{-5}$ M or less. Preferably, an antibody of the disclosure binds to Notch-1 with high affinity, for example with a $K_D$ of $1 \times 10^{-6}$ M or less, more preferably with a $K_D$ of $1 \times 10^{-7}$ M or less, even more preferably, with a $K_D$ or $1 \times 10^{-8}$ M or less.

Assays to evaluate the binding ability of the antibodies toward Notch-1 include, but are not limited to ELISAs, Western blots, RIAs, and flow cytometry analysis. The binding kinetics (e.g., binding affinity) of the antibodies also can be assessed by assays known in the art, such as by Biacore analysis.

Monoclonal Antibody mAb N248A.

One illustrative antibody of the disclosure is the mouse monoclonal antibody N248A, generated, isolated, tested and structurally characterized as described in Examples 1-3 and 8. Table 1 lists the amino acid sequences of various regions of mAb N248A and other sequences disclosed herein.

TABLE 1

| | Sequence | SEQ ID Number |
|---|---|---|
| Nucleotide sequence of immunogen Notch1-NRR-TM(-) | ATGCCGCCGCTCCTGGCACCTCTGCTCTGC<br>CTGGCACTGCTACCCGCTCTCGCTGCACGA<br>GGTCCGCGATGCTCCCAACCAGGTGAGACC<br>TGCCTGAATGGAGGTAAGTGTGAAGCAGCC<br>AATGGCACGTGCCTGTGCCTGGGCCCCTTC<br>ACGGGCCCCGAATGCCAGTTCCCGGCCAGC<br>AGCCCTGCCTGGGCGGCAACCCCTGCTAC<br>AACCAGGGGACCTGTGAGCCCACATCCGAG<br>AGCCCCTTCTACCGTTGCCTGTGCCCCGCCA<br>AATTCAACGGGCTCTTGTGCCACATCCTGGA<br>CTACAGCTTCGGGGGTGGGCCGGGCGCG<br>ACATCCCCCCGCCGCTGATCGAGGAGGCGT | 1 |

TABLE 1-continued

| Sequence | SEQ ID Number |
|---|---|
| GCGAGCTGCCCGAGTGCCAGGAGGACGCG<br>GGCAACAAGGTCTGCAGCCTGCAGTGCAAC<br>AACCACGCGTGCGGCTGGGACGGCGGTGAC<br>TGCTCCCTCAACTTCAATGACCCCTGGAAGA<br>ACTGCACGCAGTCTCTGCAGTGCTGGAAGTA<br>CTTCAGTGACGGCCACTGTGACAGCCAGTG<br>CAACTCAGCCGGCTGCCTCTTCGACGGCTTT<br>GACTGCCAGCGTGCGGAAGGCCAGTGCAAC<br>CCCCTGTACGACCAGTACTGCAAGGACCACT<br>TCAGCGACGGGCACTGCGACCAGGGCTGCA<br>ACAGCGCGGAGTGCGAGTGGGACGGGCTG<br>GACTGTGCGGAGCATGTACCCGAGAGGCTG<br>GCGGCCGGCACGCTGGTGGTGGTGGTGCT<br>GATGCCGCCGGAGCAGCTGCGCAACAGCTC<br>CTTCCACTTCCTGCGGGAGCTCAGCCGCGT<br>GCTGCACACCAACGTGGTCTTCAAGCGTGAC<br>GCACACGGCCAGCAGATGATCTTCCCCTACT<br>ACGGCCGCGAGGAGGAGCTGCGCAAGCAC<br>CCCATCAAGCGTGCCGCCGAGGGCTGGGCC<br>GCACCTGACGCCCTGCTGGGCCAGGTGAAG<br>GCCTCGCTGCTCCCTGGTGGCAGCGAGGGT<br>GGGCGGCGGCGGAGGGAGCTGGACCCCAT<br>GGACGTCCGCGGCTCCATCGTCTACCTGGA<br>GATTGACAACCGGCAGTGTGTGCAGGCCTC<br>CTCGCAGTGCTTCCAGAGTGCCACCGACGT<br>GGCCGCATTCCTGGGAGCGCTCGCCTCGCT<br>GGGCAGCCTCAACATCCCCTACAAGATCGA<br>GGCCGTGCAGAGTGAGACCGTGGAGCCGCC<br>CCCGCCGGCGCAGAAGCGCCGGCGGCAGC<br>ATGGCCAGCTCTGGTTCCCTGAGGGCTTCAA<br>AGTGTCTGAGGCCAGCAAGAAGAAGCGGCG<br>GGAGCCCCTCGGCGAGGACTCCGTGGGCCT<br>CAAGCCCCTGAAGAACGCTTCAGAC | |
| Amino acid sequence of immunogen Notch1-NRR-TM(-) | MPPLLAPLLCLALLPALAARGPRCSQPGETCL<br>NGGKCEAANGTCLCLGPFTGPECQFPASSPC<br>LGGNPCYNQGTCEPTSESPFYRCLCPAKFNG<br>LLCHILDYSFGGGAGRDIPPPLIEEACELPECQ<br>EDAGNKVCSLQCNNHACGWDGGDCSLNFND<br>PWKNCTQSLQCWKYFSDGHCDSQCNSAGCL<br>FDGFDCQRAEGQCNPLYDQYCKDHFSDGHC<br>DQGCNSAECEWDGLDCAEHVPERLAAGTLVV<br>VVLMPPEQLRNSSFHFLRELSRVLHTNVVFKR<br>DAHGQQMIFPYYGREEELRKHPIKRAAEGWAA<br>PDALLGQVKASLLPGGSEGGRRRRELDPMDV<br>RGSIVYLEIDNRQCVQASSQCFQSATDVAAFL<br>GALASLGSLNIPYKIEAVQSETVEPPPPAQKRR<br>RQHGQLWFPEGFKVSEASKKKRREPLGEDSV<br>GLKPLKNASD | 2 |
| Nucleotide sequence of immunogen Notch1-NRR-TM(+) | ATGCCTCCGCTCCTGGCACCTCTGCTCTGCC<br>TGGCACTGCTACCCGCTCTCGCTGCACGAG<br>GTCCGCGATGCTCCCAACCAGGTGAGACCT<br>GCCTGAATGGAGGTAAGTGTGAAGCAGCCA<br>ATGGCACGTGCCTGTGCCTGGGCCCCTTCA<br>CGGGGCCCCGAATGCCAGTTCCCGGCCAGCA<br>GCCCCTGCCTGGGCGGCAACCCCTGCTACA<br>ACCAGGGGACCTGTGAGCCCACATCCGAGA<br>GCCCCTTCTACCGTTGCCTGTGCCCCGCCAA<br>ATTCAACGGGCTCTTGTGCCACATCCTGGAC<br>TACAGCTTCGGGGTGGGGCCGGGCGCGA<br>CATCCCCCCGCCGCTGATCGAGGAGGCGTG<br>CGAGCTGCCCGAGTGCCAGGAGGACGCGG<br>GCAACAAGGTCTGCAGCCTGCAGTGCAACA<br>ACCACGCGTGCGGCTGGGACGGCGGTGACT<br>GCTCCCTCAACTTCAATGACCCCTGGAAGAA<br>CTGCACGCAGTCTCTGCAGTGCTGGAAGTAC<br>TTCAGTGACGGCCACTGTGACAGCCAGTGC<br>AACTCAGCCGGCTGCCTCTTCGACGGCTTTG<br>ACTGCCAGCGTGCGGAAGGCCAGTGCAACC<br>CCCTGTACGACCAGTACTGCAAGGACCACTT<br>CAGCGACGGGCACTGCGACCAGGGCTGCAA<br>CAGCGCGGAGTGCGAGTGGGACGGGCTGG<br>ACTGTGCGGAGCATGTACCCGAGAGGCTGG<br>CGGCCGGCACGCTGGTGGTGGTGGTGCTGA<br>TGCCGCCGGAGCAGCTGCGCAACAGCTCCT<br>TCCACTTCCTGCGGGAGCTCAGCCGCGTGC | 3 |

TABLE 1-continued

| | Sequence | SEQ ID Number |
|---|---|---|
| | TGCACACCAACGTGGTCTTCAAGCGTGACGC ACACGGCCAGCAGATGATCTTCCCCTACTAC GGCCGCGAGGAGGAGCTGCGCAAGCACCC CATCAAGCGTGCCGCCGAGGGCTGGGCCGC ACCTGACGCCCTGCTGGGCCAGGTGAAGGC CTCGCTGCTCCCTGGTGGCAGCGAGGGTGG GCGGCGGCGGAGGGAGCTGGACCCCATGG ACGTCCGCGGCTCCATCGTCTACCTGGAGAT TGACAACCGGCAGTGTGTGCAGGCCTCCTC GCAGTGCTTCCAGAGTGCCACCGACGTGGC CGCATTCCTGGGAGCGCTCGCCTCGCTGGG CAGCCTCAACATCCCCTACAAGATCGAGGCC GTGCAGAGTGAGACCGTGGAGCCGCCCCCG CCGGCGCAGCTGCACTTCATGTACGTGGCG GCGGCCGCCTTTGTGCTTCTGTTCTTCGTGG GCTGCGGGGTGCTGCTGTCC | |
| Amino acid sequence of immunogen Notch1-NRR-TM(+) | MPPLLAPLLCLALLPALAARGPRCSQPGETCL NGGKCEAANGTCLCLGPFTGPECQFPASSPC LGGNPCYNQGTCEPTSESPFYRCLCPAKFNG LLCHILDYSFGGGAGRDIPPPLIEEACELPECQ EDAGNKVCSLQCNNHACGWDGGDCSLNFND PWKNCTQSLQCWKYFSDGHCDSQCNSAGCL FDGFDCQRAEGQCNPLYDQYCKDHFSDGHC DQGCNSAECEWDGLDCAEHVPERLAAGTLVV VVLMPPEQLRNSSFHFLRELSRVLHTNVVFKR DAHGQQMIFPYYGREEELRKHPIKRAAEGWAA PDALLGQVKASLLPGGSEGGRRRRELDPMDV RGSIVYLEIDNRQCVQASSQCFQSATDVAAFL GALASLGSLNIPYKIEAVQSETVEPPPPAQLHF MYVAAAAFVLLFFVGCGVLLS | 4 |
| Nucleotide sequence of heavy chain variable region of mAb N248A | CAGGTTCAGCTGCAGCAGTCTGGAGCTGAG CTGATGAAGCCTGGGGCCTCAGTGAAGATAT CCTGCAAGGCTACTGGCTACACATTCAGTAA CTACTGGATGGAGTGGGTAAAGCAGAGGCC TGGACATGGCCTTGAGTGGATTGGAGAGATT TTACCTGGAAGGGGTAGAACTAACTACAATG AGAACTTCAAGGGCAAGGCCACATTCACTGC AGATACATCCTCCAACACAGTCTACATGCAA CTCAACAGCCTGACATCTGAGGACTCTGCCG TCTATTACTGTGCAAGATTCCACAGCTCGGC CTATTACTATACTATGGACTACTGGGGTCAAA GAACCTCGGTCACCGTCTCCTCA | 5 |
| Amino acid sequence of Heavy chain variable region of mAb N248A | QVQLQQSGAELMKPGASVKISCKATGYTFS<u>NY WMEW</u>VKQRPGHGLEWIG<u>EILPGRGRTNYNEN FKG</u>KATFTADTSSNTVYMQLNSLTSEDSAVYY CAR<u>FHSSAYYYTMDY</u>WGQRTSVTVSS | 6 |
| Nucleotide sequence of light chain variable region of mAb N248A | CAGGCTGTTGTGACTCAGGAATCTGCACTCA CCACATCACCTGGTGAAACAGTCACACTCAC TTGTCGCTCAAGTACTGGGGCTGTTACAACT AGTAACTATGCCAACTGGGTCCAAGAAAAAC CAGATCATTTATTCACTGGTCTAATAGGTGGT ACCAACAACCGAGCTCCAGGTATTCCTGCCA GATTCTCAGGCTCCCTGATTGGAGACAAGGC TGCCCTCACCATCACAGGGGCACAGACTGA GGATGAGGCAATATATTTCTGTGCTCTATGG TACAGCAACCACTGGGTGTTCGGTGGAGGA ACCAAACTGACTGTCCTA | 7 |
| Amino acid sequence of Light chain variable region of mAb N248A | QAVVTQESALTTSPGETVTLTC<u>RSSTGAVTTS NYAN</u>WVQEKPDHLFTGLIGG<u>TNNRAPG</u>IPARF SGSLIGDKAALTITGAQTEDEAIYFC<u>ALWYSNH WV</u>FGGGTKLTVL | 8 |
| Nucleotide sequence of light chain variable region CDR1 of mAb N248A | CGCTCAAGTACTGGGGCTGTTACAACTAGTA ACTATGCCAAC | 9 |

TABLE 1-continued

| | Sequence | SEQ ID Number |
|---|---|---|
| Nucleotide sequence of light chain variable region CDR2 of mAb N248A | GGTACCAACAACCGAGCTCCA | 10 |
| Nucleotide sequence of light chain variable region CDR3 of mAb N248A | GCTCTATGGTACAGCAACCACTGGGTG | 11 |
| Amino acid sequence of light chain variable region CDR1 of mAb N248A | RSSTGAVTTSNYAN | 12 |
| Amino acid sequence of light chain variable region CDR2 of mAb N248A | GTNNRAP | 13 |
| Amino acid sequence of light chain variable region CDR3 of mAb N248A | ALWYSNHWV | 14 |
| Nucleotide sequence of heavy chain variable region CDR1 of mAb N248A | AACTACTGGATGGAG | 15 |
| Nucleotide sequence of heavy chain variable region CDR2 of mAb N248A | GAGATTTTACCTGGAAGGGGTAGAACTAACTACAATGAGAACTTCAAGGGC | 16 |
| Nucleotide sequence of heavy chain variable region CDR3 of mAb N248A | TTCCACAGCTCGGCCTATTACTATACTATGGACTAC | 17 |
| Amino acid sequence of heavy chain variable region CDR1 of mAb N248A | NYWME | 18 |
| Amino acid sequence of heavy chain variable region CDR2 of mAb N248A | EILPGRGRTNYNENFKG | 19 |
| Amino acid sequence of heavy chain variable region CDR3 of mAb N248A | FHSSAYYYTMDY | 20 |
| Nucleotide sequence of human Notch-1 NRR (LinA, LinB Lin C, HD-N and HD-C) | GAGGAGGCGTGCGAGCTGCCCGAGTGCCAGGAGGACGCGGGCAACAAGGTCTGCAGCCTGCAGTGCAACAACCACGCGTGCGGCTGGGACGGCGGTGACTGCTCCCTCAACTTCAATGACCCCTGGAAGAACTGCACGCAGTCTCTGCAGTGCTGGAAGTACTTCAGTGACGGCCACTGTGACAGCCAGTGCAACTCAGCCGGCTGCCTCTTCGACGGCTTTGACTGCCAGCGTGCGGAAGGCCAGTGCAACCCCCTGTACGACCAGTACTGCAAGGACCACTTCAGCGACGGGCACTGCGACCAGGGCTGCAACAGCGCGGAGTGCGAGTGGGACGGGCTGGACTGTGCGGAGCATGTACCCGAGAGGCTGGCGGCCGGCACGCTGGTGGTGGTGGTGCTGATGCCGCCGGAGCAGCTGCGCAACAGCTCCTTCCACTTCCTGCGGGAGCTCAGCCGCGTGCTGCACACCAACGTGGTCTTCAAGCGTGACGCACACGGCCAGCAGATGATCTTCCCCTACTACGGCCGCGAGGAGGAGCTGCGCAAGCACCCCATCAAGCGTGCCGCCGAGGGCTGGGCCGCACCTGACGCCCTGCTGG | 21 |

TABLE 1-continued

| Sequence | SEQ ID Number |
|---|---|
| GCCAGGTGAAGGCCTCGCTGCTCCCTGGTG GCAGCGAGGGTGGGCGGCGGCGGAGGGAG CTGGACCCCATGGACGTCCGCGGCTCCATC GTCTACCTGGAGATTGACAACCGGCAGTGTG TGCAGGCCTCCTCGCAGTGCTTCCAGAGTG CCACCGACGTGGCCGCATTCCTGGGAGCGC TCGCCTCGCTGGGCAGCCTCAACATCCCCTA CAAGATCGAGGCCGTGCAGAGTGAGACCGT GGAGCCGCCCCCGCCGGCGCAG LinA, LinB, LinC, HD-N and HD-C are marked by alternating underline. | |
| Amino acid sequence of human Notch-1 NRR (LinA, LinB Lin C, HD-N and HD-C)  EEACELPECQEDAGNKVCSLQCNNHACGWD GGDCSLNFNDPWKNCTQSLQCWKYFSDGHC DSQCNSAGCLFDGFDCQRAEGQCNPLYDQY CKDHFSDGHCDQGCNSAECEWDGLDCAEHV PERLAAGTLVVVVLMPPEQLRNSSFHFLRELS RVLHTNVVFKRDAHGQQMIFPYYGREEELRKH PIKRAAEGWAAPDALLGQVKASLLPGGSEGGR RRRELDPMDVRGSIVYLEIDNRQCVQASSQCF QSATDVAAFLGALASLGSLNIPYKIEAVQSETV EPPPPAQ LinA, LinB, LinC, HD-N and HD-C are marked by alternating underline and grey shade. | 22 |

As shown in Example 4, mAb N248A has a $K_D$ of less than $0.33 \times 10^{-6}$ M.

As shown in Example 5, it was shown that mAb N248A binds at least two distinguishable Notch-1 epitopes, one epitope is within the Lin-A domain and the other epitope is within the HD-C domain.

As shown in Example 6, mAb N248A inhibits both T-cell acute lymphoblastic leukemia (T-ALL) and breast cancer cell growth in cell culture.

As shown in Example 7, mAb N248A also inhibits T-cell lymphoblastic leukemia in murine xenograft tumor model.

Anti Notch-1 Antibodies that Bind to at Least Two Distinguished Epitopes in Notch-1 Lin-A Domain and Notch-1 HD-C Domain.

It is within the contemplation of the current invention, that antibodies that bind to the Notch-1 Lin-A and HD-C domain with a high affinity will reduce Notch-1 signal transduction, and therefore may demonstrate biological activity in vitro and in vivo to inhibit cancer cell growth, in particular, T-ALL cancer cell growth. Such antibodies may be produced following general methods known to those of ordinary skill in the art. In one embodiment, such antibodies can be produced through immunization of a mouse with an immunogen comprising the Notch-1 LinA domain and the Notch-1 HD-C domain, as shown in Examples 1 and 2, followed by hybridoma cloning of the antibodies thus generated, and assaying the cloned antibodies by ELISA assay, as shown in Example 2. The Notch-1 binding affinity of the antibodies selected according to the ELISA assay can be measured on a surface plasma resonance Biacore 3000 instrument, as shown in Example 4.

The anti Notch-1 antibodies of the current invention, wherein the antibodies that bind to the Notch-1 LinA domain and Notch-1 HD-C domain can be produced by any other methods known in the art other than described in the above paragraph. The route and schedule of immunization of the host animal are generally in keeping with established and conventional techniques for antibody stimulation and production, as further described herein. General techniques for production of human and mouse antibodies are known in the art and/or are described herein.

Anti Notch-1 Antibodies Generated by Hybridoma Technologies.

It is within the contemplation of the current invention that that any mammalian subject including humans or antibody producing cells therefrom can be manipulated to serve as the basis for production of mammalian, including human, hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C. (1975) Nature 256:495-497 or as modified by Buck, D. W., et al., In Vitro, 18:377-381 (1982). Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the Notch-1 monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as a source of antibodies encompass all derivatives, progeny cells of the parent hybridomas that produce monoclonal antibodies specific for Notch-1, or a portion thereof.

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity, if present, can be removed, for example, by running the preparation over adsorbents made of the immunogen attached to a solid phase and eluting or releasing the desired antibodies off the immunogen. Immunization of a host animal with a human Notch-1, or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups, can yield a population of antibodies (e.g., monoclonal antibodies).

Humanization of Anti Notch-1 Antibodies Generated by Immunization in a Host Animal.

It is within the contemplation of the current invention that anti Notch-1 antibodies of the invention wherein the antibodies are generated by immunization in a host animal can be manipulated in many ways to increase its biological activity and pharmaceutical properties. One way of such manipulation is humanization.

There are four general steps to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; 6,331,415; 5,530,101; 5,693,761; 5,693,762; 5,585,089; and 6,180,370.

A number of "humanized" antibody molecules comprising an antigen-binding site derived from a non-human immunoglobulin have been described, including chimeric antibodies having rodent or modified rodent V regions and their associated CDRs fused to human constant domains. See, for example, Winter et al. Nature 349:293-299 (1991), Lobuglio et al. Proc. Nat. Acad. Sci. USA 86:4220-4224 (1989), Shaw et al. J. Immunol. 138:4534-4538 (1987), and Brown et al. Cancer Res. 47:3577-3583 (1987). Other references describe rodent CDRs grafted into a human supporting framework region (FR) prior to fusion with an appropriate human antibody constant domain. See, for example, Riechmann et al. Nature 332:323-327 (1988), Verhoeyen et al. Science 239: 1534-1536 (1988), and Jones et al. Nature 321:522-525 (1986). Another reference describes rodent CDRs supported by recombinantly engineered rodent framework regions. See, for example, European Patent Publication No. 0519596. These "humanized" molecules are designed to minimize unwanted immunological response toward rodent anti-human antibody molecules which limits the duration and effectiveness of therapeutic applications of those moieties in human recipients. For example, the antibody constant region can be engineered such that it is immunologically inert (e.g., does not trigger complement lysis). See, e.g. PCT Publication No. PCT/GB99/01441; UK Patent Application No. 9809951.8. Other methods of humanizing antibodies that may also be utilized are disclosed by Daugherty et al., Nucl. Acids Res. 19:2471-2476 (1991) and in U.S. Pat. Nos. 6,180, 377; 6,054,297; 5,997,867; 5,866,692; 6,210,671; and 6,350, 861; and in PCT Publication No. WO 01/27160.

Human Anti Notch-1 Antibodies.

It is within the contemplation of the current invention that fully human anti Notch-1 antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Abgenix, Inc. (Fremont, Calif.) and HuMAb-Mouse® and TC Mouse™ from Medarex, Inc. (Princeton, N.J.).

It is also within the contemplation of the current invention that fully human anti Notch-1 antibodies may be obtained recombinantly following general methods of phage display technology. See, for example, U.S. Pat. Nos. 5,565,332; 5,580,717; 5,733,743; and 6,265,150; and Winter et al., Annu. Rev. Immunol. 12:433-455 (1994).

Alternatively, the phage display technology (McCafferty et al., Nature 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for review see, e.g., Johnson, Kevin S, and Chiswell, David J., Current Opinion in Structural Biology 3:564-571 (1993). Several sources of V-gene segments can be used for phage display. Clackson et al., Nature 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Mark et al., J. Mol. Biol. 222:581-597 (1991), or Griffith et al., EMBO J. 12:725-734 (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling." (Marks et al., Bio/Technol. 10:779-783 (1992)). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM-nM range. A strategy for making very large phage antibody repertoires (also known as "the mother-of-all libraries") has been described by Waterhouse et al., Nucl. Acids Res. 21:2265-2266 (1993).

Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen-binding site, i.e., the epitope governs (imprints) the choice of partner. When the process is repeated in order to replace the remaining rodent V domain, a human antibody is obtained (see PCT Publication No. WO 93/06213). Unlike traditional humanization of rodent antibodies by CDR grafting, this technique provides completely human antibodies, which have no framework or CDR residues of rodent origin.

Although the above discussion pertains to humanized and human antibodies, the general principles discussed are applicable to customizing antibodies for use, for example, in dogs, cats, primate, equines and bovines. One or more aspects of humanizing an antibody described herein may be combined, e.g., CDR grafting, framework mutation and CDR mutation. Engineered and Modified Anti Notch-1 Antibodies Made Recombinantly.

In general, antibodies may be made recombinantly by placing the DNA sequences of the desired antibody into expression vectors followed by transfection and expression in host cells, including but not limited to E. coli cells, simian COS cells, Chinese hamster ovary (CHO) cells, or myeloma cells that do not otherwise produce immunoglobulin protein. PCT Patent Publication No. WO 87/04462. Other host cells, such as transgenic plant cells or transgenic milk cells may also be used. See, for example, Peeters, et al. Vaccine 19:2756 (2001); Lonberg, N. and D. Huszar Int. Rev. Immunol 13:65 (1995); and Pollock, et al., J Immunol Methods 231:147 (1999).

An antibody may also be modified recombinantly. For example, the DNA of the human heavy and light chain constant regions may be used in place of the homologous murine sequences of the murine antibody DNA, Morrison et al., Proc. Nat. Acad. Sci. 81:6851 (1984), or by covalently joining to the immunoglobulin coding sequence all or part of the coding sequence for a non-immunoglobulin polypeptide. In similar manner, "chimeric" or "hybrid" antibodies can be prepared that have the binding specificity of an anti Notch-1 monoclonal antibody herein.

Antibody variable regions can also be modified by CDR grafting. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 332:323-327; Jones, P. et al. (1986) Nature 321:522-525; Queen, C. et al. (1989) Proc. Natl. Acad. See. U.S.A. 86:10029-10033; U.S. Pat. No. 5,225, 539 to Winter, and U.S. Pat. Nos. 5,530,101; 5,585,089; 5,693,762 and 6,180,370 to Queen et al.)

Accordingly, another aspect of the disclosure pertains to an isolated monoclonal antibody, or antigen binding portion thereof, comprising a heavy chain variable region comprising CDR1, CDR2, and CDR3 sequences comprising an amino acid sequence selected from the group consisting of SEQ ID NOs: 18, 19 and 20, respectively, and a light chain variable region comprising CDR1, CDR2, and CDR3 sequences comprising an amino acid sequence selected from the group consisting of SEQ ID NOs: 12, 13 and 14 respectively. Thus, such antibodies contain the $V_H$ and $V_L$ CDR sequences of the monoclonal antibodies N248A, yet may contain different framework sequences from these antibodies. Such framework sequences can be obtained from public DNA databases or published references that include germline antibody gene sequences.

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein. Typically, conservative modifications (as discussed below) are introduced. The mutations may be amino acid substitutions, additions or deletions. Moreover, typically no more than one, two, three, four or five residues within a CDR region are altered.

Conservative substitution and antibody affinity maturation will be discussed in more details in later paragraphs.
Mapping of Antigen Epitopes that an Antibody Binds to.

The binding epitopes of monoclonal antibodies on an antigen may be mapped by a number of methods depending on the type of antigen-antibody interactions.

If an antibody binds to a single epitope consisting of sequential amino acid residues in an antigen, whose binding usually is not affected by antigen conformational changes, the binding epitope is called a linear epitope. A peptide scanning method is commonly used to identify linear binding epitopes (see Journal of Immunological Methods, Volume 315, Issues 1-2, pages 11-18, August 2006), which requires synthesizing a series of overlapping 10-15mer peptides that cover the entire length of the antigen sequence. The peptides are arrayed on a protein-cross-linking membrane in duplicate dotted format. Antibody binding affinity to the peptide array is analyzed similar to ELISA. The peptides-arrayed membrane is first incubated in 1×PBST with 5% fetal calf serum to block nonspecific binding, then incubated with testing antibodies or nonspecific control antibody followed by incubation with HRP-labeled secondary antibody. The antibody binding strength is read out using a chemiluminescence imaging instrument.

Alternatively, a linear binding epitope may be identified using antigen protein domains displayed on yeast cell surface (see Journal of Molecular Biology, 365(1), 196-200, January 2007) or using antigen protein fragments displayed on bacterial cell surface (see FEMS Microbiol. Lett., 226(2), 347-353, September, 2003; also see Nature Methods, 5(12), 1039-1045, November 2008), followed by flow-cytometric sorting or FACS.

Limited proteolysis of peptide antigen and antibody complex, combined with mass spectrometry, may provide another approach to locate linear binding epitopes (see Methods Mol. Biol., 524, 87-101, 2009). Antigen and antibody are mixed and incubated at appropriate conditions to form a binding complex, which is digested by protease under controlled temperature and time. The bound reaction mixture is then passed through a protein-A affinity column to retain the antibody bound with an antigen epitope fragment, which is analyzed by mass spectrometry after eluted from the column.

Mapping of conformational epitopes depends on the interaction of antibody to antigen in its native conformation. A number of techniques have been reported useful in determining conformational epitopes. One of the methods commonly used is amino acid mutagenesis. Individual amino acid residues in the antigen protein speculated to bind with the antibody are mutated, and the mutated antigen protein is then expressed and subjected to antibody binding analysis to determine if the binding affinity is impaired. However, systematic amino acid mutagenesis across the complete antigen protein sequence is laborious. To narrow down the regions of antigen protein that interact with antibody, substitution of an individual antigen domain by a closely related protein domain can be a useful method (see J. Biol. Chem., 274 (14) 9617-9626, April 1999).

Shotgun mutagenesis mapping was developed to overcome the shortcomings of conventional amino acid mutagenesis (see J. American Chem. Soc, 131, 6952-6954, 2009). This method utilizes a comprehensive mutation library made from antigen cDNA, with each plasmid clone containing a unique point mutation and the entire mutation library covering every amino acid of the antigen coding region. The library of plasmid clones are transfected in HEK-293T or other human cells, and the cells are then arrayed in 384-well microplates. Antibody binding activity is assayed after fixation of cells on the microplate. If amino acid mutations caused a loss of reactivity, it is identified as an antibody binding epitope.

Cocrystallization of antigen-antibody complex, X-ray diffraction and structural analysis gives direction visualization of antigen-antibody interaction. When combined with amino acid mutagenesis, the technologies would provide powerful evidence and vivid picture for antibody binding epitopes. However, cocrystallization and structural analysis are technically challenging, requires large quantity of purified antigen and antibody, and can be a time-consuming trial and error process.

In order to make an anti Notch-1 antibody that binds to a epitope or a specified set of epitopes, one can generate anti Notch-1 antibodies, then determine the epitope or the set of epitopes that each of these antibodies binds to according to the above mapping method generally known in the art. One can then select those anti Notch-1 antibodies that bind to the specific epitope or the specific set of epitopes.

Conservative Substitution

As discussed previously, an antibody may also be modified recombinantly by conservative substitution of one or more of the amino acid residues of the antibody or by one or more deletions or additions of amino acids to that of the antibody.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the half-life of the antibody in the blood circulation.

Substitution variants have at least one amino acid residue in the antibody molecule removed and a different residue inserted in its place. The sites of greatest interest for substitutional mutagenesis include the hypervariable regions, but FR alterations are also contemplated. Conservative substitutions are shown in Table 2. If such substitutions result in a change in biological activity, then more substantial changes, denominated "exemplary substitutions" in Table 2, or as further described below in reference to amino acid classes, may be introduced and the products screened.

TABLE 2

Amino Acid Substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) Non-polar: Norleucine, Met, Ala, Val, Leu, Ile;

(2) Polar without charge: Cys, Ser, Thr, Asn, Gin;

(3) Acidic (negatively charged): Asp, Glu;

(4) Basic (positively charged): Lys, Arg;

(5) Residues that influence chain orientation: Gly, Pro; and (6) Aromatic: Trp, Tyr, Phe, His.

Non-conservative substitutions are made by exchanging a member of one of these classes for another class.

Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

Affinity Matured Anti Notch-1 Antibodies

The invention includes affinity matured embodiments. For example, affinity matured antibodies can be produced by procedures known in the art (Marks et al. (1992) Bio/Technology, 10:779-783; Barbas et al. (1994) Proc Nat. Acad. Sci, USA 91:3809-3813; Schier et al. (1995) Gene, 169:147-155; Yelton et al. (1995) J. Immunol., 155:1994-2004; Jackson et al. (1995) J. Immunol., 154(7):3310-9; Hawkins et al. (1992) J. Mol. Biol., 226:889-896; and PCT Publication No. WO2004/058184).

The following methods may be used for adjusting the affinity of an antibody and for characterizing a CDR. One way of characterizing a CDR of an antibody and/or altering (such as improving) the binding affinity of a polypeptide, such as an antibody, referred to "library scanning mutagenesis". Generally, library scanning mutagenesis works as follows. One or more amino acid positions in the CDR are replaced with two or more (such as 3, 4, 5, 6, 7, 8, 9, 10, 11, 12, 13, 14, 15, 16, 17, 18, 19, or 20) amino acids using art recognized methods.

This generates small libraries of clones (in some embodiments, one for every amino acid position that is analyzed), each with a complexity of two or more members (if two or more amino acids are substituted at every position). Generally, the library also includes a clone comprising the native (unsubstituted) amino acid. A small number of clones, e.g., about 20-80 clones (depending on the complexity of the library), from each library are screened for binding affinity to the target polypeptide (or other binding target), and candidates with increased, the same, decreased, or no binding are identified.

In some embodiments, every amino acid position in a CDR is replaced, in some embodiments, one at a time, with all 20 natural amino acids using art recognized mutagenesis methods. This generates small libraries of clones, in some embodiments, one for every amino acid position that is analyzed, each with a complexity of 20 members, if all 20 amino acids are substituted at every position.

In some embodiments, the library to be screened comprises substitutions in two or more positions, which may be in the same CDR or in two or more CDRs. Thus, the library may comprise substitutions in two or more positions in one CDR. The library may comprise substitution in two or more positions in two or more CDRs. The library may comprise substitution in 3, 4, 5, or more positions, said positions found in two, three, four, five or six CDRs. The substitution may be prepared using low redundancy codons. See, e.g., Table 2 of Balint et al., (1993) Gene 137(1):109-18). Each CDR may be a Kabat CDR, a Chothia CDR, or an extended CDR.

Candidates with improved binding may be sequenced, thereby identifying a CDR substitution mutant which results in improved affinity, which substitution is also referred to an "improved" substitution. Candidates that bind may also be sequenced, thereby identifying a CDR substitution which retains binding.

Multiple rounds of screening may be conducted. For example, candidates each comprising an amino acid substitution at one or more position of one or more CDR, with improved binding are also useful for the design of a second library containing at least the original and substituted amino acid at each improved CDR position (i.e., amino acid position in the CDR at which a substitution mutant showed improved binding). Preparation, and screening or selection of this library is discussed further below.

Library scanning mutagenesis also provides a means for characterizing a CDR, in so far as the frequency of clones with improved binding, the same binding, decreased binding or no binding also provide information relating to the importance of each amino acid position for the stability of the antibody-antigen complex. For example, if a position of the CDR retains binding when changed to all 20 amino acids, that position is identified as a position that is unlikely to be required for antigen binding. Conversely, if a position of CDR retains binding in only a small percentage of substitutions, that position is identified as a position that is important to CDR function. Thus, the library scanning mutagenesis methods generate information regarding positions in the CDRs that can be changed to many different amino acids (including all 20 amino acids), and positions in the CDRs which cannot be changed or which can only be changed to a few amino acids.

Candidates with improved affinity may be combined in a second library, which includes the improved amino acid, the original amino acid at that position, and may further include additional substitutions at that position, depending on the complexity of the library that is desired, or permitted using the desired screening or selection method. In addition, if desired, adjacent amino acid position can be randomized to at least two or more amino acids. Randomization of adjacent amino acids may permit additional conformational flexibility in the mutant CDR, which may in turn, permit or facilitate the introduction of a larger number of improving mutations. The library may also comprise substitution at positions that did not show improved affinity in the first round of screening.

The second library is screened or selected for library members with improved and/or altered binding affinity using any method known in the art, including screening using Biacore surface plasmon resonance analysis, and selection using any method known in the art for selection, including phage display, yeast display, and ribosome display.

Post Translational Modification of Anti Notch-1 Antibodies

Antibodies can also be modified by post translational modifications, including, but not limited to glycosylation with different sugars, acetylation, and phosphorylation. Antibodies are glycosylated at conserved positions in their constant regions. The oligosaccharide side chains of the immunoglobulins affect the protein's function (Boyd et al., 1996, Mol. Immunol. 32:1311-1318; Wittwe and Howard, 1990, Biochem. 29:4175-4180) and the intramolecular interaction between portions of the glycoprotein, which can affect the conformation and presented three-dimensional surface of the glycoprotein (Jefferis and Lund, supra; Wyss and Wagner, 1996, Current Opin. Biotech. 7:409-416). Oligosaccharides may also serve to target a given glycoprotein to certain molecules based upon specific recognition structures. Glycosylation of antibodies has also been reported to affect antibody-dependent cellular cytotoxicity (ADCC). In particular, CHO cells with tetracycline-regulated expression of $\beta(1,4)$—N-acetylglucosaminyltransferase III (GnTIII), a glycosyltransferase catalyzing formation of bisecting GlcNAc, was reported to have improved ADCC activity (Umana et al., 1999, Mature Biotech. 17:176-180).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, variations in the glycosylation pattern of the antibodies can be expected (see, e.g. Hse et al. (1997) J. Biol. Chem. 272:9062-9070).

In addition to the choice of host cells, factors that affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5.278, 299). Glycosylation, or certain types of glycosylation, can be enzymatically removed from the glycoprotein, for example, using endoglycosidase H (Endo H), N-glycosidase F, endoglycosidase F1, endoglycosidase F2, endoglycosidase F3. In addition, the recombinant host cell can be genetically engineered to be defective in processing certain types of polysaccharides. These and similar techniques are well known in the art.

Other methods of post translational modification include using coupling techniques known in the art, including, but not limited to, enzymatic means, oxidative substitution and chelation. Modifications can be used, for example, for attachment of labels for immunoassay.

Anti Notch-1 Antibodies with Modified Constant Region

In some embodiments of the invention, the antibody comprises a modified constant region, such as a constant region that is immunologically inert or partially inert, e.g., does not trigger complement mediated lysis, does not stimulate antibody-dependent cell mediated cytotoxicity (ADCC), or does not activate microglia; or have reduced activities (compared to the unmodified antibody) in any one or more of the following: triggering complement mediated lysis, stimulating antibody-dependent cell mediated cytotoxicity (ADCC), or activating microglia. Different modifications of the constant region may be used to achieve optimal level and/or combination of effector functions. See, for example, Morgan et al., Immunology 86:319-324 (1995); Lund et al., J. Immunology 157:4963-9 157:4963-4969 (1996); Idusogie et al., J. Immunology 164:4178-4184 (2000); Tao et al., J. Immunology 143: 2595-2601 (1989); and Jefferis et al., Immunological Reviews 163:59-76 (1998). In some embodiments, the constant region is modified as described in Eur. J. Immunol. (1999) 29:2613-2624; PCT Application No. PCT/GB99/01441; and/or UK Patent Application No. 9809951.8. In other embodiments, the antibody comprises a human heavy chain IgG2 constant region comprising the following mutations: A330P331 to S330S331 (amino acid numbering with reference to the wild type IgG2 sequence). Eur. J. Immunol. (1999) 29:2613-2624. In still other embodiments, the constant region is aglycosylated for N-linked glycosylation. In some embodiments, the constant region is aglycosylated for N-linked glycosylation by mutating the glycosylated amino acid residue or flanking residues that are part of the N-glycosylation recognition sequence in the constant region. For example, N-glycosylation site N297 may be mutated to A, Q, K, or H. See, Tao et al., J. Immunology 143: 2595-2601 (1989); and Jefferis et al., Immunological Reviews 163:59-76 (1998). In some embodiments, the constant region is aglycosylated for N-linked glycosylation. The constant region may be aglycosylated for N-linked glycosylation enzymatically (such as removing carbohydrate by enzyme PNGase), or by expression in a glycosylation deficient host cell.

Modifications within the Fc region can typically be used to alter one or more functional properties of the antibody, such as serum half-life, complement fixation, Fc receptor binding, and/or antigen-dependent cellular cytotoxicity. Furthermore, an antibody of the disclosure may be chemically modified (e.g., one or more chemical moieties can be attached to the antibody) or be modified to alter its glycosylation pattern, again to alter one or more functional properties of the antibody. Each of these aspects is described in further detail below. The numbering of residues in the Fc region is that of the EU index of Kabat.

In one case, the hinge region of CH1 is modified such that the number of cysteine residues in the hinge region is altered, e.g., increased or decreased. This approach is described further in U.S. Pat. No. 5,677,425. The number of cysteine residues in the hinge region of CH1 is altered to, for example, facilitate assembly of the light and heavy chains or to increase or decrease the stability of the antibody.

In another case, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745.

In another case, the antibody is modified to increase its biological half life. Various approaches are possible. For example, one or more of the following mutations can be introduced: T252L, T254S, T256F, as described in U.S. Pat. No. 6,277,375. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022.

In yet other cases, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the Cl component of complement. This approach is described in further detail in U.S. Pat. Nos. 5,624,821 and 5,648,260.

In another case, one or more amino acids selected from amino acid residues 329, 331 and 322 can be replaced with a different amino acid residue such that the antibody has altered Clq binding and/or reduced or abolished complement dependent cytotoxicity (CDC). This approach is described in further detail in U.S. Pat. No. 6,194,551.

In another example, one or more amino acid residues within amino acid positions 231 and 239 are altered to thereby alter the ability of the antibody to fix complement. This approach is described further in PCT Publication WO 94/29351.

In yet another example, the Fc region is modified to increase the ability of the antibody to mediate antibody dependent cellular cytotoxicity (ADCC) and/or to increase the affinity of the antibody for an Fcy receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072. Moreover, the binding sites on human IgG1 for FcγR1, FcγRII, FcγRIII and FcRn have been mapped and variants with improved binding have been described (see Shields et al., J. Biol. Chem. 276:6591-6604 (2001)). Specific mutations at positions 256, 290, 298, 333, 334 and 339 were shown to improve binding to FcγRIII.

Additionally, the following combination mutants were shown to improve FcγRIII binding: T256A/S298A, S298A/E333A, S298A/K$_{224}$A and S298A/E333A/K334A.

In still another example, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the disclosure to thereby produce an antibody with altered glycosylation. For example, the cell lines Ms704, Ms705, and Ms709 lack the fucosyltransferase gene, FUT8 (alpha (1,6) fucosyltransferase), such that antibodies expressed in the Ms704, Ms705, and Ms709 cell lines lack fucose on their carbohydrates. The Ms704, Ms705, and Ms709 FUT8$^{-/-}$ cell lines were created by the targeted disruption of the FUT8 gene in CHO/DG44 cells using two replacement vectors (see U.S. Patent Publication No. 2004-0110704, and Yamane-Ohnuki et al., *Biotechnol Bioeng* 87:614-22 (2004)). As another example, European Patent Publication No. EP1,176,195 describes a cell line with a functionally disrupted FUT8 gene, which encodes a fucosyl transferase, such that antibodies expressed in such a cell line exhibit hypofucosylation by reducing or eliminating the alpha 1,6 bond-related enzyme. EP1,176,195 also describe cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn(297)-linked carbohydrates, also resulting in hypofucosylation of antibodies expressed in that host cell (see also Shields et al., *J. Biol. Chem.* 277:26733-26740 (2002)). PCT Publication WO 99/54342 describes cell lines engineered to express glycoprotein-modifying glycosyl transferases (e.g., beta(1,4)—N-acetylglucosaminyltransferase III (GnTIII)) such that antibodies expressed in the engineered cell lines exhibit increased bisecting GlcNac structures which results in increased ADCC activity of the antibodies (see also Umana et al., *Nat. Biotech.* 17:176-180 (1999)). Alternatively, the fucose residues of the antibody may be cleaved off using a fucosidase enzyme. For example, the fucosidase alpha-L-fucosidase removes fucosyl residues from antibodies (Tarentino et al., (1975) *Biochem.* 14:5516-23 (1975)).

Another modification of the antibodies herein that is contemplated by the disclosure is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Typically, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$ to $C_{10}$) alkoxy- or aryloxy-polyethylene glycol or polyethylene glycol-maleimide. In certain cases, the antibody to be pegylated is an aglycosylated antibody. Methods for pegylating proteins are known in the art and can be applied to the antibodies of the present disclosure. See for example, European Patent Nos. EP 0154316B1 and EP 0401384B1.

Other antibody modifications include antibodies that have been modified as described in PCT Publication No. WO 99/58572. These antibodies comprise, in addition to a binding domain directed at the target molecule, an effector domain having an amino acid sequence substantially homologous to all or part of a constant domain of a human immunoglobulin heavy chain. These antibodies are capable of binding the target molecule without triggering significant complement dependent lysis, or cell-mediated destruction of the target. In some embodiments, the effector domain is capable of specifically binding FcRn and/or FcγRIIb. These are typically based on chimeric domains derived from two or more human immunoglobulin heavy chain $C_H2$ domains. Antibodies modified in this manner are particularly suitable for use in chronic antibody therapy, to avoid inflammatory and other adverse reactions to conventional antibody therapy.

Fusion Protein

The invention also encompasses fusion proteins comprising one or more fragments or regions from the antibodies or polypeptides of this invention. In one embodiment, a fusion polypeptide is provided that comprises at least 10 contiguous amino acids of the variable light chain region and/or at least 10 amino acids of the variable heavy chain region of the antibodies of the current invention. In other embodiments, a fusion polypeptide is provided that comprises at least about 10, at least about 15, at least about 20, at least about 25, or at least about 30 contiguous amino acids of the variable light chain region and/or at least about 10, at least about 15, at least about 20, at least about 25, or at least about 30 contiguous amino acids of the variable heavy chain region. In another embodiment, the fusion polypeptide comprises a light chain variable region and/or a heavy chain variable region, of the antibodies of the current invention. In another embodiment, the fusion polypeptide comprises one or more CDR(s) of the antibodies of the current invention. For purposes of this invention, a fusion protein contains one or more antibodies and another amino acid sequence to which it is not attached in the native molecule, for example, a heterologous sequence or a homologous sequence from another region. Exemplary heterologous sequences include, but are not limited to a "tag" such as a FLAG tag or a 6H is tag.

A fusion polypeptide can be created by methods known in the art, for example, synthetically or recombinantly.

Bispecific Molecules

An antibody of the disclosure, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody of the disclosure may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of the disclosure, an antibody of the disclosure can be functionally linked (e.g., by chemical coupling, genetic fusion, noncovalent association or otherwise) to one or more other binding molecules, such as another antibody, antibody fragment, peptide or binding mimetic, such that a bispecific molecule results.

Polynucleotides Encoding the Anti Notch-1 Antibodies

The invention also provides isolated polynucleotides encoding the antibodies and peptides of the invention, and vectors and host cells comprising the polynucleotide.

In one aspect, the invention provides compositions, such as a pharmaceutical composition, comprising any of the polynucleotides of the invention. In some embodiments, the composition comprises an expression vector comprising a polynucleotide encoding the antibody of the invention. In other embodiment, the composition comprises an expression vector comprising a polynucleotide encoding any of the antibodies or polypeptides of the invention.

In another aspect, the invention provides a method of making any of the polynucleotides described herein.

Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an antibody or a portion thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably, at least about 80% identity, yet more preferably, at least about 90% identity, and most preferably, at least about 95% identity to a polynucleotide sequence that encodes a native antibody or a portion thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this invention can be obtained using chemical synthesis, recombinant methods, or PCR.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al. (1989).

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston (1994).

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., (1989), supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The invention also provides host cells comprising any of the polynucleotides described herein. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as E. coli or B. subtillis) and yeast (such as S. cerevisae, S. pombe; or K. lactis). Preferably, the host cells express the cDNAs at a level of about 5 fold higher, more preferably, 10 fold higher, even more preferably, 20 fold higher than that of the corresponding endogenous antibody or protein of interest, if present, in the host cells. Screening the host cells for a specific binding to Notch-1 or a Notch-1 domain is effected by an immunoassay or FACS. A cell overexpressing the antibody or protein of interest can be identified.

Pharmaceutical Compositions

In another aspect, the present disclosure provides a composition, e.g., a pharmaceutical composition, containing one or a combination of monoclonal antibodies, or antigen-binding portion(s) thereof, of the present disclosure, formulated together with a pharmaceutically acceptable carrier. Such compositions may include one or a combination of (e.g., two or more different) antibodies, or immunoconjugates or bispecific molecules of the disclosure. For example, a pharmaceutical composition of the disclosure can comprise a combination of antibodies (or immunoconjugates or bispecifics) that bind to different epitopes on the target antigen or that have complementary activities.

Pharmaceutical compositions of the disclosure also can be administered in combination therapy, i.e., combined with other agents. For example, the combination therapy can include an anti-Notch1 antibody of the present disclosure combined with at least one other anti-inflammatory or immunosuppressant agent. Examples of therapeutic agents that can be used in combination therapy are described in greater detail below in the section on uses of the antibodies of the disclosure.

As used herein, "pharmaceutically acceptable carrier" includes any and all solvents, dispersion media, coatings, antibacterial and antifungal agents, isotonic and absorption delaying agents, and the like that are physiologically compatible. Typically, the carrier is suitable for intravenous, intramuscular, subcutaneous, parenteral, spinal or epidermal administration (e.g., by injection or infusion). Depending on the route of administration, the active compound, i.e., antibody, antigen-binding portion thereof, immunoconjuage, or bispecific molecule, may be coated in a material to protect the compound from the action of acids and other natural conditions that may inactivate the compound.

In certain embodiments, the antibodies of the present disclosure may be present in a neutral form (including zwitter ionic forms) or as a positively or negatively-charged species. In some cases, the antibodies may be complexed with a counterion to form a pharmaceutically acceptable salt. Thus, the pharmaceutical compounds of the disclosure may include one or more pharmaceutically acceptable salts.

A "pharmaceutically acceptable salt" refers to a salt that retains the desired biological activity of the parent compound (e.g. antibody) and does not impart undesired toxicological effects (see e.g., Berge, S. M., et al. (1977) J. Pharm. Sci. 66:1-19). For example, the term "pharmaceutically acceptable salt" includes a complex comprising one or more antibodies and one or more counterions, where the counterions are derived from pharmaceutically acceptable inorganic and organic acids and bases.

Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

Furthermore, pharmaceutically acceptable inorganic bases include metallic ions. Metallic ions include, but are not limited to, appropriate alkali metal salts, alkaline earth metal salts and other physiological acceptable metal ions. Salts derived from inorganic bases include aluminum, ammonium, calcium, cobalt, nickel, molybdenum, vanadium, manganese, chromium, selenium, tin, copper, ferric, ferrous, lithium, magnesium, manganic salts, manganous, potassium, rubidium, sodium, and zinc, and in their usual valences.

Pharmaceutically acceptable acid addition salts of the antibodies of the present disclosure can be prepared from the following acids, including, without limitation formic, acetic, acetamidobenzoic, adipic, ascorbic, boric, propionic, benzoic, camphoric, carbonic, cyclamic, dehydrocholic, malonic, edetic, ethylsulfuric, fendizoic, metaphosphoric, succinic, glycolic, gluconic, lactic, malic, tartaric, tannic, citric, nitric, ascorbic, glucuronic, maleic, folic, fumaric, propionic, pyruvic, aspartic, glutamic, benzoic, hydrochloric, hydrobromic, hydroiodic, lysine, isocitric, trifluoroacetic, pamoic, propionic, anthranilic, mesylic, orotic, oxalic, oxalacetic, oleic, stearic, salicylic, aminosalicylic, silicate, p-hydroxybenzoic, nicotinic, phenylacetic, mandelic, embonic, sulfonic, methanesulfonic, phosphoric, phosphonic, ethanesulfonic, ethanedisulfonic, ammonium, benzenesulfonic, pantothenic, naphthalenesulfonic, toluenesulfonic, 2-hydroxyethanesulfonic, sulfanilic, sulfuric, nitric, nitrous, sulfuric acid monomethyl ester, cyclohexylaminosulfonic, β-hydroxybutyric, glycine, glycylglycine, glutamic, cacodylate, diaminohexanoic, camphorsulfonic, gluconic, thiocyanic, oxoglutaric, pyridoxal 5-phosphate, chlorophenoxyacetic, undecanoic, N-acetyl-L-aspartic, galactaric and galacturonic acids.

Pharmaceutically acceptable organic bases include trimethylamine, diethylamine, N,N'-dibenzylethylenediamine, chloroprocaine, choline, dibenzylamine, diethanolamine, ethylenediamine, meglumine (N-methylglucamine), procaine, cyclic amines, quaternary ammonium cations, arginine, betaine, caffeine, clemizole, 2-ethylaminoethanol, 2-diethylaminoethanol, 2-dimethylaminoethanol, ethanediamine, butylamine, ethanolamine, ethylenediamine, N-ethylmorpholine, N-ethylpiperidine, ethylglucamine, glucamine, glucosamine, histidine, hydrabamine, imidazole, isopropylamine, methylglucamine, morpholine, piperazine, pyridine, pyridoxine, neodymium, piperidine, polyamine resins, procaine, purines, theobromine, triethylamine, tripropylamine, triethanolamine, tromethamine, methylamine, taurine, cholate, 6-amino-2-methyl-2-heptanol, 2-amino-2-methyl-1,3-propanediol, 2-amino-2-methyl-1-propanol, aliphatic mono- and dicarboxylic acids, phenyl-substituted alkanoic acids, hydroxy alkanoic acids, aromatic acids, aliphatic and aromatic sulfonic acids, strontium, tricine, hydrazine, phenylcyclohexylamine, 2-(N-morpholino)ethanesulfonic acid, bis(2-hydroxyethyl)amino-tris(hydroxymethyl)methane, N-(2-acetamido)-2-aminoethanesulfonic acid, 1,4-piperazinediethanesulfonic acid, 3-morpholino-2-hydroxypropanesulfonic acid, 1,3-bis[tris(hydroxymethyl)methylamino]propane, 4-morpholinepropanesulfonic acid, 4-(2-hydroxyethyl)piperazine-1-ethanesulfonic acid, 2-[(2-hydroxy-1,1-bis(hydroxymethyl)ethyl)amino]ethanesulfonic acid, N,N-bis(2-hydroxyethyl)-2-aminoethanesulfonic acid, 4-(N-morpholino)butanesulfonic acid, 3-(N,N-bis[2-hydroxyethyl]amino)-2-hydroxypropanesulfonic acid, 2-hydroxy-3-[tris(hydroxymethyl)methylamino]-1-propanesulfonic acid, 4-(2-hydroxyethyl)piperazine-1-(2-hydroxypropanesulfonic acid), piperazine-1,4-bis(2-hydroxypropanesulfonic acid) dihydrate, 4-(2-hydroxyethyl)-1-piperazinepropanesulfonic acid, N,N-bis(2-hydroxyethyl)glycine, N-(2-hydroxyethyl)piperazine-N'-(4-butanesulfonic acid), N-[tris(hydroxymethyl)methyl]-3-aminopropanesulfonic acid, N-tris(Hydroxymethyl)methyl-4-aminobutanesulfonic acid, N-(1,1-dimethyl-2-hydroxyethyl)-3-amino-2-hydroxypropanesulfonic acid, 2-(cyclohexylamino)ethanesulfonic acid, 3-(cyclohexylamino)-2-hydroxy-1-propanesulfonic acid, 3-(cyclohexylamino)-1-propanesulfonic acid, N-(2-acetamido)iminodiacetic acid, 4-(cyclohexylamino)-1-butanesulfonic acid, N-[tris(hydroxymethyl)methyl]glycine, 2-amino-2-(hydroxymethyl)-1,3-propanediol, and trometamol.

A pharmaceutical composition of the disclosure also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the disclosure is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation include, but are not limited to, vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the disclosure are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1 to 10 mg/kg. An exemplary treatment regime entails administration once per week, once every two weeks, once every three weeks, once every four weeks, once per month, once every 3 months or once every three to 6 months. Dosage regimens for an anti-Notch-1 antibody or antigen binding portion thereof of the disclosure include, for example, 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1 to 1000 µg/ml and in some methods about 25 to 300 µg/ml.

Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-Notch antibody of the disclosure preferably results in a decrease in severity of disease symptoms, an increase in frequency and duration of disease symptom-free periods, or a prevention of impairment or disability due to the disease affliction. For example, for the treatment of Notch-1-positive tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject.

One of ordinary skill in the art would be able to determine such amounts based on such factors as the subject's size, the severity of the subject's symptoms, and the particular composition or route of administration selected.

A composition of the present disclosure can be administered via one or more routes of administration using one or more of a variety of methods known in the art. As will be appreciated by the skilled artisan, the route and/or mode of administration will vary depending upon the desired results. Routes of administration for antibodies or antigen binding portions thereof of the disclosure include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody or antigen biding portion thereof of the disclosure can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Uses and Methods of the Disclosure

The antibodies, particularly the human antibodies, antibody compositions and methods of the present disclosure have numerous in vitro and in vivo diagnostic and therapeutic utilities involving the diagnosis and treatment of Notch-1 mediated disorders. For example, these molecules can be administered to cells in culture, in vitro or ex vivo, or to human subjects, e.g., in vivo, to treat, prevent and to diagnose a variety of disorders. As used herein, the term "subject" is intended to include human and non-human animals. Non-human animals include all vertebrates, e.g., mammals and non-mammals, such as non-human primates, sheep, dogs, cats, cows, horses, chickens, amphibians, and reptiles. Preferred subjects include human patients having disorders mediated by Notch-1 activity. The methods are particularly suitable for treating human patients having a disorder associated with aberrant Notch-1 expression or activation. When antibodies to Notch-1 are administered together with another agent, the two can be administered in either order or simultaneously.

Given the specific binding of the antibodies of the disclosure for Notch-1, the antibodies of the disclosure can be used to specifically detect Notch-1 expression on the surface of cells and, moreover, can be used to purify Notch-1 via immunoaffinity purification.

Furthermore, the antibodies, antibody compositions and methods of the present disclosure can be used to treat a subject with abnormal cell growth, e.g., a cancer. In one particular embodiment, the cancer is T-ALL. In another particular embodiment, the cancer is breast cancer.

Other type of abnormal cell growth that may be treated by the antibodies of the invention include, for example, mesothelioma, hepatobilliary (hepatic and billiary duct), a primary or secondary CNS tumor, a primary or secondary brain tumor, lung cancer (NSCLC and SCLC), bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, non hodgkins's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

Suitable routes of administering the antibody compositions (e.g., human monoclonal antibodies, multispecific and bispecific molecules and immunoconjugates) or antigen binding portions thereof of the disclosure in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

As previously described, human anti-Notch-1 antibodies or antigen binding portions thereof of the disclosure can be co-administered with one or other more therapeutic agents, e.g., a cytotoxic agent, a radiotoxic agent or an immunosuppressive agent. The antibody can be linked to the agent (as an immunocomplex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, and cyclophosphamide hydroxyurea which, by themselves, are only effective at levels which are toxic or subtoxic to a patient. Cisplatin can be intravenously administered as a 100 mg/dose once every four weeks and adriamycin is intravenously administered as a 60 to 75 mg/ml dose once every 21 days. Co-administration of the human anti-Notch-1 antibodies, or antigen binding fragments thereof, of the present disclosure with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Kits

Also within the scope of the present disclosure are kits comprising the antibody compositions of the disclosure (e.g., human antibodies, bispecific or multispecific molecules, or immunoconjugates) and instructions for use. The kit can further contain one or more additional reagents, such as an immunosuppressive reagent, a cytotoxic agent or a radiotoxic agent, or one or more additional antibodies or antigen binding portions thereof of the disclosure (e.g., a human antibody having a complementary activity which binds to an epitope in the Notch-1 antigen distinct from the first human antibody).

Accordingly, patients treated with antibody compositions of the disclosure can be additionally administered (prior to, simultaneously with, or following administration of a human antibody of the disclosure) another therapeutic agent, such as a cytotoxic or radiotoxic agent, which enhances or augments the therapeutic effect of the human antibodies.

The present disclosure is further illustrated by the following examples which should not be construed as further limiting. The contents of all figures and all references, patents and published patent applications cited throughout this application are expressly incorporated herein by reference.

EXAMPLES

Example 1

Generation and Expression of Notch1 Immunogen

Generation of Notch1 immunogen expression constructs

Figure 1:
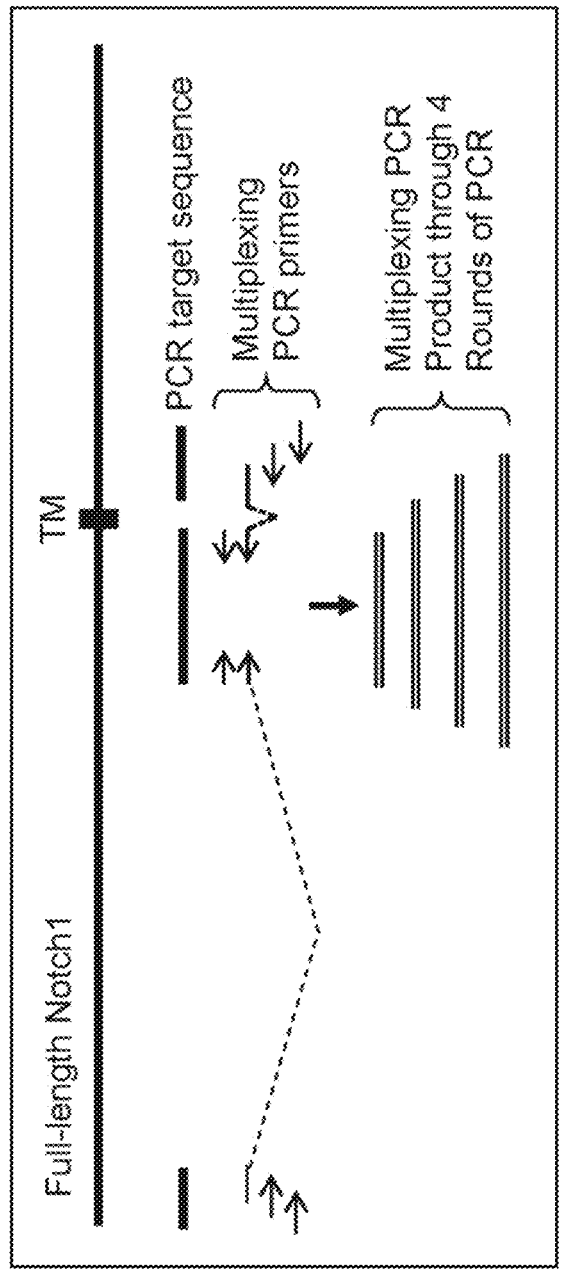
FIG. 1 illustrates the PCR synthesis of the cDNA of a human Notch1 immunogen plasmid N1-NRR-TM(-), as described in Example 1.

The immunogen constructs were generated by multiplexing PCR (FIG. 1) for monoclonal antibody (mAb) generation. As illustrated in FIG. 1, the Notch1 immunogen cDNA was synthesized by multiple overlapping PCR using the Notch1 full-length cDNA clone as template (OriGene, Cat. No. TC308883, Rockville, Md.) and High Fidelity PCR reagent system following the manufacturer's protocol (Roche, Indianapolis, Ind.). The recombinant Notch1 immunogen cDNA, containing N-terminal leader peptide, EGF-like repeats 35-36, NRR, (including Lin A, B and C domains and the HD domain) and a small portion of intracellular sequence, was cloned in a Fc-fusion protein vector with Notch1 immunogen fused to the N-terminus of Fc sequence. The Notch1 immunogen plasmid, referred to as N1-NRR-TM(−), contains the cDNA insert shown in sequence 1, (SEQ ID NO:1), which encodes the immunogen protein shown in sequence 2 (SEQ ID NO:2).

Figure 2:
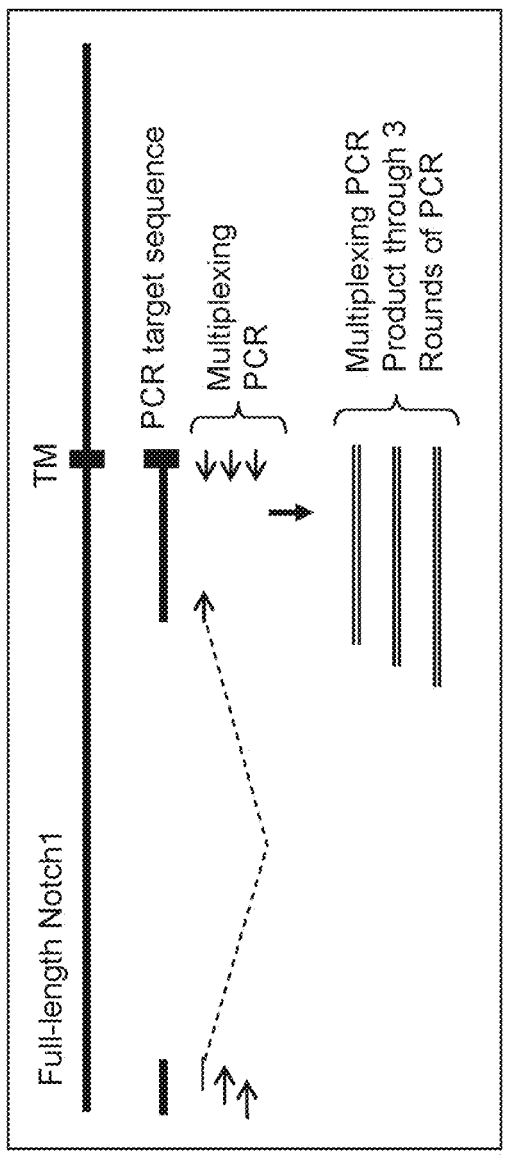
FIG. 2 illustrates the PCR synthesis of the cDNA of another human Notch1 immunogen plasmid N1-NRR-TM(+), also described in Example 1.

A similar plasmid was constructed in parallel as shown in FIG. 2, which contains the same sequence as N1-NRR-TM (−) except that the transmembrane (TM) sequence (the last 24 amino acid residues in Sequence 4) was used to replace the intracellular sequence (the last 44 amino acid residues in Sequence 2) of N1-NRR-TM(−). This PCR-amplified Notch1 immunogen cDNA was cloned in pcDNA3.1D/V5-His (Invitrogen). The plasmid was referred to as N1-NRR-TM(+). The nucleic acid sequence and amino acid sequence of N1-NRR-TM(+) is shown as Sequence 3 (SEQ ID NO:3) and 4 (SEQ ID NO:4).

Expression and Purification of Notch1 Immunogen Protein

N1-NRR-TM(−) was expressed in Freestyle™ 293-F cells (Invitrogen, Inc., Calsbad, Calif.) by transient transfection using Freestyle™ Max Reagent (Invitrogen) and the manufacturer's protocol, verified by Western blot analysis. Briefly, $1 \times 10^7$ cells were seeded in a tissue culture shaker flask containing 30 milliliters (ml) of 293-F cell growth medium (Invitrogen). The secreted protein was analyzed by taking an aliquot of 0.5 ml conditioned medium every 24 hours from day 2 to day 7 after transfection. Twenty microliters (ul) of conditioned medium and 2× protein sample loading buffer (Bio-Rad, Hercules, Calif.) were combined, heated at 100° C. for 5 minutes. The samples were separated through electrophoresis in a 4-12% gradient SDS-PAGE (Invitrogen). The proteins were transferred from gel to blotting membrane using a dry blotting device (Invitrogen), then the membrane was blocked in 5% non-fat dry milk in PBST (PBS with 0.05% tween-20) for one hour. Detection of N1-MRRHD-TM(−)/Fc fusion proteins was performed by incubation with human γFc-specific, HRP-conjugated antibody (Bethyl Lab. Inc. Montgomery, Tex.). The membrane was washed three times in PBST before developing with Supersignal Chemiluminescent Substrate (Pierce, Rockford, Ill.). The protein expression time course study showed that the conditioned medium of 5-6 day culture contains most secreted N1-NRR-TM(−)/Fc fusion protein. Therefore, N1-NRR-TM(−)/Fc protein expression was scaled up in 10 liters of culture volume, and the protein was purified through protein G affinity column (Invitrogen).

Establishing Cell Lines Expressing Notch1 Immunogen

N1-NRR-TM(+) was stably transfected in a mouse cell line, L-929 (ATCC, CCL-1, Manassas, Va.), expressed as cell surface membrane-anchored protein. The stable cell line was established by transfection using LipoFectamine™ 2000 (Invitrogen), and the cells were selected against 1 mg/ml of neomycin (G418) for about 9-15 days until individual colonies were visible by eye and picked up for clonal growth. The expression level of N1-NRR-TM(+)/V5 protein was assessed by Western blot using protein extract made from each stable transfection clone. More specifically, cells of each clone were removed from culture vessels, rinsed with phosphate buffered saline (PBS) and subjected to Western blot analysis described as above. The protein was detected by HRP-conjugated anti-V5 antibody (Invitrogen). The cell clones expressing highest level of N1-NRR-TM(+) protein was selected for the use of immunization and cell-based antibody binding assay.

Example 2

Generation of Notch1 mAb

Immunization and Hybridoma Cloning

Balb/c mice were immunized using human Notch1 immunogen, N1-NRR-TM(−), and a long immunization protocol. The first immunization was given via subcutaneous (sc) injection with twenty micrograms (μg) of the antigen mixed in Complete Freunds Adjuvant (CFA) emulsion, followed by three biweekly sc injections with each delivering 20 μg of antigen mixed in Incomplete Freunds Adjuvant (IFA) emulsion. The serum was taken a week after fourth antigen injection to check the titer of antibodies by ELISA. The mouse with high response titer was euthanized, and the spleen was surgically removed for hybridoma cloning.

A single cell suspension of spleenocytes were prepared by forcing the spleen through a 100-micron stainless steel screen, then through a cell strainer, and wash twice in 30 ml RPMI. The spleenocytes were mixed with Sp2/0-Ag14 cells (Sigma, St. Louis, Mo.) in three to one ratio, and cell fusion was facilitated by adding 50% PEG-1500 and gentle stirring. The mixture of cells were precipitated by centrifugation, and gently washed with RPMI, followed by incubation in RPMI-1640 medium with 20% fetal calf serum (FCS) at 37° C. for 30 minutes. The cells were suspended in RPMI-1640 containing 20% FCS, standard HAT (hypoxanthine, aminopterin and thymidine), 25% spleen-conditioned medium, 2 mM glutamate and 100 ug/ml Pen-Strip, (Invitrogen; Calsbad, Calif.), dispensed in 96-well plates and cultured in 37° C./5% $CO_2$ incubator for 8 to 20 days to allow HAT-resistant hybridoma clones established. The conditioned media from each hybridoma clone were subjected to ELISA screening.

ELISA Screening of Monoclonal Antibodies (mAb)

Enzyme-linked immunoabsorbent assay (ELISA) were performed using Nunc™ MaxiSorp 96-well plates (ThermoFisher Scientific, Rochester, N.Y.), which were prepared in two sets: the positive test plates coated overnight with 100 ng of N1-NRR-TM(−)/Fc protein in each well and the negative control plates coated with 100 ng of human Fc protein. Conditioned media from hybridoma clones were screened for their ability to bind N1-NRR-TM(−)/Fc protein. One hundred microliters of each hybridoma supernatant were added to the coated plates, and incubated at room temperature for one hour. The wells were washed three times with PBST (1×PBS with containing 0.05% Tween-20). Horse radish peroxidase (HRP) conjugated goat-anti-mouse Fc antibody was added to detect the mAbs bound to the antigen. Excessive HRP was washed off by three times of washes with PBST, 200 µl per well for each wash. ABTS (2,2′-azino-bis-[3-ethylbenzthiazoline-6-sulfonic acid]) solution was then added as substrate for HRP color development. The reaction was stopped and plates were scanned by a plate reader at 405 nm. Positive wells were re-screened with N1-NRR-TM(−)/Fc protein-coated plates and counter-screened with human Fc-coated plates in the same manner as described above. The hybridoma mAbs only binding to N1-NRR-TM(−)/Fc protein but not to human Fc were true Notch1-binding antibodies, which were selected to proceed for functional screening.

Example 3

Identification and Characterization of Notch1-Antagonist mAb

Establishing Luciferase Reporter Assay Cell Lines

Luciferase reporter assay was commonly used to assess Notch1 receptor-mediated signaling and transcriptional activity in a variety of settings (Weng, A. P., et. al, Science, 2004, 9265-9273; Osipo et al., Oncogene, 2008, 27(37): 5019-5032). For assaying ligand-induced Notch1 activation and mAb inhibition, the tool cell lines were developed to enhance Notch signaling. It was well established that the active form of Notch receptor consisting of intracellular domain translocates to the nucleus, and forms complex with CSL [named after CBF1, Su(H) and LAG-1] binding factor 1, which binds to the core sequence called CSL-binding motif in a gene promoter region, activating the downstream gene transcription (Bray, 2006). Based on those discoveries, the Notch1-mediated luciferase reporter plasmid was generated. Briefly, a concatamers of eight CSL binding motifs as described by Tun et al. (Tun et al., Nucleic Acids Res. 1994m 22(6):965-971) were inserted in the multiple cloning site of pTA-Luc (BD Biosiences, Palo Alto, Calif.). A hygromycin selection marker (see next paragraph) was added to the down stream of luciferase gene. This yielded the luciferase reporter plasmid, CSLuc.

The full length Notch1 expression construct was obtained from OriGene (Rockville, Md.) and verified by sequencing as identical to NM_017617.2 (NCBI/GenBank accession number). A hygromycin selection marker with SV40 promoter was PCR-synthesized from pcDNA3.1/Hygromycin (Invitrogen), and connected to a growth hormone 3′ poly-A signaling sequence from pcDNA5/RFT/V5-His (Invitrogen) by standard PCR joining method. The completed hygromycin marker was inserted in the Cla I site of the Notch1 expression plasmids. This plasmid is renamed as Notch1/Hyg. To enhance Notch1 activity, PEDT domain (Weng, A. P., et. al, Science, 2004, 9265-9273 et. al.) was deleted from Notch1/Hyg by site-directed mutagenesis (Genewiz, South Plainfield, N.J.). The resulting plasmid was named as Notch1-dPEST. Human Jagged1 cDNA plasmid was obtained from Open Biosystems (Huntsville, Ala.). Jagged1 coding region was PCR-synthesized, and inserted into pcDNA3.3-TOPO expression vector (Invitrogen).

Notch1-dependent assay cell lines were generated by cotransfecting Notch1/hyg and CSLuc plasmids into U2-OS (ATCC Number HTB-96, Manassas, Va.) cells, or by cotransfecting Notch1-dPEST and CSLuc into 293T (ATCC Number CRL-11268, Manassas, Va.) cells using LipoFectamine 2000 according to the manufacturer's protocol (Invitrogen). Stably-transfected cells were clonally selected against 200-800 µg/ml hygromycin in DMEM growth medium (Invitrogen), the cell clones were screened by Western blot analysis as described in Example 1 and by luciferase reporter assay described in following sections. A cell line with relatively high level of Notch1 expression (based on Western blot) and Delta like-4 (Dll4)-induced luciferase activity was selected for use in functional assay. Two such example cell lines are U2-OS/Notch1-CSLuc (nick name: N1CU3) and 293/Notch1-dPEST-CSLuc (nick name: N1dP-c16). Through similar procedure, a cell line stably-expressing human Jagged1 was generated from a parental cell line, Hela (ATCC number CCL-2). The cell line was named as Hela/JAG1.

Luciferase Reporter Assay and Identification of Notch1-Antogonist Hybridoma Clones For identifying Notch1-inhibitory hybridoma clones, luciferase reporter assay was performed to assess Dll4-induced Notch1 activity in N1CU3 cells. The 96-well tissue culture plates (BD Bioscience) were coated with 50 to 100 nanograms (ng) of recombinant Dll4 (R&D Systems, Minneapolis, Minn.) per well. N1CU3 cells were seeded at 50,000 cells per well in the Dll4- or BSA-coated plates, 30 to 50 ul of conditioned media from hybridoma clones were added at same time, and cultured for 24 to 40 hours. At the end of the culture, cells were directly lysed in 1× Passive Lysis Buffer (Promega, Madison, Wis.) after removing all medium, and luciferase reporter activities were assayed using Bright-Glo™ Luciferase Assay System following manufacturer's protocol (Promega, Madison, Wis.) and MicroLumat Plus LB 96V luminometer (Berthhold Technologies, Bad Wildbad, Germany). Hybridoma supernatants with statistically significant inhibition to Dll4-induced Notch reporter activity were subjected to affinity purification through Protein-G column (Pierce, Rockford, Ill.) following manufacturer's protocol. The purified mAb were further analyzed by luciferase reporter assays again to confirm the inhibitory function to Notch1-dependent signaling.

Characterization of the Anti-Notch1 mAb by Luciferase Reporter Assays

Figure 3:
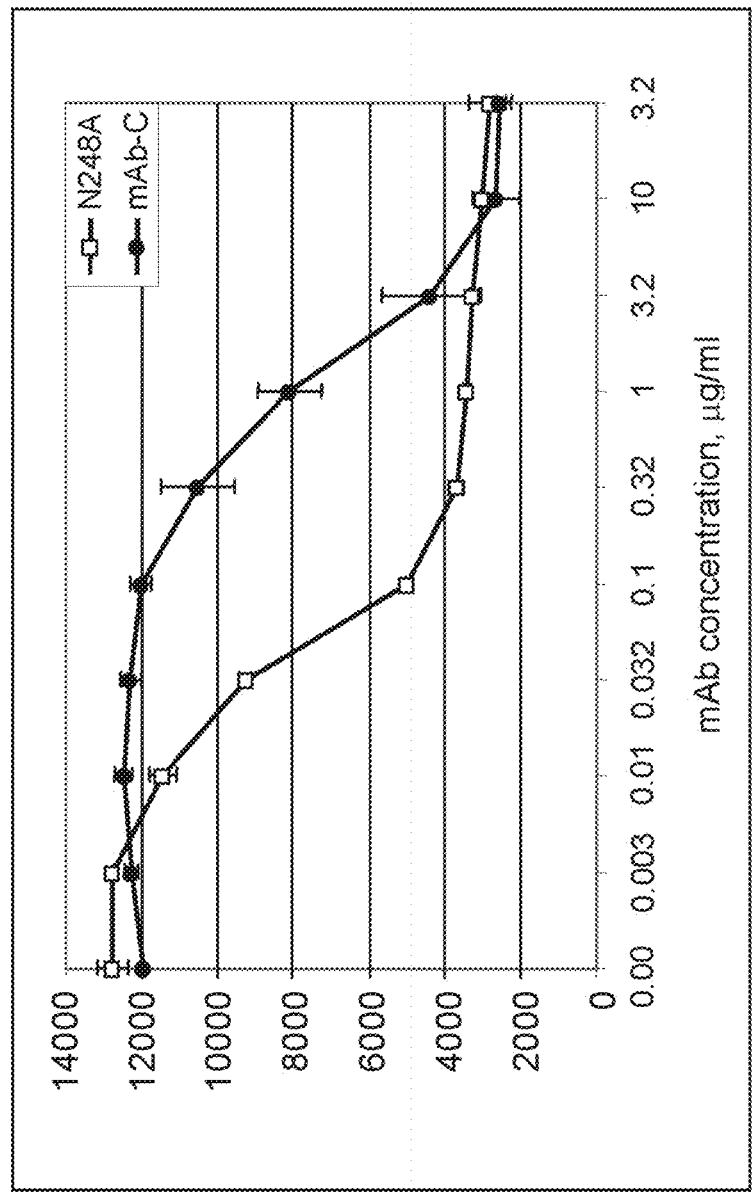
FIG. 3 illustrates the Notch-1 dependent luciferase reporter assay results of two monoclonal antibodies: mAb N248A and mAb-C, as shown in Example 3.

Among the mAbs inhibiting Notch1-mediated signaling, one mAb (N248A) showed the most potent inhibitory activity, which was characterized in detail through several different luciferase reporter assays. FIG. 3 shows that mAb N248A had much higher potency inhibiting Dll4 ligand-induced Notch1 signaling than that of companion mAb, mAb-C when Dll4 was coated on the surface of culture plate to induce Notch signaling. The 293/Notch1-dPEST-CSLuc cells were used in the assay. The y-axis numbers are luciferase reporter activity readings.

To assess whether mAb N248A can inhibit other Notch ligand-induced signaling, Hela/Jagged1 cells and N1dP-c16 cells were co-cultured and luciferase reporter assay as described above was performed. mAb N248A indeed completely inhibited Jagged1-induced Notch1 signaling (FIG. 4).

Example 4

Determining Antibody Binding Affinity

The physical binding affinity of anti-Notch1 mAb N248A, to Notch1 antigen was measured on a surface plasmon resonance Biacore 3000 instrument equipped with a research-grade sensor chip (Chip type: CM5) using HBSP running buffer (Biacore AB, Uppsala, Sweden—now GE Healthcare) plus 1 mM $CaCl_2$. Protein A was amine-coupled at saturating levels onto the chip using a standard N-hydroxysuccinimide/ethyldimethylaminopropyl carbodiimide (NHS/EDC) chemistry. N1-NRR-TM(-)Fc protein (described in Example 1) was captured to the chip surface by Protein A in all three flow cells at 40, 13, 4 ug/ml. Anti-Notch1 mAb N248A was diluted in a 3-fold series, injected for 1 min at 100 μl/min. Dissociation was monitored for 20 minutes. The chip was regenerated after the last injection of each titration with two 30 second pulses of 100 mM phosphoric acid. Buffer cycles provided blanks for double-referencing the data, which were then fit globally to a simple binding model using Biaevaluation software v.4.1. Affinities were deduced from the quotient of the kinetic rate constants ($K_D=k_{off}/k_{on}$). The data show that mAb N248A has $K_{on}$=5.19e-5 (Ms), $K_{off}$<1.7e-4 (1/s) and $K_D$<0.33 nM. The tight $K_D$ is contributed both by fast $K_{on}$ and very slow $K_{off}$, which is slower than that resolvable by our assay (Refer to 5% rule, Biacore 3000 manual).

Example 5

Analysis of Notch1-Antagonist mAb Binding Epitopes

Mapping mAb Binding Epitopes by Domain Swap with Human Notch2

For understanding the mechanism of action by Notch1-antagonist mAb, binding epitopes of Notch1-antagonist mAbs were analyzed by domain swap and ELISA binding assay. The Notch1-NRR-TM(-)/Fc protein was divided into six domains: EGF (including EGF35-36), Lin12-A (or Lin-A), Lin-B, Lin-C, heterodimerization domain-N (or HD-N) and HD-C (FIG. 5). Each of the domains were swapped for that corresponding to human Notch2 by PCR synthesis in a series of chimeric Notch1-NRR-TM(-)/Fc expression constructs. The domain-swap plasmids were transfected in Freestyle™ 293-F cells (Invitrogen, Inc., Calsbad, Calif.) using Freestyle™ Max Reagent (Invitrogen) as described above in Example 1. After being cultured for three days, the conditioned media was subjected to Western blot analysis and an ELISA binding assay by Notch1 mAbs. Western blot (method as in Example 1) showed that five of the six domain-swap constructs expressed well except that Lin-B/Notch2 swap was poorly expressed.

In ELISA assay, the 100 microliters of the conditioned medium from the above antigen plasmids-transfected cell culture were loaded in each well of the 96-well plate, and plates were incubated at room temperature for 4 hours or 4° C. for overnight. The condition medium was then removed from the coated plates. For primary antibody binding, 300 ng of each mAb (Table 3) in 100 microliters of PBS was added to the coated well. The rest of the ELISA procedure is the same as described in Example 2. The mAb N99a, N326A and N440A were monoclonal antibodies that bind to Notch-1, generated and isolated by the same procedures that of mAb N248A. As shown in Table 3, binding of mAb N248A to the chimeric antigens was completely abolished when Lin-A or HD-C domain was swapped to corresponding Notch2 domain. On the other hand, swapping of EGF, Lin-C or HD-C domain did not affect its binding. The mAbs N326A and N440A were distinctly different from mAb N248A. These two mAbs require HD-N and HD-C domains for their binding activity. N99A is somewhat similar to mAb N248A in that its binding requires Lin-A and HD-C domains. However, swap of the HD-N domain also reduced N99A binding activity. These data supported the conclusion that mAb N248A has at least two distinguishable sets of binding epitopes, one in Lin-A domain and the other in HD-C domain. Whether there is another epitope in Lin-B domain was resolved in a separate experiment. Similarly, all the other three Notch1-antagonist mAbs have two identifiable sets of binding epitopes, one in the HD-C domain and the other in the domains of Notch1 N-terminal subunit. Based on the recently published crystal structures of Notch1 (Gordon, W R et al., Blood, 2009, Volume 113, 4381-4390) and Notch2 (Gordon et al., Nature Structure Molecular Biology, 2007, Volume 14, 295-300) NRR regions, the three Lin12 domains are wrapped around the HD domains, blocking random cleavage and activation by ADAM protease, and therefore maintaining the receptor in non-active or silent status. The mAb N248A binds to Notch1 at two distinct sets of epitopes, causing the Notch1 to be locked down in the silent conformation, and thus preventing the receptor from being activated by its ligands.

Notch1 gene mutations, mostly point mutations and some small deletions and insertions, have been reported in more than 50% of T-ALL (Weng, A. P., et. al, Science, 2004, 9265-9273; Malecki et al., Molecular Cell Biology, 2006, 26(12): 4642-4651). The mutations are clustered in two regions: one in the C-terminus of the intracellular moiety and the other in the HD-N domain. These findings support the notion that mAb N248A would have better therapeutic utility in T-ALL than the other three mAbs listed in Table 3 because the HD-N domain swap did not affect the binding of mAb N248A to Notch1 while the binding of the other three was affected (see Table 3).

TABLE 3

ELISA reading of Notch1 mAb binding to chimeric antigens

| mAbs | | N248A | N99A | N326A | N440A |
|---|---|---|---|---|---|
| Notch1 chimeric antigen swapped with corresponding Notch2 domain | EGF | 3.51 | 3.20 | 3.48 | 2.85 |
| | Lin-A | 0.05 | 0.04 | 3.47 | 3.28 |
| | Lin-B | n/a | n/a | n/a | n/a |
| | Lin-C | 3.48 | 3.17 | 3.50 | 2.83 |
| | HD-N | 3.52 | 1.25 | 0.10 | 0.12 |
| | HD-C | 0.04 | 0.04 | 0.05 | 0.07 |

N248A binds to human Notch1, but not mouse Notch1

To locate the binding epitopes of N248A1, we generated murine Notch1-NRRHD expression plasmids containing mouse Notch1 cDNA coding region from nucleotide 1-99 and nucleotide 4327 to 5169 (NCBI Accession #, NM_008714), and performed transient transfection and ELISA binding assay (methods described in previous sections, Example 1 and 5). The results showed that N248A1 does not bind to mouse Notch1, and only binds to human Notch1 (Table 4). We further made domain-swap chimeric Notch1-NRRHD expression constructs using the human Notch1-NRRHD sequence (Nucleotide 1-129 and 4338-5202, NCBI Accession # NM_017617) as frame work, systematically exchanged the human Lin-A, Lin-B or HD-C domains with the corresponding mouse domains. An ELISA binding assay using this human/mouse domain swap protein as bait demonstrated that the binding of N248A1 to human Notch1 antigen is abolished when the Lin-A domain is exchanged to mouse sequence while the Lin-B or HD-C domain exchange did not affect the binding. In contrast, the other control mAb, 22F7, loses binding only when Lin-B is exchanged to the mouse sequence. Therefore, the binding epitope that determines whether N248A1 only binds to human Notch1, not to mouse, is located in the Lin-A domain.

TABLE 4

ELISA readings of Notch1 mAb binding to human, mouse and chimeric antigens

| Antigens | | N248A | 22F7 |
|---|---|---|---|
| huN1-NRRHD | | 3.13 | 3.19 |
| MuN1-NRRHD | | 0.17 | 0.09 |
| Notch1 chimeric antigen indicated | Mu/Lin-A | 0.33 | 3.27 |
| | Mu/Lin-B | 3.37 | 0.38 |

TABLE 4-continued

ELISA readings of Notch1 mAb binding to human, mouse and chimeric antigens

| Antigens | | N248A | 22F7 |
|---|---|---|---|
| domain swapped with murine sequence | Mu/HD-C | 3.17 | 3.19 |

Identify Binding Epitope of N248A1 in Lin-A Domain

To identify binding epitope of N248A1 in the Lin-A domain, we mutated the two amino acids which are different between the human and mouse Lin-A domains, i.e. 1457E/A and 1465S/N, (Table 5). ELISA results showed that mutation 1457E/A did not affect the binding, but mutation 1465S/N abolished the binding, indicating that amino acid Asn (N) in mouse Lin-A is the sole amino acid residue responsible for blocking N248A1 binding to mouse Notch1. Several amino acids surrounding 1465S were mutated to alanine sequentially (Table 5). Mutation of 1463V/A, 1466L/A or 1467Q/A also abolished the N248A1 binding. However, the control mAb A2 was not affected by the mutations 1463V/A or 1465S/N (Table 5). These experiments demonstrated that the binding epitope of N248A1 in Lin-A involves 1463V, 1465S, 1466L and 1467Q.

TABLE 5

Analysis of N248A1 point mutation and ELISA binding activity

| | | Binding activity | |
|---|---|---|---|
| Antigens | Sequence of Lin-A | N248A1 | A2 |
| huN1-NRRHD SEQ ID NO: 23 | ACELPECQEDAGNKVCSLQCNNHACGWDGGDCSLNFNDPWKN | 100% | 100% |
| mu/Lin-A SEQ ID NO: 24 | ACELPECQVDAGNKVCNLQCNNHACGWDGGDCSLNFNDPWKN | 11% | 151% |
| Mutant 1457E/A SEQ ID NO: 25 | ACELPECQADAGNKVCSLQCNNHACGWDGGDCSLNFNDPWKN | 112% | 110% |
| Mutant 1462K/A SEQ ID NO: 26 | ACELPECQEDAGNAVCSLQCNNHACGWDGGDCSLNFNDPWKN | 85% | 88% |
| Mutant 1463V/A SEQ ID NO: 27 | ACELPECQEDAGNKACSLQCNNHACGWDGGDCSLNFNDPWKN | 6% | 56% |
| Mutant 1465S/N SEQ ID NO: 28 | ACELPECQEDAGNKVCNLQCNNHACGWDGGDCSLNFNDPWKN | 8% | 109% |
| Mutant 1466L/A SEQ ID NO: 29 | ACELPECQEDAGNKVCSAQCNNHACGWDGGDCSLNFNDPWKN | 1% | 4% |
| Mutant 1467Q/A SEQ ID NO: 30 | ACELPECQEDAGNKVCSLQCNNHACGWDGGDCSLNFNDPWKN | 4% | 16% |

Identify Binding Epitope of N248A1 in HD-C Domain

A serial of five sub-domain swap chimeric antigens (Table 6) were generated by sequentially swapping clusters of amino acids from Notch1 sequence to Notch2 sequence. ELISA results showed that the sub-domain swap-1 significantly reduced N248A1 binding while the other four subdomain swap antigens does not affect N248A1 binding. On the other hand, the parallel control mAb 19H7 showed significant binding affinity reduction on sub-domain swap 1, 3 and 5 (Table 6). All the subdomain swap antigen expression and secretion in conditioned media was confirmed by Western blot analysis (Methods in above). All subdomain swap antigens except subdomain swap 5 have equal or higher expression than human Notch1-NRRHD (huN1-NRRHD) protein. The subdomain swap 5 expressed at about 50% level of huN1-NRRHD based on Western blot band intensity comparison (data not shown). These experiments showed that the binding epitope of N248A1 in HD-C includes five amino acids, 1705G, 1706A, 1707L, 1709S and 1710L (human Notch1 coding cDNA sequence, NCBI accession # NM_017617), as highlighted in Table 6.

TABLE 6

ELISA readings of Notch1 mAbs binding to human Notch1-NRRHD and chimeric antigens with subdomain swapped to Notch2 sequences

| Antigens | Sequence of HD-C | Binding activity N248A1 | Binding activity 19H7 |
|---|---|---|---|
| huN1-NRRHD SEQ ID NO: 31 | FLGALASLGSLNIPYKIEAVQSETVEPPPPAQKRR | 3.05 | 2.92 |
| Subdomain swap 1 SEQ ID NO: 32 | FLASHAIQG | 0.48 | 0.48 |
| Subdomain swap 2 SEQ ID NO: 33 | GTLNISYPI | 2.76 | 2.51 |
| Subdomain swap 3 SEQ ID NO: 34 | KLVSVVSE | 2.81 | 0.2 |
| Subdomain swap 4 SEQ ID NO: 36 | ESLETPP | 2.89 | 2.62 |
| Subdomain swap 5 SEQ ID NO: 37 | PERTQKSR | 1.48 | 0.62 |

Example 6

Notch1 mAb Inhibits Cancer Cell Growth in Cell Culture

Inhibition of HPB-ALL Leukemia Cells Growth and Reduction of NICD by mAb N248A

The T-cell acute lymphoblastic leukemia (T-ALL) cell line, HPB-ALL, was derived from a childhood T-ALL (Morikawa et al., Int J. Cancer, 1978, 21(2):166-70), and obtained from DSMZ (Braunschweig, Germany). This cell line harbors a Notch1 mutation that leads to high level of Notch1 intracellular domain (NICD), the active form of Notch1, as a result of enhanced gamma secretase cleavage. For growth inhibition assays, HPB-ALL cells were seeded in 96-well plates at 10,000 cell/well in RPMI1640 media supplemented with 10% FBS (Invitrogen). Serially diluted mAb N248A or D16A was added at beginning, and cells were cultured at 37° C. for 7 day. At the end of the culture, phosphate buffered saline (PBS) containing 0.1 mg/ml of Resazurin (Sigma-Aldrich, St. Louis, Mo.) was added to the cells, and the plates were incubated at 37° C. for 4 hours. Fluorescent signals were read through dual filters with excitation=560 nm and emission=590 nm. $IC_{50}$ values were calculated using the sigmoidal dose-response (variable slope) in GraphPad Prism (GraphPad Software, Inc., La Jolla, Calif.).

For in vitro NICD analysis, HPB-ALL cells were seeded in 6-well plates at $2\times10^6$ cells per well and cultured in RPMI1640 with 10% FCS (Invitrogen). mAb N248A or control antibody D16A was added to the culture at variable concentrations as indicated in FIG. 6. Cells were cultured in the presence of antibodies at 37° C. for 24 hours. They were then collected and lysed in cold 1× Cell Lysis Buffer (Cell Signaling Technologies, Boston Mont.). Proteins were extracted from cell lysate by centrifuging at 13,000 rpm for 10 minute at 4° C. Protein concentrations were determined using a BCA assay (Pierce, Rockford, Ill.). The level of NICD in each sample was determined by western blot analysis.

In each western blot analysis, about 50 μg of lysate was resolved by electrophoresis through a polyacrylamide gel (BioRad Laboratories, Hercules, Calif.), and transferred to nitrocellulose membrane, which was subjected to immunoblot analysis using rabbit anti-NICD antibody (Cell Signaling Technology, Inc., Danvers, Mass.) and mouse a actin antibody (Sigma-Aldrich, St. Louis, Mo.). IRDye 680 or 800 conjugated secondary antibodies (LI-COR Biosciences, Lincoln, Nebr.) were used to visualize the Western blot bands. The images were analyzed using Odyssey Infrared Imaging System (LI-COR Biosciences, Lincoln, Nebr.).

The results demonstrated that inhibition of HPB-ALL cell growth by mAb N248A is correlated to the reduction of NICD levels. At 24 hours of treatment, mAb N248A reduced NICD levels in a dose dependent manner, the highest reduction was observed at 30 μg/mL. After 7 days of treatment, mAb N248A caused significant inhibition of cell growth. IC50 value for the cell growth inhibition is approximately 0.78 μg/ml or ~5.2 nM.

Inhibition of Breast Cancer Cell Growth

It was well documented that expression of Notch1 was aberrantly increased in breast cancer (Reedijk et al. Cancer Research, 2005, 65(18):8530-8537; Klinakis et al., 2006; Efstratiadis et al., Cell Cycle, 2007, 6(4):418-429) which was associated to poor survival rate (Reedijk et al. Cancer Research, 2005, 65(18):8530-8537). In transgenic mice expressing the activated form of Notch1 in mammary tissue, almost all the mice developed breast cancer by one year (Hu et al., American Journal of Pathology, 2006, 168(3):973-990). To test the hypothesis that blocking Notch1-mediated signaling would inhibits breast cancer cell growth, several breast cancer cell lines were cultured in presence of 10 μg/ml mAb N248A antibody, Herceptin (Genentech/Roche, South San Francisco, Calif.) or control mouse immunoglobulin G (mIgG). All the cells were cultured in RPMI 1640 (Invitrogen) with 1% FCS for two to three days. The viable cells was quantified by Cell Titer Glow™ (Promega), and scanned by MicroLumat Plus LB 96V luminometer (Berthhold Technologies, Bad Wildbad, Germany). To the same panel of breast cancer cells, expression of Notch1 and Jagged1 on cell surface was analyzed by FACS. The results demonstrated that the growth inhibition of the breast cancer cells by mAb N248A is roughly correlated to Notch1 and Jagged1 expression level. mAb N248A exerts the strongest inhibition to MDA-MB-231 cells, which expresses relatively high level of Notch1 and Jagged1. Interestingly, BT475 cell-derived, Heceptin-resistant cell line, BT475HR, showed increased expression of Notch1 and Jagged1 comparing to parental BT475 cell line. mAb N248A inhibited BT475HR cell growth, while Heceptin did not. The data indicated potential utility of mAb N248A in therapeutic treatment of breast cancer which has increased expression of Notch1 or resistant to current drug, Heceptin.

Table 7. Tumor cell growth inhibition assay of anti-Notch1 mAb, N248A. Expression index represents fold increase of FACS geometric mean after the breast cancer cells were immuno-stained with anti-Notch1 or anti-Jagged1 antibody. Relative cell proliferation index stands for percentage of control cell cultured in parallel without adding any agent. BT-474HR is Herceptin-resistant cell line derived from BT-474 (ATCC).

TABLE 7

| Cell Lines | Expression index | | Relative cell proliferation index | | |
|---|---|---|---|---|---|
| | Notch1 | Jagged1 | N248A | Herceptin | mIgG |
| MDA-MB-231 | 1.7 | 4.4 | 69 | 96 | 103 |
| BT-474HR | 2.5 | 3.0 | 80 | 97 | 99 |
| HCC38 | 1.5 | 1.8 | 86 | 97 | 99 |
| HCC1954 | 1.5 | 1.8 | 88 | 94 | 99 |
| SKBR3 | 1.6 | 1.2 | 97 | 84 | 107 |
| BT-474 | 1.4 | 1.0 | 98 | 68 | 98 |
| MCF7 | 1.2 | 1.1 | 98 | 101 | 95 |
| BT549 | 1.1 | 1.1 | 115 | 103 | 112 |

To confirm that the growth inhibition of breast cancer cell by N248A is mediated by block Notch signaling, the expression of two well-known Notch down-stream target genes was assessed by quantitative reverse transcriptase-polymerase chain reaction (QRT-PCR). MDA-MB-231 cells were cultured in presence of N248A or control mAb for two days, and then harvested to isolate total RNA using RNAeasy reagent kit and protocol (Qiagen). The results demonstrated that mAb N248A indeed blocked HES1 and HES4 expression (FIG. 7), confirming the mechanism of action by N248A.

Example 7

Notch1 mAb Inhibits T-Cell Acute Lymphoblastic Leukemia (T-ALL) in Murine Xenograft Tumor Model T-ALL tumor Growth Inhibition by Notch1 mAb For establishing mouse model T-ALL xenograft model, immune-compromised athymic female Nude (Nu/Nu) mice (average at 20 grams, 6-8 weeks old), were obtained from Charles River Laboratories (Wilmington, Mass.) and housed in specific pathogen-free conditions following the guidelines of the Association for the Assessment and Accreditation for Laboratory Animal Care, International. Animals were provided sterile rodent chow and water ad libitum. All in vivo studies were carried out under approved institutional experimental animal care and use protocols.

HBP-ALL Cells were harvested from fresh culture before implanting in host mice, and washed once and re-suspended in sterile, serum-free medium. The cell suspension was adjusted appropriate density and supplemented with 50% Matrigel (BD Biosciences, San Jose, Calif.) to facilitate tumor take. A total of 5–10×10$^6$ cells in 200 μL were implanted subcutaneously into the hind-flank region of the mouse and allowed to grow to the designated size prior to the administration of antibody for each experiment.

For anti-tumor efficacy study, animals bearing HPB-All tumors of 150-300 mm$^3$ in size were randomized and divided into four groups receiving N248A at 1 mg, 3 mg and 10 mg per kilogram (kg) respectively, or receiving control antibody D16A at 5 mg per kg. The mAbs were injected subcutaneously once a week for 2 weeks. Animal body weight and tumor measurements were obtained every 2-3 days. Tumor volume (mm$^3$) was measured with Vernier calipers and calculated using the formula: length (mm)×width (mm)×width (mm)×0.4. The tumor volumes of drug-treated and vehicle-treated mice on the final day of study were used to calculate percent (5) inhibition values as $100-\{1-[(\text{Treated}_{Final\ day}-\text{Treated}_{Day\ 1})/(\text{Control}_{Final\ day}-\text{Control}_{Day\ 1})]\}$. For all tumor growth inhibition (TGI) experiments, 8 to 10 mice per dose group were used. A Student's t test was used to determine the P.

As shown in FIG. 8, Notch1 mAb, N248A, demonstrated robust antitumor activity in this model after 11 days' treatment, i.e. two weekly doses. The average tumor growth inhibition (TGI) in the 10 mg/kg group versus control mAb group is more than 77%, which is highly significant in statistical term (P<0.01). TGI was roughly dose-dependent with an exception that the two lower dose groups, 1 mg/kg and 3 mg/kg, are too close to differentiate. The exact causes for this observation are unclear though it is likely due to high variability in tumor size of this model. N248A, as a human Notch1-specific inhibitor, was well-tolerated in mice, without causing significant weight loss, morbidity or mortality in any treatment groups.

Pharmacokinetics and Pharmacodynamics (PK/PD) of Notch1 mAb in Mice

For PK/PD study, mice bearing tumors with size ranging 300-800 mm$^3$ were administered a single dose of N248A at 5 mg/kg by subcutaneous injection. After administration of N248A mice were euthanized at time points of 6, 16 hours, and 1, 2, 3, 5 days. Blood samples were drawn from the left cardiac ventricle using a syringe and transferred to tubes primed with heparin sulfate. In the meantime, the tumors were taken out by resection, snap-frozen and homogenized in cold 1× Cell Lysis Buffer (Cell Signaling Technologies, Boston Mont.). Proteins were extracted from the tumor lysate and the level of NICD in each tumor sample was determined using western blot analysis described above. The blood samples were subject to centrifugation to separate serum from blood cells. The serum level of N248A was assessed by ELISA method as described in Example 2. The ELISA plate was first coated with human Fc-specific mAb, which captures Notch1-NRR-TM(−)/Fc antigen. The Notch1 antigen in turn binds to Notch1 mAb, N248A, in sera.

The PK curve indicated that N248A mAb reached maximum concentration (~235 nM) in mouse sera 24 hours after injection. The estimated half life is about 4.5 days (FIG. 9). Evaluation of the direct marker for Notch1 activation (i.e. NICD) showed that the tumor samples harvested from mice treated with N248A had a robust NICD reduction, which persisted until five days post dosing (FIG. 10). In contrast, the control mAb, D16A, did not reduce NICD level (data not shown). The maximal inhibition of NICD by N248A at 5 mg/kg was approximately 80%.

Example 8

Cloning and Sequences of Notch1 mAb, N248A

The sequences of the variable regions of mAb N248A was determined. The antibody IgG subtype was first assessed using an Isostrip Mouse Monoclonal Antibody kit (Roche Diagnostics, Indianapolis, Ind.). The results indicated that N248A has an $IgG_1$ heavy chain and a lambda light chain. For cloning and sequencing of mAb N248A, $1 \times 10^6$ hybridoma cells were harvested and lysed to isolate total cellular RNA using RNeasy Mini Reagent kit and manufacturer's protocol (Qiagen, Valencia, Calif.). The first strand cDNA was synthesized on the RNA templates using Superscript III reverse transcriptase (InVitrogen). The cDNAs of the variable regions of light chain and heavy chain were amplified by PCR from the first strand cDNA using degenerate forward primers complimentary to the 5'-end of mouse lambda chain coding sequence and a reverse primer matching the constant region adjacent to the 3'-end of the variable region, or using degenerate forward primers complementary to the 5'-end of mouse IgG1 heavy chain coding sequence and a respective IgG1 constant region reverse primer. PCR cycling conditions were as follows: 1 cycle at 96 C for 1 minute, followed by 40 cycles at 95° C. for 20 sec, 50° C. for 20 sec, and 72° C. for 30 second. The resulting PCR products were cloned into pCR-4-TOPO vector (Invitrogen), sequenced by conventional methods, and analyzed using Vector NTI Advance software, (InVitrogen). The cloned antibody sequences were confirmed by direct comparison with the N-terminal sequences obtained from purified hybridoma-derived antibody, as determined by Mass spectrometry (Univ. of CA, Davis, Molecular Structure Facility). The compiled sequence results demonstrated that the variable region of mAb N248A heavy chain contains 121 amino acid residues, and the light chain contains 109 amino acid residues. Further analysis of the N248A mAb $V_H$ sequence and $V_L$ sequence using the Kabat system of CDR region determination led to the delineation of the heavy chain CDR1, CDR2 and CDR3 and light change CDR1, CDR2 and CDR3. The nucleotide and amino acid sequences of the heavy chain variable region CDR1, CDR2 and CDR3 of mAb N248A are shown as sequences 15-20 (SEQ ID NO: 15-20). The nucleotide and amino acid sequences of the light chain variable region CDR1, CDR2 and CDR3 of mAb N248A are shown as sequences 9-14 (SEQ ID NO: 9-14). The nucleotide and amino acid sequences of the heavy chain variable region and light chain variable region of mAb N248A are shown as sequences 5-8 (SEQ ID NO: 5-8).

What is claimed is:

1. An isolated antibody, or an antigen binding portion thereof, that specifically binds to human Notch-1, wherein the antibody or antigen binding portion binds to at least a first epitope and a second epitope;
wherein the first epitope comprises 1 to 4 amino acid residues selected from amino acid residues 15, 17, 18, and 19 of SEQ ID NO: 23; and
wherein the second epitope comprises 1 to 5 amino acid residues of SEQ ID NO: 31.

2. The antibody or the antigen binding portion of claim 1, wherein the antibody or the antigen binding portion is humanized, human, or chimeric.

3. The antibody or the antigen binding portion of claim 1, wherein the antibody or the antigen binding portion is a mouse antibody.

4. An isolated antibody, or an antigen binding portion thereof, that specifically binds to human Notch-1, wherein the antibody or antigen binding portion binds to at least a first epitope and a second epitope;
wherein the first epitope comprises 1 to 4 amino acid residues of SEQ ID NO: 23; and
wherein the second epitope comprises 1 to 5 amino acid residues selected from amino acid residues 3, 4, 5, 7, and 8 of SEQ ID NO: 31.

5. The antibody or the antigen binding portion of claim 4, wherein the antibody or the antigen binding portion is humanized, human, or chimeric.

6. The antibody or the antigen binding portion of claim 4, wherein the antibody or the antigen binding portion is a mouse antibody.

7. An isolated antibody, or an antigen binding portion thereof, that specifically binds to human Notch-1, comprising:

(i) a heavy chain variable region CDR1 comprising the amino acid sequence of SEQ ID NO: 18,
(ii) a heavy chain variable region CDR2 comprising the amino acid sequence of SEQ ID NO: 19,
(iii) a heavy chain variable region CDR3 comprising the amino acid sequence of SEQ ID NO: 20,
(iv) a light chain variable region CDR1 comprising the amino acid sequence of SEQ ID NO: 12,
(v) a light chain variable region CDR2 comprising the amino acid sequence of SEQ ID NO: 13, and
(vi) a light chain variable region CDR3 comprising the amino acid sequence of SEQ ID NO: 14.

8. The antibody or the antigen binding portion of claim 7, wherein the antibody or the antigen binding portion is humanized, human, or chimeric.

9. The antibody or the antigen binding portion of claim 7, wherein the antibody or the antigen binding portion is a mouse antibody.

10. A method for treating cancer in a subject in need thereof comprising administering a therapeutically effective amount of the antibody or the antigen binding portion of any one of claims 1, 4, 2, 3, 7, 8, 5, 6, and 9, or a pharmaceutical composition thereof, and wherein the cancer is T-cell acute lymphoblastic leukemia (T-ALL) or breast cancer.

11. The method according to claim 10, wherein said method comprises administering a therapeutically effective amount of the antibody or the antigen binding portion of any one of claims 1, 2 and 3, or a pharmaceutical composition thereof.

12. The method according to claim 10, wherein said method comprises administering a therapeutically effective amount of the antibody or the antigen binding portion of any one of claims 4, 5, and 6, or a pharmaceutical composition thereof.

* * * * *

SEQUENCE LISTING

```
<160> NUMBER OF SEQ ID NOS: 38

<210> SEQ ID NO 1
<211> LENGTH: 1347
<212> TYPE: DNA
<213> ORGANISM: Artificial Sequence
<220> FEATURE:
<223> OTHER INFORMATION: Synthetic

<400> SEQUENCE: 1
atgccgccgc tcctggcacc tctgctctgc ctggcactgc tacccgctct cgctgcacga      60
ggtccgcgat gctcccaacc aggtgagacc tgcctgaatg gaggtaagtg tgaagcagcc     120
aatggcacgt gcctgtgcct gggcccttc acgggccccg aatgccagtt cccggccagc     180 agccctgcc tgggcggcaa cccctgctac aaccagggga cctgtgagcc cacatccgag     240
agccccttct accgttgcct gtgccccgcc aaattcaacg ggctcttgtg ccacatcctg     300
gactacagct tcggggtgg ggccgggcgc gacatccccc gccgctgat cgaggaggcg     360 tgcgagctgc ccgagtgcca ggaggacgcg ggcaacaagg tctgcagcct gcagtgcaac     420
aaccacgcgt gcggctggga cggcggtgac tgctccctca acttcaatga ccctggaag     480 aactgcacgc agtctctgca gtgctggaag tacttcagtg acgccactg tgacagccag     540 tgcaactcag ccggctgcct cttcgacggc tttgactgcc agcgtgcgga aggccagtgc     600
aaccccctgt acgaccagta ctgcaaggac cacttcagcg acgggcactg cgaccagggc     660
tgcaacagcg cggagtgcga gtgggacggg ctggactgtg cggagcatgt acccgagagg     720
```

```
ctggcggccg gcacgctggt ggtggtggtg ctgatgccgc cggagcagct gcgcaacagc    780
tccttccact cctgcggga gctcagccgc gtgctgcaca ccaacgtggt cttcaagcgt    840
gacgcacacg gccagcagat gatcttcccc tactacggcc gcgaggagga gctgcgcaag    900
caccccatca agcgtgccgc cgagggctgg gccgcacctg acgccctgct gggccaggtg    960
aaggcctcgc tgctccctgg tggcagcgag ggtgggcggc ggcggaggga gctggacccc   1020
atggacgtcc gcggctccat cgtctacctg gagattgaca accggcagtg tgtgcaggcc   1080
tcctcgcagt gcttccagag tgccaccgac gtggccgcat cctgggagc gctcgcctcg    1140 ctgggcagcc tcaacatccc ctacaagatc gaggccgtgc agagtgagac cgtggagccg   1200
cccccgccgg cgcagaagcg ccggcggcag catggccagc tctggttccc tgagggcttc   1260
aaagtgtctg aggccagcaa gaagaagcgg cgggagcccc tcggcgagga ctccgtgggc   1320
ctcaagcccc tgaagaacgc ttcagac                                       1347
```

<210> SEQ ID NO 2
<211> LENGTH: 449
<212> TYPE: PRT
<213> ORGANISM: Artificial Sequence
<220> FEATURE:
<223> OTHER INFORMATION: Synthetic

<400> SEQUENCE: 2

```
Met Pro Pro Leu Leu Ala Pro Leu Leu Cys Leu Ala Leu Leu Pro Ala
1               5                   10                  15

Leu Ala Ala Arg Gly Pro Arg Cys Ser Gln Pro Gly Glu Thr Cys Leu
            20                  25                  30

Asn Gly Gly Lys Cys Glu Ala Ala Asn Gly Thr Cys Leu Cys Leu Gly
        35                  40                  45

Pro Phe Thr Gly Pro Glu Cys Gln Phe Pro Ala Ser Ser Pro Cys Leu
    50                  55                  60

Gly Gly Asn Pro Cys Tyr Asn Gln Gly Thr Cys Glu Pro Thr Ser Glu
65                  70                  75                  80

Ser Pro Phe Tyr Arg Cys Leu Cys Pro Ala Lys Phe Asn Gly Leu Leu
                85                  90                  95

Cys His Ile Leu Asp Tyr Ser Phe Gly Gly Ala Gly Arg Asp Ile
            100                 105                 110

Pro Pro Leu Ile Glu Glu Ala Cys Glu Leu Pro Glu Cys Gln Glu
        115                 120                 125

Asp Ala Gly Asn Lys Val Cys Ser Leu Gln Cys Asn Asn His Ala Cys
    130                 135                 140

Gly Trp Asp Gly Gly Asp Cys Ser Leu Asn Phe Asn Asp Pro Trp Lys
145                 150                 155                 160

Asn Cys Thr Gln Ser Leu Gln Cys Trp Lys Tyr Phe Ser Asp Gly His
                165                 170                 175

Cys Asp Ser Gln Cys Asn Ser Ala Gly Cys Leu Phe Asp Gly Phe Asp
            180                 185                 190

Cys Gln Arg Ala Glu Gly Gln Cys Asn Pro Leu Tyr Asp Gln Tyr Cys
        195                 200                 205

Lys Asp His Phe Ser Asp Gly His Cys Asp Gln Gly Cys Asn Ser Ala
    210                 215                 220

Glu Cys Glu Trp Asp Gly Leu Asp Cys Ala Glu His Val Pro Glu Arg
225                 230                 235                 240

Leu Ala Ala Gly Thr Leu Val Val Val Val Leu Met Pro Pro Glu Gln
                245                 250                 255
```

Leu Arg Asn Ser Ser Phe His Phe Leu Arg Glu Leu Ser Arg Val Leu
            260                 265                 270

His Thr Asn Val Val Phe Lys Arg Asp Ala His Gly Gln Gln Met Ile
        275                 280                 285

Phe Pro Tyr Tyr Gly Arg Glu Glu Leu Arg Lys His Pro Ile Lys
    290                 295                 300

Arg Ala Ala Glu Gly Trp Ala Ala Pro Asp Ala Leu Leu Gly Gln Val
305                 310                 315                 320

Lys Ala Ser Leu Leu Pro Gly Gly Ser Glu Gly Arg Arg Arg
                325                 330                 335

Glu Leu Asp Pro Met Asp Val Arg Gly Ser Ile Val Tyr Leu Glu Ile
            340                 345                 350

Asp Asn Arg Gln Cys Val Gln Ala Ser Ser Gln Cys Phe Gln Ser Ala
        355                 360                 365

Thr Asp Val Ala Ala Phe Leu Gly Ala Leu Ala Ser Leu Gly Ser Leu
    370                 375                 380

Asn Ile Pro Tyr Lys Ile Glu Ala Val Gln Ser Glu Thr Val Glu Pro
385                 390                 395                 400

Pro Pro Pro Ala Gln Lys Arg Arg Gln His Gly Gln Leu Trp Phe
                405                 410                 415

Pro Glu Gly Phe Lys Val Ser Glu Ala Ser Lys Lys Arg Arg Glu
            420                 425                 430

Pro Leu Gly Glu Asp Ser Val Gly Leu Lys Pro Leu Lys Asn Ala Ser
        435                 440                 445

Asp

<210> SEQ ID NO 3
<211> LENGTH: 1287
<212> TYPE: DNA
<213> ORGANISM: Artificial Sequence
<220> FEATURE:
<223> OTHER INFORMATION: Synthetic

<400> SEQUENCE: 3
atgcctccgc tcctggcacc tctgctctgc ctggcactgc tacccgctct cgctgcacga      60
ggtccgcgat gctcccaacc aggtgagacc tgcctgaatg gaggtaagtg tgaagcagcc     120
aatggcacgt gcctgtgcct gggcccctcc acgggccccg aatgccagtt cccggccagc     180
agcccctgcc tgggcggcaa ccctgctac aaccagggga cctgtgagcc acatccgag      240 agcccttct accgttgcct gtgccccgcc aaattcaacg gctcttgtg ccacatcctg      300 gactacagct tcggggtgg ggccgggcgc gacatccccc gccgctgat cgaggaggcg     360 tgcgagctgc ccgagtgcca ggaggacgcg ggcaacaagg tctgcagcct gcagtgcaac     420
aaccacgcgt gcggctggga cggcggtgac tgctccctca acttcaatga ccctggaag     480 aactgcacga gtctctgca gtgctggaag tacttcagtg acggccactg tgacagccag     540
tgcaactcag ccggctgcct cttcgacggc tttgactgcc agcgtgcgga aggccagtgc     600 aacccccctgt acgaccagta ctgcaaggac cacttcagcg acgggcactg cgaccagggc     660
tgcaacagcg cggagtgcga gtgggacggg ctggactgtg cggagcatgt acccgagagg     720
ctggcggccg gcacgctggt ggtggtggtg ctgatgccgc cggagcagct cgcaacagc      780 tccttccact cctgcgggga gctcagccgc gtgctgcaca ccaacgtggt cttcaagcgt     840
gacgcacacg gccagcagat gatcttcccc tactacggcc gcgaggagga gctgcgcaag     900

```
cacccccatca agcgtgccgc cgagggctgg gccgcacctg acgccctgct gggccaggtg    960
aaggcctcgc tgctccctgg tggcagcgag ggtgggcggc ggcggaggga gctggacccc   1020
atggacgtcc gcggctccat cgtctacctg agagattgaca accggcagtg tgtgcaggcc   1080
tcctcgcagt gcttccagag tgccaccgac gtggccgcat tcctgggagc gctcgcctcg   1140
ctgggcagcc tcaacatccc ctacaagatc gaggccgtgc agagtgagac cgtggagccg   1200 ccccccgccgg cgcagctgca cttcatgtac gtggcggcgg ccgcctttgt gcttctgttc   1260
ttcgtgggct gcggggtgct gctgtcc                                       1287
```

<210> SEQ ID NO 4
<211> LENGTH: 429
<212> TYPE: PRT
<213> ORGANISM: Artificial Sequence
<220> FEATURE:
<223> OTHER INFORMATION: Synthetic

<400> SEQUENCE: 4

```
Met Pro Pro Leu Leu Ala Pro Leu Leu Cys Leu Ala Leu Leu Pro Ala
1               5                   10                  15

Leu Ala Ala Arg Gly Pro Arg Cys Ser Gln Pro Gly Glu Thr Cys Leu
            20                  25                  30

Asn Gly Gly Lys Cys Glu Ala Ala Asn Gly Thr Cys Leu Cys Leu Gly
        35                  40                  45

Pro Phe Thr Gly Pro Glu Cys Gln Phe Pro Ala Ser Ser Pro Cys Leu
    50                  55                  60

Gly Gly Asn Pro Cys Tyr Asn Gln Gly Thr Cys Glu Pro Thr Ser Glu
65                  70                  75                  80

Ser Pro Phe Tyr Arg Cys Leu Cys Pro Ala Lys Phe Asn Gly Leu Leu
                85                  90                  95

Cys His Ile Leu Asp Tyr Ser Phe Gly Gly Ala Gly Arg Asp Ile
            100                 105                 110

Pro Pro Pro Leu Ile Glu Glu Ala Cys Glu Leu Pro Glu Cys Gln Glu
        115                 120                 125

Asp Ala Gly Asn Lys Val Cys Ser Leu Gln Cys Asn Asn His Ala Cys
    130                 135                 140

Gly Trp Asp Gly Gly Asp Cys Ser Leu Asn Phe Asn Asp Pro Trp Lys
145                 150                 155                 160

Asn Cys Thr Gln Ser Leu Gln Cys Trp Lys Tyr Phe Ser Asp Gly His
                165                 170                 175

Cys Asp Ser Gln Cys Asn Ser Ala Gly Cys Leu Phe Asp Gly Phe Asp
            180                 185                 190

Cys Gln Arg Ala Glu Gly Gln Cys Asn Pro Leu Tyr Asp Gln Tyr Cys
        195                 200                 205

Lys Asp His Phe Ser Asp Gly His Cys Asp Gln Gly Cys Asn Ser Ala
    210                 215                 220

Glu Cys Glu Trp Asp Gly Leu Asp Cys Ala Glu His Val Pro Glu Arg
225                 230                 235                 240

Leu Ala Ala Gly Thr Leu Val Val Val Leu Met Pro Pro Glu Gln
                245                 250                 255

Leu Arg Asn Ser Ser Phe His Phe Leu Arg Glu Leu Ser Arg Val Leu
            260                 265                 270

His Thr Asn Val Val Phe Lys Arg Asp Ala His Gly Gln Gln Met Ile
        275                 280                 285

Phe Pro Tyr Tyr Gly Arg Glu Glu Glu Leu Arg Lys His Pro Ile Lys
```

```
                  290                 295                 300

Arg Ala Glu Gly Trp Ala Ala Pro Asp Ala Leu Gly Gln Val
305                 310                 315                 320

Lys Ala Ser Leu Leu Pro Gly Gly Ser Glu Gly Arg Arg Arg
                325                 330                 335

Glu Leu Asp Pro Met Asp Val Arg Gly Ser Ile Val Tyr Leu Glu Ile
                340                 345                 350

Asp Asn Arg Gln Cys Val Gln Ala Ser Gln Cys Phe Gln Ser Ala
                355                 360                 365

Thr Asp Val Ala Ala Phe Leu Gly Ala Leu Ala Ser Leu Gly Ser Leu
            370                 375                 380

Asn Ile Pro Tyr Lys Ile Glu Ala Val Gln Ser Glu Thr Val Glu Pro
385                 390                 395                 400

Pro Pro Pro Ala Gln Leu His Phe Met Tyr Val Ala Ala Ala Phe
                405                 410                 415

Val Leu Leu Phe Phe Val Gly Cys Gly Val Leu Leu Ser
                420                 425

<210> SEQ ID NO 5
<211> LENGTH: 363
<212> TYPE: DNA
<213> ORGANISM: Mus musculus

<400> SEQUENCE: 5
caggttcagc tgcagcagtc tggagctgag ctgatgaagc ctggggcctc agtgaagata    60
tcctgcaagg ctactggcta cacattcagt aactactgga tggagtgggt aaagcagagg   120
cctggacatg gccttgagtg gattggagag attttacctg aaggggtag aactaactac   180 aatgagaact tcaagggcaa ggccacattc actgcagata catcctccaa cacagtctac   240
atgcaactca cagcctgaca tctgaggac tctgccgtct attactgtgc aagattccac   300
agctcggcct attactatac tatggactac tggggtcaaa gaacctcggt caccgtctcc   360
tca                                                                  363

<210> SEQ ID NO 6
<211> LENGTH: 121
<212> TYPE: PRT
<213> ORGANISM: Mus musculus

<400> SEQUENCE: 6

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Asn Tyr
                20                  25                  30

Trp Met Glu Trp Val Lys Gln Arg Pro Gly His Gly Leu Glu Trp Ile
            35                  40                  45

Gly Glu Ile Leu Pro Gly Arg Gly Arg Thr Asn Tyr Asn Glu Asn Phe
        50                  55                  60

Lys Gly Lys Ala Thr Phe Thr Ala Asp Thr Ser Ser Asn Thr Val Tyr
65                  70                  75                  80

Met Gln Leu Asn Ser Leu Thr Ser Glu Asp Ser Ala Val Tyr Tyr Cys
                85                  90                  95

Ala Arg Phe His Ser Ser Ala Tyr Tyr Tyr Thr Met Asp Tyr Trp Gly
                100                 105                 110

Gln Arg Thr Ser Val Thr Val Ser Ser
            115                 120
```

<210> SEQ ID NO 7
<211> LENGTH: 327
<212> TYPE: DNA
<213> ORGANISM: Mus musculus

<400> SEQUENCE: 7
caggctgttg tgactcagga atctgcactc accacatcac ctggtgaaac agtcacactc    60
acttgtcgct caagtactgg ggctgttaca actagtaact atgccaactg gtccaagaa    120 aaaccagatc atttattcac tggtctaata ggtggtacca caaccgagc tccaggtatt    180 cctgccagat tctcaggctc cctgattgga gacaaggctg ccctcaccat cacagggca    240 cagactgagg atgaggcaat atatttctgt gctctatggt acagcaacca ctgggtgttc    300
ggtggaggaa ccaaactgac tgtccta                                       327

<210> SEQ ID NO 8
<211> LENGTH: 109
<212> TYPE: PRT
<213> ORGANISM: Mus musculus

<400> SEQUENCE: 8

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Asn Arg Ala Pro Gly Ile Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Lys Leu Thr Val Leu
            100                 105

<210> SEQ ID NO 9
<211> LENGTH: 42
<212> TYPE: DNA
<213> ORGANISM: Mus musculus

<400> SEQUENCE: 9
cgctcaagta ctggggctgt tacaactagt aactatgcca ac                       42

<210> SEQ ID NO 10
<211> LENGTH: 21
<212> TYPE: DNA
<213> ORGANISM: Mus musculus

<400> SEQUENCE: 10
ggtaccaaca accgagctcc a                                              21

<210> SEQ ID NO 11
<211> LENGTH: 27
<212> TYPE: DNA
<213> ORGANISM: Mus musculus

<400> SEQUENCE: 11
gctctatggt acagcaacca ctgggtg                                        27

<210> SEQ ID NO 12
<211> LENGTH: 14
<212> TYPE: PRT
<213> ORGANISM: Mus musculus

<400> SEQUENCE: 12

Arg Ser Ser Thr Gly Ala Val Thr Thr Ser Asn Tyr Ala Asn
1               5                   10

<210> SEQ ID NO 13
<211> LENGTH: 7
<212> TYPE: PRT
<213> ORGANISM: Mus musculus

<400> SEQUENCE: 13

Gly Thr Asn Asn Arg Ala Pro
1               5

<210> SEQ ID NO 14
<211> LENGTH: 9
<212> TYPE: PRT
<213> ORGANISM: Mus musculus

<400> SEQUENCE: 14

Ala Leu Trp Tyr Ser Asn His Trp Val
1               5

<210> SEQ ID NO 15
<211> LENGTH: 15
<212> TYPE: DNA
<213> ORGANISM: Mus musculus

<400> SEQUENCE: 15
aactactgga tggag                                                     15

<210> SEQ ID NO 16
<211> LENGTH: 51
<212> TYPE: DNA
<213> ORGANISM: Mus musculus

<400> SEQUENCE: 16
gagattttac ctggaagggg tagaactaac tacaatgaga acttcaaggg c              51

<210> SEQ ID NO 17
<211> LENGTH: 36
<212> TYPE: DNA
<213> ORGANISM: Mus musculus

<400> SEQUENCE: 17
ttccacagct cggcctatta ctatactatg gactac                              36

<210> SEQ ID NO 18
<211> LENGTH: 5
<212> TYPE: PRT
<213> ORGANISM: Mus musculus

<400> SEQUENCE: 18

Asn Tyr Trp Met Glu
1               5

<210> SEQ ID NO 19
<211> LENGTH: 17
<212> TYPE: PRT

<213> ORGANISM: Mus musculus

<400> SEQUENCE: 19

Glu Ile Leu Pro Gly Arg Gly Arg Thr Asn Tyr Asn Glu Asn Phe Lys
1               5                   10                  15

Gly

<210> SEQ ID NO 20
<211> LENGTH: 12
<212> TYPE: PRT
<213> ORGANISM: Mus musculus

<400> SEQUENCE: 20

Phe His Ser Ser Ala Tyr Tyr Tyr Thr Met Asp Tyr
1               5                   10

<210> SEQ ID NO 21
<211> LENGTH: 864
<212> TYPE: DNA
<213> ORGANISM: Homo sapiens

<400> SEQUENCE: 21
gaggaggcgt gcgagctgcc cgagtgccag gaggacgcgg gcaacaaggt ctgcagcctg     60
cagtgcaaca accacgcgtg cggctgggac ggcggtgact gctccctcaa cttcaatgac    120
ccctggaaga actgcacgca gtctctgcag tgctggaagt acttcagtga cggccactgt    180
gacagccagt gcaactcagc cggctgcctc ttcgacggct tgactgcca gcgtgcggaa     240 ggccagtgca accccctgta cgaccagtac tgcaaggacc acttcagcga cgggcactgc    300
gaccagggct gcaacagcgc ggagtgcgag tgggacgggc tggactgtgc ggagcatgta    360
cccgagaggc tggcggccgg cacgctggtg gtggtggtgc tgatgccgcc ggagcagctg    420
cgcaacagct ccttccactt cctgcgggag ctcagccgcg tgctgcacac caacgtggtc    480
ttcaagcgtg acgcacacgg ccagcagatg atcttcccct actacggccg cgaggaggag    540
ctgcgcaagc accccatcaa gcgtgccgcc gagggctggg ccgcacctga cgccctgctg    600
ggccaggtga aggcctcgct gctccctggt ggcagcgagg gtgggcggcg cggagggag    660 ctggacccca tggacgtccg cggctccatc gtctacctgg agattgacaa ccggcagtgt    720
gtgcaggcct cctcgcagtg cttccagagt gccaccgacg tggccgcatt cctgggagcg    780
ctcgcctcgc tgggcagcct caacatcccc tacaagatcg aggccgtgca gagtgagacc    840
gtggagccgc ccccgccggc gcag                                            864

<210> SEQ ID NO 22
<211> LENGTH: 288
<212> TYPE: PRT
<213> ORGANISM: Homo sapiens

<400> SEQUENCE: 22

Glu Glu Ala Cys Glu Leu Pro Glu Cys Gln Glu Asp Ala Gly Asn Lys
1               5                   10                  15

Val Cys Ser Leu Gln Cys Asn Asn His Ala Cys Gly Trp Asp Gly Gly
                20                  25                  30

Asp Cys Ser Leu Asn Phe Asn Asp Pro Trp Lys Asn Cys Thr Gln Ser
            35                  40                  45

Leu Gln Cys Trp Lys Tyr Phe Ser Asp Gly His Cys Asp Ser Gln Cys
        50                  55                  60

Asn Ser Ala Gly Cys Leu Phe Asp Gly Phe Asp Cys Gln Arg Ala Glu

```
                65                  70                  75                  80
        Gly Gln Cys Asn Pro Leu Tyr Asp Gln Tyr Cys Lys Asp His Phe Ser
                         85                  90                  95

Asp Gly His Cys Asp Gln Gly Cys Asn Ser Ala Glu Cys Glu Trp Asp
                        100                 105                 110

Gly Leu Asp Cys Ala Glu His Val Pro Glu Arg Leu Ala Ala Gly Thr
                    115                 120                 125

Leu Val Val Val Leu Met Pro Pro Glu Gln Leu Arg Asn Ser Ser
                130                 135                 140

Phe His Phe Leu Arg Glu Leu Ser Arg Val Leu His Thr Asn Val Val
        145                 150                 155                 160

Phe Lys Arg Asp Ala His Gly Gln Gln Met Ile Phe Pro Tyr Tyr Gly
                        165                 170                 175

Arg Glu Glu Glu Leu Arg Lys His Pro Ile Lys Arg Ala Ala Glu Gly
                        180                 185                 190

Trp Ala Ala Pro Asp Ala Leu Leu Gly Gln Val Lys Ala Ser Leu Leu
                    195                 200                 205

Pro Gly Gly Ser Glu Gly Gly Arg Arg Arg Glu Leu Asp Pro Met
            210                 215                 220

Asp Val Arg Gly Ser Ile Val Tyr Leu Glu Ile Asp Asn Arg Gln Cys
        225                 230                 235                 240

Val Gln Ala Ser Ser Gln Cys Phe Gln Ser Ala Thr Asp Val Ala Ala
                        245                 250                 255

Phe Leu Gly Ala Leu Ala Ser Leu Gly Ser Leu Asn Ile Pro Tyr Lys
                    260                 265                 270

Ile Glu Ala Val Gln Ser Glu Thr Val Glu Pro Pro Pro Ala Gln
                275                 280                 285

<210> SEQ ID NO 23
<211> LENGTH: 42
<212> TYPE: PRT
<213> ORGANISM: Artificial Sequence
<220> FEATURE:
<223> OTHER INFORMATION: Synthetic peptide sequence

<400> SEQUENCE: 23

Ala Cys Glu Leu Pro Glu Cys Gln Glu Asp Ala Gly Asn Lys Val Cys
1               5                   10                  15

Ser Leu Gln Cys Asn Asn His Ala Cys Gly Trp Asp Gly Gly Asp Cys
                20                  25                  30

Ser Leu Asn Phe Asn Asp Pro Trp Lys Asn
            35                  40

<210> SEQ ID NO 24
<211> LENGTH: 42
<212> TYPE: PRT
<213> ORGANISM: Artificial Sequence
<220> FEATURE:
<223> OTHER INFORMATION: Synthetic peptide sequence

<400> SEQUENCE: 24

Ala Cys Glu Leu Pro Glu Cys Gln Val Asp Ala Gly Asn Lys Val Cys
1               5                   10                  15

Asn Leu Gln Cys Asn Asn His Ala Cys Gly Trp Asp Gly Gly Asp Cys
                20                  25                  30

Ser Leu Asn Phe Asn Asp Pro Trp Lys Asn
            35                  40
```

```
<210> SEQ ID NO 25
<211> LENGTH: 42
<212> TYPE: PRT
<213> ORGANISM: Artificial Sequence
<220> FEATURE:
<223> OTHER INFORMATION: Synthetic peptide sequence

<400> SEQUENCE: 25

Ala Cys Glu Leu Pro Glu Cys Gln Ala Asp Ala Gly Asn Lys Val Cys
1               5                   10                  15

Ser Leu Gln Cys Asn Asn His Ala Cys Gly Trp Asp Gly Gly Asp Cys
            20                  25                  30

Ser Leu Asn Phe Asn Asp Pro Trp Lys Asn
        35                  40

<210> SEQ ID NO 26
<211> LENGTH: 42
<212> TYPE: PRT
<213> ORGANISM: Artificial Sequence
<220> FEATURE:
<223> OTHER INFORMATION: Synthetic peptide sequence

<400> SEQUENCE: 26

Ala Cys Glu Leu Pro Glu Cys Gln Glu Asp Ala Gly Asn Ala Val Cys
1               5                   10                  15

Ser Leu Gln Cys Asn Asn His Ala Cys Gly Trp Asp Gly Gly Asp Cys
            20                  25                  30

Ser Leu Asn Phe Asn Asp Pro Trp Lys Asn
        35                  40

<210> SEQ ID NO 27
<211> LENGTH: 42
<212> TYPE: PRT
<213> ORGANISM: Artificial Sequence
<220> FEATURE:
<223> OTHER INFORMATION: Synthetic peptide sequence

<400> SEQUENCE: 27

Ala Cys Glu Leu Pro Glu Cys Gln Glu Asp Ala Gly Asn Lys Ala Cys
1               5                   10                  15

Ser Leu Gln Cys Asn Asn His Ala Cys Gly Trp Asp Gly Gly Asp Cys
            20                  25                  30

Ser Leu Asn Phe Asn Asp Pro Trp Lys Asn
        35                  40

<210> SEQ ID NO 28
<211> LENGTH: 42
<212> TYPE: PRT
<213> ORGANISM: Artificial Sequence
<220> FEATURE:
<223> OTHER INFORMATION: Synthetic peptide sequence

<400> SEQUENCE: 28

Ala Cys Glu Leu Pro Glu Cys Gln Glu Asp Ala Gly Asn Lys Val Cys
1               5                   10                  15

Asn Leu Gln Cys Asn Asn His Ala Cys Gly Trp Asp Gly Gly Asp Cys
            20                  25                  30

Ser Leu Asn Phe Asn Asp Pro Trp Lys Asn
        35                  40

<210> SEQ ID NO 29
<211> LENGTH: 42
```

```
<212> TYPE: PRT
<213> ORGANISM: Artificial Sequence
<220> FEATURE:
<223> OTHER INFORMATION: Synthetic peptide sequence

<400> SEQUENCE: 29

Ala Cys Glu Leu Pro Glu Cys Gln Glu Asp Ala Gly Asn Lys Val Cys
1               5                   10                  15

Ser Ala Gln Cys Asn Asn His Ala Cys Gly Trp Asp Gly Gly Asp Cys
            20                  25                  30

Ser Leu Asn Phe Asn Asp Pro Trp Lys Asn
            35                  40

<210> SEQ ID NO 30
<211> LENGTH: 42
<212> TYPE: PRT
<213> ORGANISM: Artificial Sequence
<220> FEATURE:
<223> OTHER INFORMATION: Synthetic peptide sequence

<400> SEQUENCE: 30

Ala Cys Glu Leu Pro Glu Cys Gln Glu Asp Ala Gly Asn Lys Val Cys
1               5                   10                  15

Ser Leu Ala Cys Asn Asn His Ala Cys Gly Trp Asp Gly Gly Asp Cys
            20                  25                  30

Ser Leu Asn Phe Asn Asp Pro Trp Lys Asn
            35                  40

<210> SEQ ID NO 31
<211> LENGTH: 35
<212> TYPE: PRT
<213> ORGANISM: Artificial Sequence
<220> FEATURE:
<223> OTHER INFORMATION: Synthetic peptide sequence

<400> SEQUENCE: 31

Phe Leu Gly Ala Leu Ala Ser Leu Gly Ser Leu Asn Ile Pro Tyr Lys
1               5                   10                  15

Ile Glu Ala Val Gln Ser Glu Thr Val Glu Pro Pro Pro Pro Ala Gln
            20                  25                  30

Lys Arg Arg
        35

<210> SEQ ID NO 32
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 32

Phe Leu Ala Ser His Ala Ile Gln Gly
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 33

Gly Thr Leu Asn Ile Ser Tyr Pro Ile
1               5
```

<210> SEQ ID NO 34
<211> LENGTH: 8
<212> TYPE: PRT
<213> ORGANISM: Artificial Sequence
<220> FEATURE:
<223> OTHER INFORMATION: Synthetic peptide sequence

<400> SEQUENCE: 34

Lys Leu Val Ser Val Val Ser Glu
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 35

Glu Ser Leu Glu Thr Pro Pro
1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic peptide sequence

<400> SEQUENCE: 36

Pro Glu Arg Thr Gln Lys Ser Arg
1               5

<210> SEQ ID NO 37
<211> LENGTH: 352
<212> TYPE: PRT
<213> ORGANISM: Artificial Sequence
<220> FEATURE:
<223> OTHER INFORMATION: Synthetic peptide sequence

<400> SEQUENCE: 37

Glu Cys Gln Phe Pro Ala Ser Ser Pro Cys Leu Gly Asn Pro Cys
1               5                   10                  15

Tyr Asn Gln Gly Thr Cys Glu Pro Thr Ser Glu Ser Pro Phe Tyr Arg
            20                  25                  30

Cys Leu Cys Pro Ala Lys Phe Asn Gly Leu Leu Cys His Ile Leu Asp
        35                  40                  45

Tyr Ser Phe Gly Gly Gly Ala Gly Arg Asp Ile Pro Pro Leu Ile
    50                  55                  60

Glu Glu Ala Cys Glu Leu Pro Glu Cys Gln Glu Asp Ala Gly Asn Lys
65                  70                  75                  80

Val Cys Ser Leu Gln Cys Asn Asn His Ala Cys Gly Trp Asp Gly Gly
                85                  90                  95

Asp Cys Ser Leu Asn Phe Asn Asp Pro Trp Lys Asn Cys Thr Gln Ser
            100                 105                 110

Leu Gln Cys Trp Lys Tyr Phe Ser Asp Gly His Cys Asp Ser Gln Cys
        115                 120                 125

Asn Ser Ala Gly Cys Leu Phe Asp Gly Phe Asp Cys Gln Arg Ala Glu
    130                 135                 140

Gly Gln Cys Asn Pro Leu Tyr Asp Gln Tyr Cys Lys Asp His Phe Ser
145                 150                 155                 160

```
Asp Gly His Cys Asp Gln Gly Cys Asn Ser Ala Glu Cys Glu Trp Asp
            165                 170                 175
Gly Leu Asp Cys Ala Glu His Val Pro Glu Arg Leu Ala Ala Gly Thr
        180                 185                 190
Leu Val Val Val Leu Met Pro Pro Glu Gln Leu Arg Asn Ser Ser
        195                 200                 205
Phe His Phe Leu Arg Glu Leu Ser Arg Val Leu His Thr Asn Val Val
    210                 215                 220
Phe Lys Arg Asp Ala His Gly Gln Gln Met Ile Phe Pro Tyr Tyr Gly
225                 230                 235                 240
Arg Glu Glu Glu Leu Arg Lys His Pro Ile Lys Arg Ala Ala Glu Gly
                245                 250                 255
Trp Ala Pro Asp Ala Leu Leu Gly Gln Val Lys Ala Ser Leu Leu
            260                 265                 270
Pro Gly Gly Ser Glu Gly Gly Arg Arg Arg Glu Leu Asp Pro Met
        275                 280                 285
Asp Val Arg Gly Ser Ile Val Tyr Leu Glu Ile Asp Asn Arg Gln Cys
290                 295                 300
Val Gln Ala Ser Ser Gln Cys Phe Gln Ser Ala Thr Asp Val Ala Ala
305                 310                 315                 320
Phe Leu Gly Ala Leu Ala Ser Leu Gly Ser Leu Asn Ile Pro Tyr Lys
                325                 330                 335
Ile Glu Ala Val Gln Ser Glu Thr Val Glu Pro Pro Pro Ala Gln
            340                 345                 350

<210> SEQ ID NO 38
<211> LENGTH: 351
<212> TYPE: PRT
<213> ORGANISM: Artificial Sequence
<220> FEATURE:
<223> OTHER INFORMATION: Synthetic peptide sequence

<400> SEQUENCE: 38

Asp Cys Glu Ser Gly Cys Ala Ser Ser Pro Cys Gln His Gly Gly Ser
1               5                   10                  15
Cys His Pro Gln Arg Gln Pro Pro Tyr Tyr Ser Cys Gln Cys Ala Pro
            20                  25                  30
Pro Phe Ser Gly Ser Arg Cys Glu Leu Tyr Thr Ala Pro Pro Ser Thr
        35                  40                  45
Pro Pro Ala Thr Cys Leu Ser Gln Tyr Cys Ala Asp Lys Ala Arg Asp
    50                  55                  60
Gly Val Cys Asp Glu Ala Cys Asn Ser His Ala Cys Gln Trp Asp Gly
65                  70                  75                  80
Gly Asp Cys Ser Leu Thr Met Glu Asn Pro Trp Ala Asn Cys Ser Ser
                85                  90                  95
Pro Leu Pro Cys Trp Asp Tyr Ile Asn Asn Gln Cys Asp Glu Leu Cys
            100                 105                 110
Asn Thr Val Glu Cys Leu Phe Asp Asn Phe Glu Cys Gln Gly Asn Ser
        115                 120                 125
Lys Thr Cys Lys Tyr Asp Lys Tyr Cys Ala Asp His Phe Lys Asp Asn
    130                 135                 140
His Cys Asp Gln Gly Cys Asn Ser Glu Glu Cys Gly Trp Asp Gly Leu
145                 150                 155                 160
Asp Cys Ala Ala Asp Gln Pro Glu Asn Leu Ala Glu Gly Thr Leu Val
                165                 170                 175
```

```
Ile Val Val Leu Met Pro Pro Glu Gln Leu Leu Gln Asp Ala Arg Ser
            180             185             190

Phe Leu Arg Ala Leu Gly Thr Leu Leu His Thr Asn Leu Arg Ile Lys
        195             200             205

Arg Asp Ser Gln Gly Glu Leu Met Val Tyr Pro Tyr Tyr Gly Glu Lys
    210             215             220

Ser Ala Ala Met Lys Lys Gln Arg Met Thr Arg Arg Ser Leu Pro Gly
225             230             235             240

Glu Gln Glu Gln Glu Val Ala Gly Ser Lys Val Phe Leu Glu Ile Asp
                245             250             255

Asn Arg Gln Cys Val Gln Asp Ser Asp His Cys Phe Lys Asn Thr Asp
            260             265             270

Ala Ala Ala Ala Leu Leu Ala Ser His Ala Ile Gln Gly Thr Leu Ser
        275             280             285

Tyr Pro Leu Val Ser Val Val Ser Glu Ser Leu Thr Pro Glu Arg Thr
    290             295             300

Gln Lys Ser Arg Arg Gln His Gly Gln Leu Trp Phe Pro Glu Gly Phe
305             310             315             320

Lys Val Ser Glu Ala Ser Lys Lys Lys Arg Ser Glu Pro Leu Gly Glu
                325             330             335

Asp Ser Val Gly Leu Lys Pro Leu Lys Asn Ala Ser Asp Leu Glu
                340             345             350
```